United States Patent
Bond et al.

(10) Patent No.: US 11,155,547 B1
(45) Date of Patent: Oct. 26, 2021

(54) COMPOUNDS FOR AND METHODS OF TREATING DISEASES

(71) Applicant: Alterity Therapeutics Limited, Melbourne (AU)

(72) Inventors: Silas Bond, Melbourne (AU); Penelope Jane Huggins, Melbourne (AU); Jack Gordon Parsons, Melbourne (AU)

(73) Assignee: Alterity Therapeutics Limited, Melbourne (AU)

( * ) Notice: Subject to any disclaimer, the term of this patent is extended or adjusted under 35 U.S.C. 154(b) by 0 days.

(21) Appl. No.: 17/239,375

(22) Filed: Apr. 23, 2021

(30) Foreign Application Priority Data

Jun. 18, 2020 (AU) .................. 2020902019

(51) Int. Cl.
 *C07D 471/04* (2006.01)
 *C07D 487/04* (2006.01)

(52) U.S. Cl.
 CPC ......... *C07D 471/04* (2013.01); *C07D 487/04* (2013.01)

(58) Field of Classification Search
 CPC ............................ C07D 471/04; C07D 487/04
 USPC ..................................................... 514/233.2
 See application file for complete search history.

(56) References Cited

U.S. PATENT DOCUMENTS 10,941,143 B2    3/2021   Bond et al.

FOREIGN PATENT DOCUMENTS

WO    2005037836 A1    4/2005
WO    2009143051 A1    11/2009

OTHER PUBLICATIONS

Melekhina et al., Tetrahedron Letters (2019), 60(39), 151080.* sp3 C—H amination', Organic and Biomolecular Chemistry, 2018, vol. 16, pp. 5653-5660.

Khan, M. S. et al., 'Design, Synthesis, Evaluation and Thermodynamics of 1-Substituted Pyridylimidazo[1,5-a]Pyridine Derivatives as Cysteine Protease Inhibitors', PLOS One (2013), vol. 8, issue 8, e69982.

Muniyan, S. et al., 'Antiproliferative activity of novel imidazopyridine derivatives on castration-resistant human prostate cancer cells', Cancer Letters (2014), vol. 353, No. 1, pp. 59-67.

Australian Search Report for Application No. 2019900867 dated Aug. 19, 2019 (22 pages).

\* cited by examiner

*Primary Examiner* — Niloofar Rahmani
(74) *Attorney, Agent, or Firm* — Michael Best & Friedrich LLP

(57) ABSTRACT

The present invention provides heterocyclic compounds of formula (I) that modulate biological metals and to pharmaceutical compositions containing such compounds. The invention particularly relates to compounds that modulate iron and to compounds for the treatment of diseases, particularly neurological diseases such as Parkinson's disease (PD), Alzheimer's disease (AD), Alzheimer-type dementia, Huntington's disease (HD), amyotrophic lateral sclerosis (ALS), frontotemporal dementia (FTD) and multiple system atrophy (MSA).

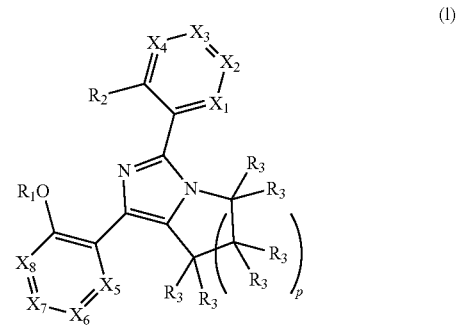

18 Claims, No Drawings

COMPOUNDS FOR AND METHODS OF TREATING DISEASES

CROSS-REFERENCE TO RELATED APPLICATIONS

This application claims priority to Australian Patent Application No. 2020902019, filed Jun. 18, 2020, the entire contents of which is hereby fully incorporated by reference.

FIELD OF THE INVENTION

The present invention provides compounds that modulate biological metals and to pharmaceutical compositions containing such compounds. The invention particularly relates to compounds that modulate iron and to compounds for the treatment of diseases, particularly neurological diseases such as Parkinson's disease (PD), Alzheimer's disease (AD), Alzheimer-type dementia, Huntington's disease (HD), amyotrophic lateral sclerosis (ALS), frontotemporal dementia (FTD) and multiple system atrophy (MSA).

BACKGROUND OF THE INVENTION

Biological metals, including iron, are essential for living cell metabolism but must be held under extremely tight control in all physiological conditions. In certain disease conditions, metal ion management can be disrupted, resulting in elevated levels of metal that accumulate in tissues or organs. Excessive iron for example shows a wide range of toxic effects on tissues, depending on the metal's redox activity.

Oxidative stress has been described as very relevant to the physical damage observed in many neurodegenerative disorders, such as Parkinson's disease (PD) and Alzheimer's disease (AD). In the presence of molecular oxygen, iron can redox cycle between the two most stable oxidation states iron(II) and iron(III), generating oxygen-derived free radicals—such as hydroxyl radicals (.OR). These radicals are highly reactive species which are able to interact with multiple biological molecules, leading to tissue damage.

Cells adopt a number of protective strategies to prevent the formation or production of such highly reactive species, however a state of disease can overwhelm these processes. The brain, like all other tissues, protects itself against the deleterious effects of oxygen free radicals by protective enzymes such as glutathione peroxidase (GP), catalase and superoxide dismutase (SD). Protection is also afforded by relatively high amounts of glutathione and ascorbate. Parkinson's disease is a progressive neurodegeneration of the dopaminergic neurons in the substantia nigra (SN) of patients' brains. PD patients are identified to have higher levels of iron in the SN of their brain, where the important neurotransmitter dopamine (DA) has a critical physiological function.

Postmortem studies on brains from parkinsonian patients suggest the involvement of oxygen free radical-induced oxidative stress which results in lipid peroxidation of cell membranes, followed by increased membrane fluidity and finally cell death. Normally DA is metabolized in ways that lead to an excess of toxic oxygen species, such as .OH, which in the presence of a transient metal, such as iron, will produce cytotoxic oxygen free radicals, e.g. Superoxide and hydroxyl free radicals (.OR).

In PD, the above described brain defensive mechanisms against the formation of cytotoxic oxygen free radicals are defective. In the SN of parkinsonian brains there are reductions in activities of SD and GP and reduced tissue contents of glutathione and ascorbate. Moreover, iron concentrations are significantly elevated in parkinsonian SN within the dopamine neurons. The treatment of mice with the metal modulator Clioquinol has been shown to protect mice from the effects of 1-methyl-4-phenyl-1,2,3,6-tetrahydropyridine (MPTP) which causes Parkinson's symptoms. In further experiments, it has been shown that mice which are genetically engineered to express the natural iron-binding protein ferritin in the mouse SN have less available iron in their brains and are also protected from the effects of MPTP. Significantly, the mice tolerated the resulting reduction of available iron in their brains without serious side effects no matter how the iron levels were reduced.

Evidence suggests that whilst iron itself can induce oxidative processes, so too can proteins with iron binding sites. In AD, the plaque-forming Aβ peptide will redox cycle iron(III) and produce hydrogen peroxide ($H_2O_2$) by double electron transfer to $O_2$. $H_2O_2$ is a pro-oxidant molecule that reacts with reduced metal ions, such as iron(II) to generate the highly reactive hydroxyl radical (.OH) via the Fenton reaction. This process in turn induces numerous adducts and protein modifications.

Critical to Alzheimer's Disease are extensive changes to all classes of macromolecules, along with apoptotic mechanisms of cell damage/death, which is partly mediated by $H_2O_2$. Principally, Aβ peptide Fenton redox activity is reliant on the iron metal binding site of Aβ peptide. The existence of this site suggests that compounds with the ability to modulate metals, including the concentration of intracellular metals or block metal binding sites will be a direct treatment for AD.

In turn, these conditions cause release of cytotoxic free radicals, resulting in neuronal death.

It would be highly desirable to find iron modulators that exhibit the remaining qualities necessary for the treatment of metal-associated disorders.

SUMMARY OF THE INVENTION

The present invention is predicated at least in part on the discovery that certain compounds are capable of modulating iron, thus making them suitable candidates for treatment of Parkinson's disease and other metal associated disorders.

In a first aspect, the present invention provides a compound of formula (I):

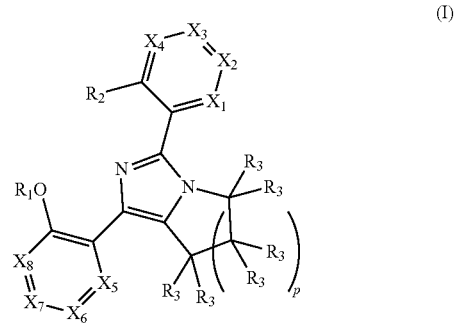

wherein
each of $X_1$ to $X_8$ are independently N and $CR_3$, wherein 0, 1, 2, 3 or 4 of $X_1$ to $X_8$ are N;
$R_1$ is selected from the group consisting of hydrogen, alkyl, alkenyl, alkynyl, $(C(R_7)_2)_m$aryl, $C(O)R_4$ and $C(S)R_4$;

$R_2$ is selected from the group consisting of hydrogen, halo, $OR_5$, $SR_5$, $C(O)R_4$, $C(S)R_4$, $NO_2$, CN, $N(R_6)_2$, $S(O)_nN(R_6)_2$ and $S(O)_nR_4$;

each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mOC(S)R_4$, $(C(R_7)_2)_mSC(O)R_4$, $(C(R_7)_2)_mSC(S)R_4$, $(C(R_7)_2)_mCN$, $(C(R_7)_2)_mNO_2$, $(C(R_7)_2)_mN(R_6)_2$, $(C(R_7)_2)_mN(R_6)C(O)N(R_6)_2$ and $(C(R_7)_2)_mN(R_6)C(S)N(R_6)_2$;

$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;

$R_5$ is selected from the group consisting of hydrogen, alkyl, alkenyl, alkynyl, haloalkyl, cycloalkyl, cycloalkenyl, aryl, heterocyclyl, heteroaryl, C(O)alkyl, C(O)alkenyl, C(O)alkynyl, $S(O)_nR_4$ and $S(O)_nN(R_6)_2$;

$R_6$ is selected from the group consisting of hydrogen, alkyl, alkenyl, alkynyl, haloalkyl, cycloalkyl, cycloalkenyl, aryl, heterocyclyl and heteroaryl;

each $R_7$ is independently selected from the group consisting of hydrogen, alkyl, alkenyl, alkynyl and haloalkyl;

m is 0 or an integer from 1 to 6;

n is 1 or 2;

p is an integer from 1 to 4;

wherein each alkyl, alkenyl, alkynyl, cycloalkyl, cycloalkenyl, aryl, heterocyclyl and heteroaryl is optionally substituted;

or a pharmaceutically acceptable salt, stereoisomer or solvate thereof.

In another aspect of the invention there is provided a pharmaceutical composition comprising a compound of formula (I) or a pharmaceutically acceptable salt or solvate thereof and a pharmaceutically acceptable carrier and/or excipient.

In yet another aspect of the invention there is provided a method of treating or preventing a metal ion associated disorder comprising administering to a subject a compound of formula (I) or a pharmaceutically acceptable salt or solvate thereof.

In yet another aspect of the invention there is provided a method of beating or preventing a metal ion associated neurological disorder comprising administering to a subject a compound of formula (I) or a pharmaceutically acceptable salt or solvate thereof.

In a further aspect of the invention, there is provided a compound of formula (I) or a pharmaceutically acceptable salt or solvate thereof for use in beating or preventing a metal ion associated disorder. In a further embodiment, the disorder is a neurological disorder.

In yet a further aspect of the invention, there is provided a use of a compound of formula (I) or a pharmaceutically acceptable salt or solvate thereof in the manufacture of a medicament for beating or preventing metal ion associated disorder. In a further embodiment, the disorder is a neurological disorder.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, i-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

The term "haloalkyl" as used herein refers to an alkyl group as defined above where one or more hydrogen atoms have been replaced with a halogen atom and includes perhalogenated alkyl groups. Examples of suitable haloalkyl groups include fluoromethyl, difluoromethyl, trifluoromethyl, chloromethyl, dichloromethyl, trichloromethyl, chlorofluoromethyl, difluorochloromethyl, dichlorofluoromethyl, bromomethyl, iodomethyl, 1-fluoroethyl, 2-fluoroethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-chloropropyl, 2-chloropropyl, 3-chloropropyl, and the like.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 10 membered cycloalkyl group includes 3, 4, 5, 6, 7, 8, 9 or 10 carbon atoms. Examples of suitable cycloalkyl groups include, but are not limited to, cyclopropyl, cyclobutyl, cyclopentyl, cyclohexyl, cycloheptyl, cyclooctyl, cyclononyl and cyclodecyl.

As used herein, the term "cycloalkenyl" refers to an unsaturated cyclic hydrocarbon. The cycloalkenyl ring may include a specified number of carbon atoms. For example, a 5 to 10 membered cycloalkenyl group includes 5, 6, 7, 8, 9 or 10 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl, cyclooctatrienyl, cyclononenyl, cyclononadienyl, cyclononatrienyl, cyclodecenyl, cyclodecadienyl and cyclodecatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon, such as a cycloalkyl or cycloalkenyl defined above, in which one to four carbon atoms have been replaced by heteroatoms independently selected from the group consisting of N, N(R), S, S(O), $S(O)_2$ and O. A heterocyclic ring may be saturated or unsaturated but not aromatic. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,2,3-thiadiazolyl, 1,3,5-triazinyl, 1,2,4-triazinyl, 1,2,4,5-tetrazinyl and tetrazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2H$, —$CO_2C_{1-6}$alkyl, —$NH_2$, —NH($C_{1-6}$alkyl), —N($C_{1-6}$alkyl)$_2$, —NH(phenyl), —N(phenyl)$_2$, —CN, —$NO_2$, -halogen, —$CF_3$, —$OCF_3$, —$SCF_3$, —$CHF_2$, —$OCHF_2$, —$SCHF_2$, -phenyl, -heterocyclyl, -heteroaryl, —Oheteroaryl, —Oheterocyclyl, —Ophenyl, —C(=O)phenyl, —C(=O)$C_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, oxo, hydroxymethyl, hydroxyethyl, hydroxypropyl, hydroxybutyl, fluoro, chloro, bromo, iodo, cyano, nitro, —$CO_2H$, —$CO_2CH_3$, trifluoromethyl, trifluoromethoxy, trifluoromethylthio, difluoromethyl, difluoromethoxy, difluoromethylthio, morpholino, amino, methylamino, dimethylamino, ethylamino, diethylamino, phenyl, phenoxy, phenylcarbonyl, benzyl and acetyl. The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, malonic, malic (L), lactic (DL), mandelic (DL), gluconic, carbonic, benzoic, succinic, oxalic, phenylacetic, methanesulphonic, ethanesulphonic, toluenesulphonic, camphorsulphonic, benzenesulphonic, salicylic, cinnamic, cyclamic, sulphanilic, aspartic, glutamic, glutaric, galactaric, gentisic, hippuric, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, aluminium, zinc, lysine, histidine, meglumine, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The compounds of the invention may also be in the form of solvates, including hydrates. The term "solvate" is used herein to refer to a complex of variable stoichiometry formed by a solute (a compound of formula (I)) and a solvent. Such solvents should not interfere with the biological activity of the solute. Solvents that may be included in a solvate include, but are not limited to, water, ethanol, propanol, and acetic acid. Methods of solvation are generally known within the art.

The term "pro-drug" is used in its broadest sense and encompasses those derivatives that are converted in vivo to the compounds of formula (I). Such derivatives would readily occur to those skilled in the art and include, for example, compounds where a free hydroxy group is converted into an ester derivative or a ring nitrogen is converted to an N-oxide. Examples of ester derivatives include alkyl esters, phosphate esters and those formed from amino acids. Conventional procedures for the preparation of suitable prodrugs are described in text books such as "Design of Prodrugs" Ed. H. Bundgaard, Elsevier, 1985.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than about 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or Ira ns (E) or mixtures thereof.

The compounds of the invention may also exist in the form of rotational isomers or conformers where there is restricted or hindered rotation about a single bond.

Any formula or structure given herein, including Formula (I) compounds are also intended to represent unlabelled forms as well as isotopically labelled forms of the compounds for use as medicaments or as a study tool. This may include metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labelled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{10}$B, $^{11}$C, $^{13}$C, $^{14}$C, $^{15}$N, $^{18}$F, $^{31}$P, $^{32}$P, $^{35}$S, $^{36}$Cl and $^{125}$I. Various isotopically labelled compounds of the present disclosure, for example those into which radioactive isotopes such as $^3$H, $^{13}$C and $^{14}$C are incorporated. In addition to use as pharmaceutical treatments, such isotopically labelled compounds may be useful.

Compounds of the Invention

The present invention provides metal ion modulating compounds, particularly iron selective ion modulating compounds. Such modulators may have one or more of the desirable properties of: orally deliverable; low liver extraction, non-toxicity and the ability to modulate metals, particularly iron in the central nervous system (CNS). Advantageous metal selectivity, affinity and kinetic stability of the complexes formed are also provided by preferred compounds.

In order for a modulating compound to exert its pharmacological effect, it must be able to reach the target sites at a sufficient concentration. Therefore, a preferred key property of an orally active iron modulator is its ability to be efficiently absorbed from the gastrointestinal tract (GI). The metabolic properties of modulator agents play a critical role in determining both their efficacy and toxicity. Toxicity associated with iron originates from a number of factors, but critically on their ability to inhibit many iron-containing enzymes like tyrosine hydroxylase (the brain enzyme involved in the biosynthesis of L-DOPA) and ribonucleotide reductase. Thus, in a first aspect the present invention provides a compound of formula (I):

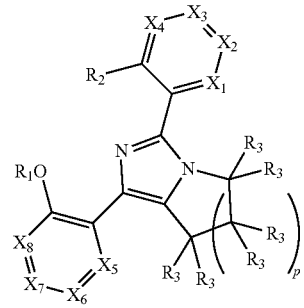

wherein
each of $X_1$ to $X_8$ are independently selected from the group consisting of N and $CR_3$, wherein 0, 1, 2, 3 or 4 of $X_1$ to $X_8$ are N;
$R_1$ is selected from the group consisting of hydrogen, alkyl, alkenyl, alkynyl, $(C(R_7)_2)_m$aryl, $C(O)R_4$ and $C(S)R_4$;
$R_2$ is selected from the group consisting of hydrogen, halo, $OR_5$, $SR_5$, $C(O)R_4$, $C(S)R_4$, $NO_2$, $CN$, $N(R_6)_2$, $OS(O)_nN(R_6)_2$ and $OS(O)_nR_4$;
each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$. $(C(R_7)_2)_m N(R_6)C(O)N(R_6)_2$ and $(C(R_7)_2)_m N(R_6)C(S)N(R_6)_2$;
$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;
$R_5$ is selected from the group consisting of hydrogen, alkyl, alkenyl, alkynyl, haloalkyl, cycloalkyl, cycloalkenyl, aryl, heterocyclyl, heteroaryl, C(O)alkyl, C(O)alkenyl, C(O)alkynyl, $S(O)_n R_4$ and $S(O)_n N(R_6)_2$;
$R_6$ is selected from the group consisting of hydrogen, alkyl, alkenyl, alkynyl, haloalkyl, cycloalkyl, cycloalkenyl, aryl, heterocyclyl and heteroaryl;
each $R_7$ is independently selected from the group consisting of hydrogen, alkyl, alkenyl, alkynyl and haloalkyl;
m is 0 or an integer from 1 to 6;
n is 1 or 2;
p is an integer from 1 to 4;
wherein each alkyl, alkenyl, alkynyl, cycloalkyl, cycloalkenyl, aryl, heterocyclyl and heteroaryl is optionally substituted;
or a pharmaceutically acceptable salt, stereoisomer or solvate thereof.

In some embodiments, $X_1$ to $X_8$ are each independently $CR_3$. In other embodiments, one of $X_1$ to $X_8$ is N and the remainder are $CR_3$. In yet other embodiments, two of $X_1$ to $X_8$ are N and the remainder are $CR_3$. In yet other embodiments, three of $X_1$ to $X_8$ are N and the remainder are $CR_3$. In yet further embodiments, four of $X_1$ to $X_8$ are N and the remainder are $CR_3$. In particular embodiments, $X_1$ to $X_8$ are each independently $CR_3$ or one of $X_1$ to $X_8$ is N and the remainder are $CR_3$.

In some embodiments, one of $X_1$ to $X_4$ is N. In other embodiments, one of $X_5$ to $X_8$ is N. In particular embodiments, one of $X_1$, $X_5$, $X_6$, $X_7$ and $X_8$ is N.

In some embodiments, one to $X_1$ to $X_4$ is N and two of $X_5$ to $X_8$ are N. In other embodiments, two of $X_1$ to $X_4$ are N and one of $X_5$ to $X_8$ is N.

In some embodiments, two of $X_1$ to $X_4$ are N and two of $X_5$ to $X_8$ are N.

In yet other embodiments, one of $X_1$ to $X_4$ and one of $X_5$ to $X_8$ are N. In some embodiments, two of $X_1$, $X_5$, $X_6$, $X_7$ and $X_8$ are N.

In some embodiments, where 2 or 3 of $X_1$ to $X_8$ are N, no more than two nitrogen atoms are located adjacent to each other in a ring. For example, if $X_5$ and $X_7$ are both N, $X_6$ could not be N.

In particular embodiments, one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer from 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, SH, fluoro, chloro, bromo, $OC_{1-6}$alkyl, $SC_{1-6}$alkyl, $C(O)$$OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_nC_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH; Each $R_3$ is selected from the group consisting of hydrogen, halo, $C_{1-6}$alkyl, $C_{2-6}$alkenyl, $C_{1-6}$haloalkyl, cycloalkyl, cycloalkenyl, aryl, heterocyclyl, heteroaryl, $(CH_2)_q$cycloalkyl, $(CH_2)_q$cycloalkenyl, $(CH_2)_q$aryl, $(CH_2)_q$heterocyclyl, $(CH_2)_q$heteroaryl, OH, $(CH_2)_q$OH, SH, $(CH_2)_q$SH, $OC_{1-6}$alkyl, $SC_{1-6}$alkyl, $(CH_2)_qOC_{1-6}$alkyl, $(CH_2)_q$$SC_{1-6}$ alkyl, $OC(O)C_{1-6}$alkyl, $(CH_2)_qOC(O)C_{1-6}$alkyl, $C(O)$$C_{1-6}$ alkyl, $(CH_2)_qC(O)C_{1-6}$alkyl, $CO_2H$, $(CH_2)_qCO_2H$, $C(O)OC_{1-6}$alkyl, $(CH_2)_qC(O)OC_{1-6}$alkyl, $CONH_2$, $(CH_2)_q$$CONH_2$, CN, $(CH_2)_qCN$, $NO_2$, $(CH_2)_qNO_2$, $NH_2$, $NH(C_{1-6}$alkyl), $N(C_{1-6}$alkyl$)_2$, $(CH_2)_qNH_2$, $(CH_2)_qNH(C_{1-6}$alkyl), $(CH_2)_qN(C_{1-6}$alkyl$)_2$, $SO_2H$, $(CH_2)_qSO_2H$, $SO_3H$, $(CH_2)_q$$SO_3H$, $S(O)_2C_{1-6}$alkyl, $(CH_2)_qS(O)_2C_{1-6}$alkyl, $S(O)_2OC_{1-6}$ alkyl, $(CH_2)_qS(O)_2OC_{1-6}$alkyl, $S(O)_2NH_2$, $S(O)_2NH(C_{1-6}$ alkyl), $S(O)_2N(C_{1-6}$alkyl$)_2$, $(CH_2)_qS(O)_2NH_2$, $(CH_2)_qS(O)_2$$NH(C_{1-6}$alkyl), $(CH_2)_qS(O)_2N(C_{1-6}$alkyl$)_2$, $NHC(O)NH_2$, $NHC(O)NH(C_{1-6}$alkyl), $NHC(O)N(C_{1-6}$alkyl$)_2$, $(CH_2)_q$$NHC(O)NH_2$, $(CH_2)_qNHC(O)NH(C_{1-6}$alkyl) and $(CH_2)_q$$NHC(O)N(C_{1-6}$alkyl$)_2$ where q is an integer of from 1 to 3; especially hydrogen, halo, $C_{1-6}$alkyl, $C_{1-6}$haloalkyl, heterocyclyl, heteroaryl, $(CH_2)_q$heterocyclyl, $(CH_2)_q$heteroaryl, OH, $(CH_2)_q$OH, $OC_{1-6}$alkyl, $SC_{1-6}$alkyl, $(CH_2)_qOC_{1-6}$alkyl, $(CH_2)_qSC_{1-6}$alkyl, $OC(O)C_{1-6}$alkyl, $(CH_2)_qOC(O)C_{1-6}$alkyl, $C(O)C_{1-6}$alkyl, $(CH_2)_qC(O)C_{1-6}$alkyl, $C(O)OC_{1-6}$alkyl, $(CH_2)_qC(O)OC_{1-6}$alkyl, CN, $(CH_2)_qCN$, $NO_2$, $CH_2NO_2$, $NH_2$, $NH(C_{1-6}$alkyl), $N(C_{1-6}$alkyl$)_2$, $(CH_2)_qNH_2$, $(CH_2)_qNH$$(C_{1-6}$alkyl), $(CH_2)_qN(C_{1-6}$alkyl$)_2$; more especially hydrogen, halo, $C_{1-3}$alkyl, $C_{1-3}$haloalkyl, OH, $OC_{1-3}$alkyl, $SC_{1-3}$ alkyl, $CH_2OC_{1-3}$alkyl, $CH_2SC_{1-3}$alkyl, $C(O)C_{1-3}$alkyl, $CH_2C(O)C_{1-3}$alkyl, $C(O)OC_{1-3}$alkyl, $CH_2C(O)OC_{1-3}$alkyl, CN, $CH_2CN$, $NO_2$, $CH_2NO_2$, $NH_2$, $NH(C_{1-6}$alkyl), $N(C_{1-6}$ alkyl$)_2$, $CH_2NH_2$, $CH_2NH(C_{1-6}$alkyl), $CH_2N(C_{1-6}$alkyl$)_2$, $CH_2CH_2NH_2$, $CH_2CH_2NH(C_{1-6}$alkyl), $CH_2CH_2N(C_{1-6}$alkyl$)_2$, CH $CH_2CH_2NH_2$, $CH_2CH_2CH_2NH(C_{1-6}$alkyl), $CH_2CH_2CH_2N(C_{1-6}$alkyl$)_2$, heterocyclyl, $CH_2$heterocyclyl, $CH_2CH_2$heterocyclyl and $CH_2CH_2CH_2$heterocyclyl, even more especially $CH_3$, $CH_2CH_3$, chloro, fluoro, trifluoromethyl, $CO_2CH_3$, $CH_2$morpholine, $CH_2CH_2$morpholine, $CH_2CH_2CH_2$morpholine, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N$$(CH_2CH_3)_2$, $CH_2CH_2CH_2N(CH_2CH_3)_2$, $CH_2$-4-N-methylpiperazine, $CH_2CH_2$-4-N-methylpiperazine, $CH_2CH_2CH_2$-4-N-methylpiperazine, $CH_2$—N-pyrrolidine, $CH_2CH_2$—N-pyrrolidine and $CH_2CH_2CH_2$—N-pyrrolidine;

$R_4$ is selected from the group consisting of hydrogen, $C_{1-6}$alkyl, $C_{1-6}$haloalkyl, $OC_{1-6}$alkyl and $OC_{1-6}$haloalkyl, especially hydrogen, $C_{1-3}$alkyl, $C_{1-3}$haloalkyl, $OC_{1-3}$alkyl and $OC_{1-3}$haloalkyl, more especially $CH_3$, $CF_3$, $OCH_3$ and $OCF_3$;

$R_5$ is selected from hydrogen, $C_{1-6}$alkyl, $C_{1-6}$haloalkyl, $C(O)$$C_{1-6}$alkyl, $S(O)_2C_{1-6}$alkyl, $S(O)_2OC_{1-6}$alkyl, $S(O)_2NH_2$, $S(O)_2NH(C_{1-6}$alkyl) and $S(O)_2N(C_{1-6}$alkyl$)_2$, especially $C_{1-3}$alkyl, $C_{1-3}$haloalkyl, and $C(O)C_{1-3}$alkyl; and $R_6$ is selected from hydrogen and $C_{1-6}$alkyl; especially hydrogen and $C_{1-3}$alkyl; and each $R_7$ is independently selected from the group consisting of hydrogen, alkyl and haloalkyl, especially hydrogen;

m is 0 or an integer 1 to 3, especially where m is 0, 1 or 2;

p is 1, 2 or 3, especially 1 or 2.

In some embodiments, the compound of formula (I) is a compound of formula (II):

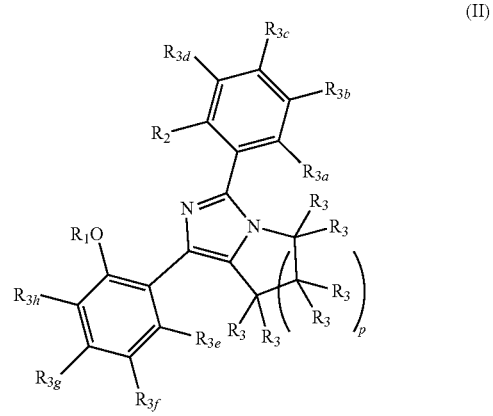

(II)

wherein $R_1$, $R_2$, $R_3$ and p are as defined for formula (I) and $R_{3a}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$ aryl, $(C(R_7)_2)_m$heterocyclyl, $(C(R_7)_2)_m$heteroaryl, $(C(R_7)_2)_m$$OR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)$$R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)$$N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (II) is a compound of formula (IIa):

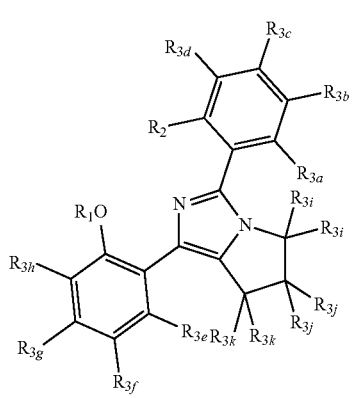

(IIa)

wherein $R_1$ and $R_2$ are as defined for formula (I) and $R_{3a}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (II) is a compound of formula (IIb):

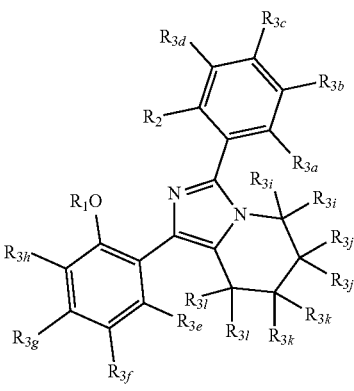

(IIb)

wherein $R_1$ and $R_2$ are as defined for formula (I) and $R_{3a}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (II) is a compound of formula (IIc):

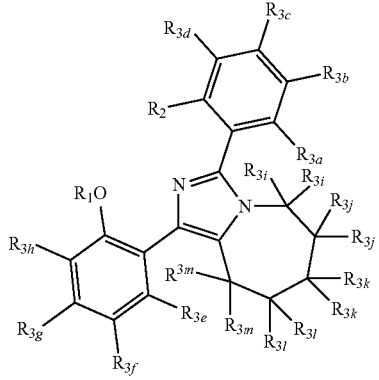

(IIc)

wherein $R_1$ and $R_2$ are as defined for formula (I) and $R_{3a}$ to $R_{3m}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In particular, embodiments of formula (II), one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer from 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_n C_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH;

$R_{3a}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3b}$ is selected from the group consisting of hydrogen, halo, $C_{1-6}$alkyl, $C_{1-6}$haloalkyl and $CO_2C_{1-6}$alkyl, especially hydrogen, fluoro, chloro, $C_{1-3}$alkyl, $C_{1-3}$haloalkyl and $CO_2C_{1-3}$alkyl, more especially hydrogen, fluoro, $CH_3$, $CF_3$ and $CO_2CH_3$;

$R_{3c}$ is selected from the group consisting of hydrogen, halo, $C_{1-6}$alkyl, $C_{1-6}$haloalkyl and $(CH_2)_q$heterocyclyl, especially hydrogen, fluoro, chloro, $C_{1-3}$alkyl, $C_{1-3}$haloalkyl and $CH_2$heterocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_q N(C_{1-6}$alkyl$)_2$ and $(CH_2)_q$ heterocyclyl, where q is 1 to 3, especially hydrogen, fluoro, chloro, $C_{1-3}$alkyl, $C_{1-3}$haloalkyl, $(CH_2)_qN(C_{1-3}alkyl)_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2$morpholine, $CH_2CH_2$morpholine, $CH_2CH_2CH_2$morpholine, $CH_2$piperazine, $CH_2CH_2$piperazine, $CH_2CH_2CH_2$piperazine, $CH_2$-4-N-methylpiperazine, $CH_2CH_2$-4-N-methylpiperazine, $CH_2CH_2CH_2$-4-N-methylpiperazine, $CH_2$pyrrolidine, $CH_2CH_2$pyrrolidine and $CH_2CH_2CH_2$pyrrolidine;

$R_{3e}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3f}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CF_3$ and $CH_3$;

$R_{3g}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

$R_{3h}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;

p is 1, 2 or 3;

or a pharmaceutically acceptable salt, stereoisomer or solvate thereof.

Particular compounds of formula (II) are compounds 7, 8, 9, 10, 12, 36, 37 and 38 as shown in the examples.

In some embodiments, the compound of formula (I) is a compound of formula (III):

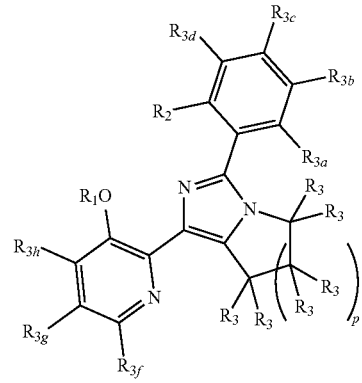

(III)

wherein $R_1$, $R_2$ and $R_3$ and p are as defined for formula (I) and $R_{3a}$ to $R_{3d}$ and $R_{3f}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (III) is a compound of formula (IIIa):

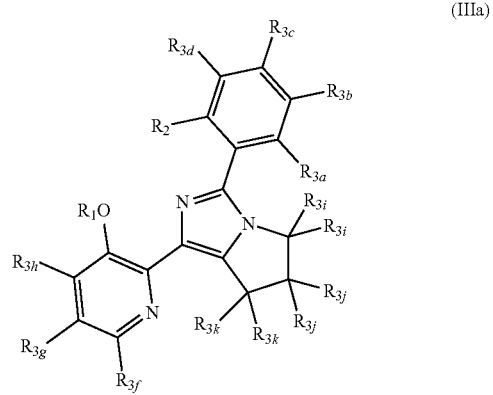

(IIIa)

wherein $R_1$ and $R_2$ are as defined for formula (I) and $R_{3a}$ to $R_{3d}$ and $R_{3f}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In some embodiments, the compound of formula (III) is a compound of formula (IIIb):

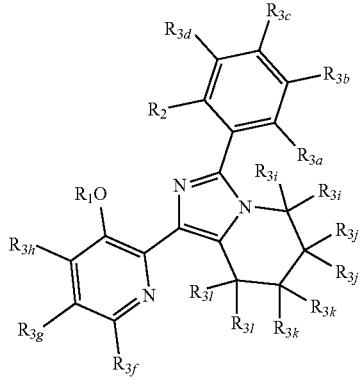

(IIIb)

wherein $R_1$ and $R_2$ are as defined for formula (I) and $R_{3a}$ to $R_{3d}$ and $R_{3f}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6) C(O)N(R_6)_2$ and $(C(R_7)_2)_m N(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In some embodiments, the compound of formula (III) is a compound of formula (IIIc):

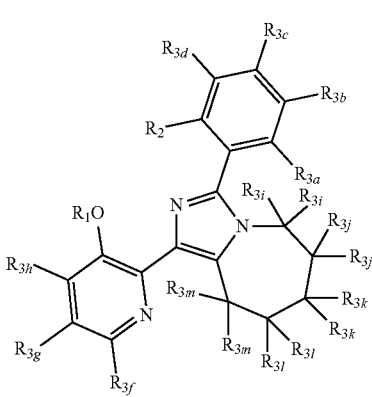

(IIIc)

wherein $R_1$ and $R_2$ are as defined for formula (I) and $R_{3a}$ to $R_{3d}$ and $R_{3f}$ to $R_{3m}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6) C(O)N(R_6)_2$ and $(C(R_7)_2)_m N(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In particular embodiments of formula (III), one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer of 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_n C_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH;

$R_{3a}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3b}$ is selected from the group consisting of hydrogen, halo, $C_{1-6}$alkyl, $C_{1-6}$haloalkyl and $CO_2C_{1-6}$alkyl, especially hydrogen, fluoro, chloro, $C_{1-3}$alkyl, $C_{1-3}$haloalkyl and $CO_2C_{1-3}$alkyl, more especially hydrogen, fluoro, $CH_3$, $CF_3$ and $CO_2CH_3$;

$R_{3c}$ is selected from the group consisting of hydrogen, halo, $C_{1-6}$alkyl, $C_{1-6}$haloalkyl and $(CH_2)_q$heterocyclyl wherein q is an integer of 1 to 3, especially hydrogen, fluoro, chloro, $C_{1-3}$alkyl, $C_{1-3}$haloalkyl and $CH_2$heterocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_q N(C_{1-6}$alkyl$)_2$ and $(CH_2)_q$heterocyclyl, where q is 1 to 3, especially hydrogen, fluoro, chloro, $C_{1-3}$alkyl, $C_{1-3}$haloalkyl, $(CH_2)_q N(C_{1-3}$alkyl$)_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2$morpholine, $CH_2CH_2$morpholine, $CH_2CH_2CH_2$morpholine, $CH_2$piperazine, $CH_2CH_2$piperazine, $CH_2CH_2CH_2$piperazine, $CH_2$-4-N-methylpiperazine, $CH_2CH_2$-4-N-methylpiperazine, $CH_2CH_2CH_2$-4-N-methylpiperazine, $CH_2$pyrrolidine, $CH_2CH_2$pyrrolidine and $CH_2CH_2CH_2$pyrrolidine;

$R_{3f}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CF_3$ and $CH_3$;

$R_{3g}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

$R_{3h}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;

p is 1, 2 or 3;

or a pharmaceutically acceptable salt, stereoisomer or solvate thereof.

Particular compounds of formula (III) are compounds 1, 2, 3, 4, 5, 6, 40, 41, 42, 43, 45, 46, 47, 48, 50, 51, 52, 53, 55, 56, 57, 58 and 59 as shown in the examples.

In some embodiments, the compound of formula (I) is a compound of formula (IV):

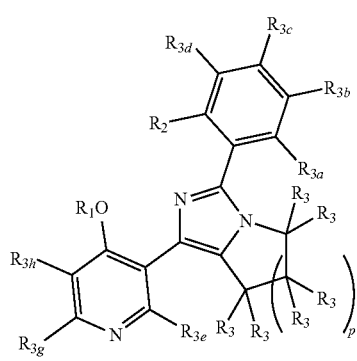

(IV)

wherein $R_1$, $R_2$ and $R_3$ and p are as defined for formula (I) and $R_{3a}$ to $R_{3e}$ and $R_{3g}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6) C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (IV) is a compound of formula (IVa):

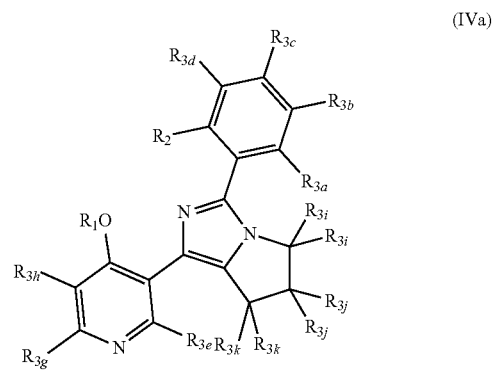

(IVa)

wherein $R_1$ and $R_2$ are as defined for formula (I) and $R_{3a}$ to $R_{3e}$ and $R_{3g}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6) C(O)N(R_6)_2$ and $(C(R_7)_2)_m N(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In some embodiments, the compound of formula (IV) is a compound of formula (IVb):

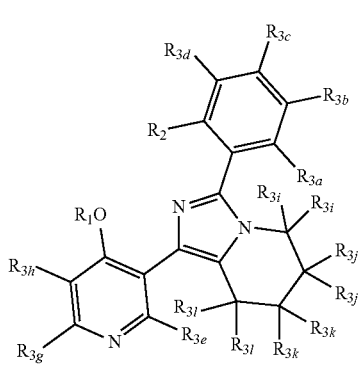

(IVb)

wherein $R_1$ and $R_2$ are as defined for formula (I) and $R_{3a}$ to $R_{3e}$ and $R_{3g}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6) C(O)N(R_6)_2$ and $(C(R_7)_2)_m N(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In some embodiments, the compound of formula (IV) is a compound of formula (IVc):

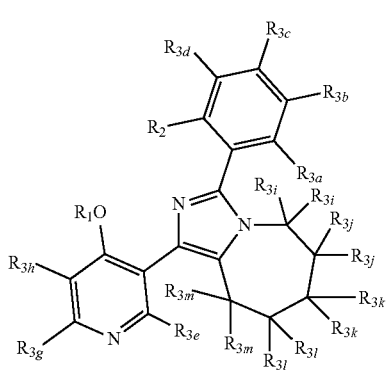

(IVc)

wherein $R_1$ and $R_2$ are as defined for formula (I) and $R_{3a}$ to $R_{3e}$ and $R_{3g}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I); or a pharmaceutically acceptable salt, stereoisomer or solvate thereof.

In particular embodiments of formula (IV), one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer of 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl)$_2$ and $OS(O)_n C_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH;

$R_{3a}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3b}$ is selected from the group consisting of hydrogen, halo, $C_{1-6}$alkyl, $C_{1-6}$haloalkyl and $CO_2C_{1-6}$alkyl, especially hydrogen, fluoro, chloro, $C_{1-3}$alkyl, $C_{1-3}$haloalkyl and $CO_2C_{1-3}$alkyl, more especially hydrogen, fluoro, $CH_3$, $CF_3$ and $CO_2CH_3$;

$R_{3c}$ is selected from the group consisting of hydrogen, halo, $C_{1-6}$alkyl, $C_{1-6}$haloalkyl and $(CH_2)_q$heteocyclyl where q is an integer of 1 to 3, especially hydrogen, fluoro, chloro, $C_{1-3}$alkyl, $C_{1-3}$haloalkyl and $CH_2$heteocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_q N(C_{1-6}$alkyl)$_2$ and $(CH_2)_q$heterocyclyl, where q is 1 to 3, especially hydrogen, fluoro, chloro, $C_{1-3}$alkyl, $C_{1-3}$haloalkyl, $(CH_2)_q N(C_{1-3}$alkyl)$_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2$morpholine, $CH_2CH_2$morpholine, $CH_2CH_2CH_2$morpholine, $CH_2$piperazine, $CH_2CH_2$piperazine, $CH_2CH_2CH_2$piperazine, $CH_2$-4-N-methylpiperazine, $CH_2CH_2$-4-N-methylpiperazine, $CH_2CH_2CH_2$-4-N-methylpiperazine, $CH_2$pyrrolidine, $CH_2CH_2$pyrrolidine and $CH_2CH_2CH_2$pyrrolidine;

$R_{3e}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3g}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

$R_{3h}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen$C_{1-3}$alkyl and $C_{1-3}$haloalkyl, more especially hydrogen, $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;
p is 1, 2 or 3;
or a pharmaceutically acceptable salt, stereoisomer or solvate thereof.

Particular compounds of formula (IV) are compounds 29 and 30 as shown in the examples.

In some embodiments, the compound of formula (I) is a compound of formula (V):

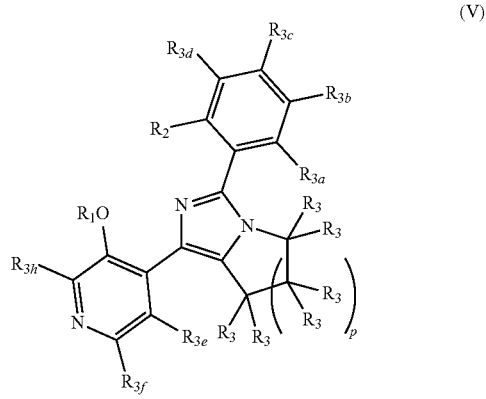

(V)

wherein $R_1$, $R_2$, $R_3$ and p are as defined for formula (I) and $R_{3a}$ to $R_{3f}$ and $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof.

In some embodiments, the compound of formula (V) is a compound of formula (Va):

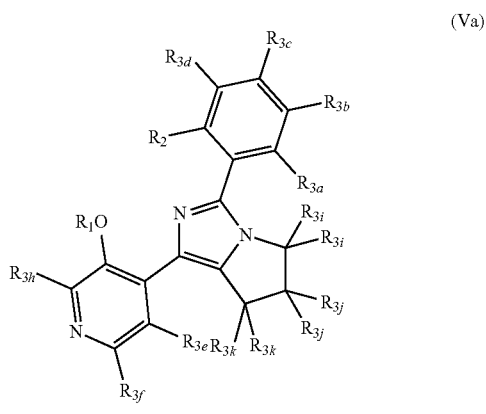

(Va)

wherein $R_1$ and $R_2$ are as defined for formula (I) and $R_{3a}$ to $R_{3f}$ and $R_{3h}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof.

In some embodiments, the compound of formula (V) is a compound of formula (Vb):

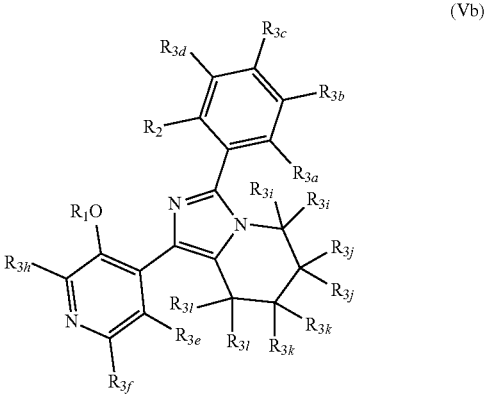

(Vb)

wherein $R_1$ and $R_2$ are as defined for formula (I) and $R_{3a}$ to $R_{3f}$ and $R_{3h}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof.

In some embodiments, the compound of formula (V) is a compound of formula (Vc):

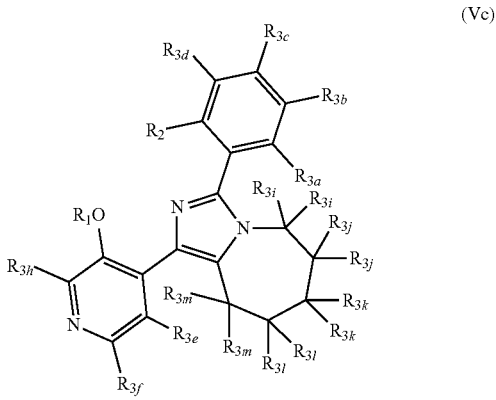

(Vc)

wherein $R_1$ and $R_2$ are as defined for formula (I) and $R_{3a}$ to $R_{3f}$ and $R_{3h}$ to $R_{3m}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof. In particular embodiments of formula (V), one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer of 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl)$_2$ and $OS(O)_nC_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH;

$R_{3a}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3b}$ is selected from the group consisting of hydrogen, halo, $C_{1-6}$alkyl, $C_{1-6}$haloalkyl and $CO_2C_{1-6}$alkyl, especially hydrogen, fluoro, chloro, $C_{1-3}$alkyl, $C_{1-3}$haloalkyl and $CO_2C_{1-3}$alkyl, more especially hydrogen, fluoro, $CH_3$, $CF_3$ and $CO_2CH_3$;

$R_{3c}$ is selected from the group consisting of hydrogen, halo, $C_{1-6}$alkyl, $C_{1-6}$haloalkyl and $(CH_2)_q$heterocyclyl wherein q is an integer of 1 to 3, especially hydrogen, fluoro, chloro, $C_{1-3}$alkyl, $C_{1-3}$haloalkyl and $(CH_2)_q$heterocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_qN(C_{1-6}$alkyl$)_2$ and $(CH_2)_q$heterocyclyl, where q is 1 to 3, especially hydrogen, fluoro, chloro, $C_{1-3}$alkyl, $C_{1-3}$haloalkyl, $(CH_2)_qN(C_{1-3}$alkyl$)_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2$morpholine, $CH_2CH_2$morpholine, $CH_2CH_2CH_2$morpholine, $CH_2$piperazine, $CH_2CH_2$piperazine, $CH_2CH_2CH_2$piperazine, $CH_2$-4-N-methylpiperazine, $CH_2CH_2$-4-N-methylpiperazine, $CH_2CH_2CH_2$-4-N-methylpiperazine, $CH_2$pyrrolidine, $CH_2CH_2$pyrrolidine and $CH_2CH_2CH_2$pyrrolidine;

$R_{3e}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3f}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CF_3$ and $CH_3$;

$R_{3h}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;

p is 1, 2 or 3;

or a pharmaceutically acceptable salt, stereoisomer or solvate thereof. Particular compounds of formula (V) are compounds 21, 22, 23, 24, 25, 26, 27 and 28 as shown in the examples.

In some embodiments, the compound of formula (I) is a compound of formula (VI):

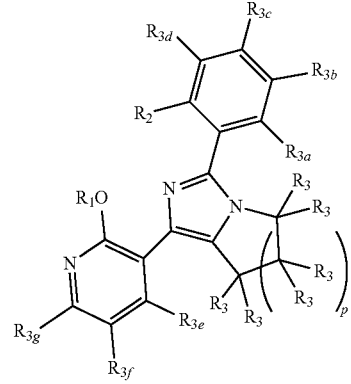

(VI)

wherein $R_1$, $R_2$, $R_3$ and p are as defined for formula (I) and $R_{3a}$ to $R_{3g}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VI) is a compound of formula (VIa):

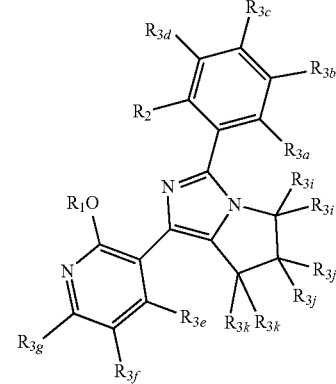

(VIa)

wherein $R_1$ and $R_2$ are as defined for formula (I) and $R_{3a}$ to $R_{3g}$ and $R_{3i}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m$OR$_5$, $(C(R_7)_2)_m$SR$_5$, $(C(R_7)_2)_m$C(O)R$_4$, $(C(R_7)_2)_m$C(S)R$_4$, $(C(R_7)_2)_m$OC(O)R$_4$, $(C(R_7)_2)_m$SC(S)R$_4$, $(C(R_7)_2)_m$OC(S)R$_4$, $(C(R_7)_2)_m$SC(O)R$_4$, $(C(R_7)_2)_m$CN, $(C(R_7)_2)_m$NO$_2$, $(C(R_7)_2)_m$N(R$_6$)$_2$, $(C(R_7)_2)_m$S(O)$_n$R$_4$, $(C(R_7)_2)_m$N(R$_6$)C(O)N(R$_6$)$_2$ and $(C(R_7)_2)_m$N(R$_6$)C(S)N(R$_6$)$_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VI) is a compound of formula (VIb):

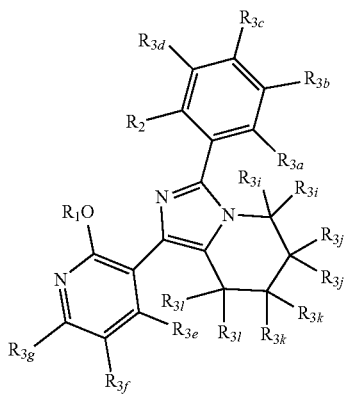

(VIb)

wherein $R_1$ and $R_2$ are as defined for formula (I) and $R_{3a}$ to $R_{3g}$ and $R_{3i}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VI) is a compound of formula (VIc):

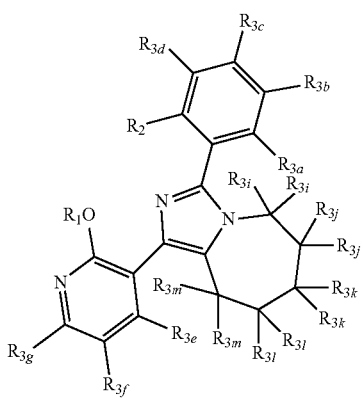

(VIc)

wherein $R_1$ and $R_2$ are as defined for formula (I) and $R_{3a}$ to $R_{3g}$ and $R_{3i}$ to $R_{3m}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In particular embodiments of formula (VI), one or more of the following applies:

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl where q is an integer of 1 to 3; especially, hydrogen, $C_{1-6}$alkyl, $CH_2$aryl and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2 NH_2$, $OS(O)_2 NH(C_{1-6}$alkyl), $OS(O)_2 N(C_{1-6}$alkyl$)_2$ and $OS(O)_n C_{1-6}$alkyl; especially hydrogen, OH, halo, CN, $NO_2$, $OC_{1-6}$alkyl and $CO_2 C_{1-6}$alkyl; more especially hydrogen, OH, halo, CN, $NO_2$, $OC_{1-6}$alkyl and $CO_2 C_{1-6}$alkyl; even more especially hydrogen, OH, halo, CN, $NO_2$, $OCH_3$ and $CO_2 CH_3$; most especially OH;

$R_{3a}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3b}$ is selected from the group consisting of hydrogen, halo, $C_{1-6}$alkyl, $C_{1-6}$haloalkyl and $CO_2 C_{1-6}$alkyl, especially hydrogen, fluoro, chloro, $C_{1-3}$alkyl, $C_{1-3}$haloalkyl and $CO_2 C_{1-3}$alkyl, more especially hydrogen, fluoro, $CH_3$, $CF_3$ and $CO_2 CH_3$;

$R_{3c}$ is selected from the group consisting of hydrogen, halo, $C_{1-6}$alkyl, $C_{1-6}$haloalkyl and $(CH_2)_q$heterocyclyl wherein q is an integer of 1 to 3, especially hydrogen, fluoro, chloro, $C_{1-3}$alkyl, $C_{1-3}$haloalkyl and $CH_2$heterocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_q N(C_{1-6}$alkyl$)_2$ and $(CH_2)_q$heterocyclyl, where q is 1 to 3, especially hydrogen, fluoro, chloro, $C_{1-3}$alkyl, $C_{1-3}$haloalkyl, $(CH_2)_q N(C_{1-3}$alkyl$)_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2 N(CH_3)_2$, $CH_2 CH_2 N(CH_3)_2$, $CH_2 CH_2 CH_2 N(CH_3)_2$ $CH_2 N(CH_2 CH_3)_2$, $CH_2 CH_2 N(CH_2 CH_3)_2$, $CH_2 CH_2 CH_2 N(CH_2 CH_3)_2$, $CH_2$morpholine, $CH_2 CH_2$morpholine, $CH_2 CH_2 CH_2$morpholine, $CH_2$piperazine, $CH_2 CH_2$piperazine, $CH_2 CH_2 CH_2$piperazine, $CH_2$-4-N-methylpiperazine, $CH_2 CH_2$-4-N-methylpiperazine, $CH_2 CH_2 CH_2$-4-N-methylpiperazine, $CH_2$pyrrolidine, $CH_2 CH_2$pyrrolidine and $CH_2 CH_2 CH_2$pyrrolidine;

$R_{3e}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3f}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CF_3$ and $CH_3$;

$R_{3g}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;

p is 1, 2 or 3;

or a pharmaceutically acceptable salt, stereoisomer or solvate thereof.

Particular compounds of formula (VI) are compounds 13, 14, 15, 16, 17, 18, 19, 20 and 39 as shown in the examples.

In some embodiments, the compound of formula (I) is a compound of formula (VII):

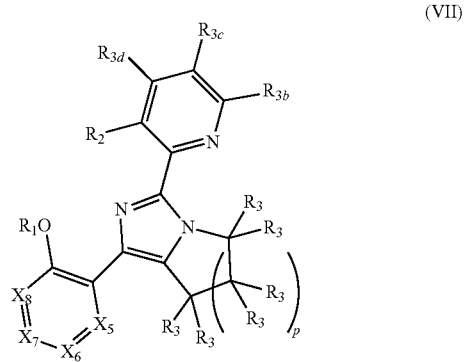

(VII)

wherein $R_1$, $R_2$, $R_3$ and p are as defined for formula (I), $X_5$ is N or $CR_{3e}$, $X_6$ is N or $CR_{3f}$, $X_7$ is N or $CR_{3g}$, $X_8$ is N or $CR_{3h}$ and $R_{3b}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VII) is a compound of formula (VIIa):

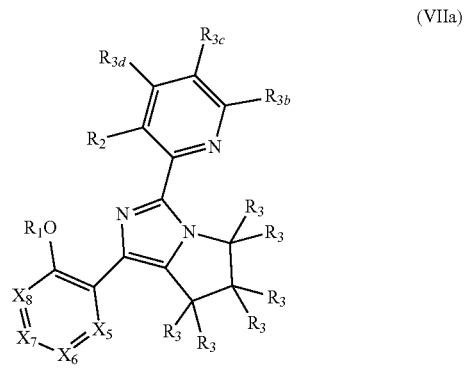

(VIIa)

wherein $R_1$ and $R_2$ are as defined for formula (I), $X_5$ is N or $CR_{3e}$, $X_6$ is N or $CR_{3f}$, $X_7$ is N or $R_{3g}$, $X_8$ is N or $CR_{3h}$ and $R_{3b}$ to $R_{3k}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VII) is a compound of formula (VIIb):

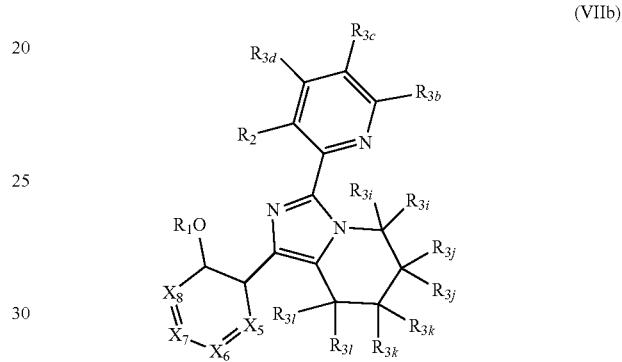

(VIIb)

wherein $R_1$ and $R_2$ are as defined for formula (I), $X_5$ is N or $CR_{3e}$, $X_6$ is N or $CR_{3f}$, $X_7$ is N or $R_{3g}$, $X_8$ is N or $CR_{3h}$ and $R_{3b}$ to $R_{3l}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In some embodiments, the compound of formula (VII) is a compound of formula (VIIc):

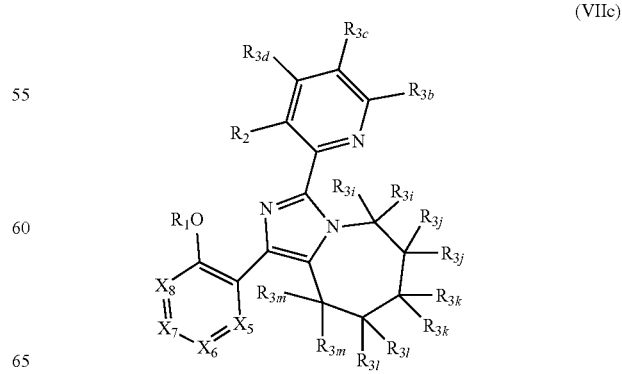

(VIIc)

wherein $R_1$ and $R_2$ are as defined for formula (I), $X_5$ is N or $CR_{3e}$, $X_6$ is N or $CR_{3f}$, $X_7$ is N or $R_{3g}$, $X_8$ is N or $CR_{3h}$ and $R_{3b}$ to $R_{3m}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

In particular embodiments of formula (VII), one or more of the following applies:

$X_5$ is $CR_{3e}$, $X_6$ is $CR_{3f}$, $X_7$ is $CR_{3g}$ and $X_8$ is $CR_{3g}$;

One of $X_5$, $X_6$, $X_7$ and $X_8$ is N;

$R_1$ is selected from the group consisting of hydrogen, $C_{1-6}$alkyl, $C_{2-6}$alkenyl, aryl, $(CH_2)_q$aryl, $C(O)C_{1-6}$alkyl and $C(O)OC_{1-6}$alkyl wherein q is an integer of 1 to 3; especially, hydrogen, $C_{1-6}$alkyl, $CH_2$aryl, and $C(O)C_{1-6}$alkyl, more especially hydrogen, $C_{1-3}$alkyl and $CH_2$phenyl, most especially hydrogen, $CH_3$ and $CH_2$phenyl;

$R_2$ is selected from the group consisting of hydrogen, OH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl$)_2$ and $OS(O)_n C_{1-6}$alkyl; especially hydrogen, OH, halo, CN, $NO_2$, $OC_{1-6}$alkyl and $CO_2C_{1-6}$alkyl; more especially hydrogen, OH, halo, CN, $NO_2$, $OC_{1-6}$alkyl and $CO_2C_{1-6}$alkyl; even more especially hydrogen, OH, halo, CN, $NO_2$, $OCH_3$ and $CO_2CH_3$; most especially OH;

$R_{3b}$ is selected from the group consisting of hydrogen, halo, $C_{1-6}$alkyl, $C_{1-6}$haloalkyl and $CO_2C_{1-6}$alkyl, especially hydrogen, fluoro, chloro, $C_{1-3}$alkyl, $C_{1-3}$haloalkyl and $CO_2C_{1-3}$alkyl, more especially hydrogen, fluoro, $CH_3$, $CF_3$ and $CO_2CH_3$;

$R_{3c}$ is selected from the group consisting of hydrogen, halo, $C_{1-6}$alkyl, $C_{1-6}$haloalkyl and $(CH_2)_q$heterocyclyl wherein q is an integer of 1 to 3, especially hydrogen, fluoro, chloro, $C_{1-3}$alkyl, $C_{1-3}$haloalkyl and $CH_2$heterocyclyl, more especially hydrogen, $CH_3$, $CF_3$, fluoro and $CH_2$morpholine;

$R_{3d}$ is selected from the group consisting of hydrogen, halo, $C_{1-6}$alkyl, $C_{1-6}$haloalkyl, $(CH_2)_q N(C_{1-6}$alkyl$)_2$ and $(CH_2)_q$heterocyclyl, where q is 1 to 3, especially hydrogen, fluoro, chloro, $C_{1-3}$alkyl, $C_{1-3}$haloalkyl, $(CH_2)_q N(C_{1-3}$alkyl$)_2$, $(CH_2)_q$morpholine, $(CH_2)_q$piperazine, $(CH_2)_q$-4-N-methylpiperazine and $(CH_2)_q$pyrrolidine, where q is 1 to 3, more especially hydrogen, fluoro, chloro, $CH_3$, $CF_3$, $CH_2N(CH_3)_2$, $CH_2CH_2N(CH_3)_2$, $CH_2CH_2CH_2N(CH_3)_2$, $CH_2N(CH_2CH_3)_2$, $CH_2CH_2N(CH_2CH_3)_2$, $CH_2CH_2CH_2N(CH_2CH_3)_2$, $CH_2$morpholine, $CH_2CH_2$morpholine, $CH_2CH_2CH_2$morpholine, $CH_2$piperazine, $CH_2CH_2$piperazine, $CH_2CH_2CH_2$piperazine, $CH_2$-4-N-methylpiperazine, $CH_2CH_2$-4-N-methylpiperazine, $CH_2CH_2CH_2$-4-N-methylpiperazine, $CH_2$pyrrolidine, $CH_2CH_2$pyrrolidine and $CH_2CH_2CH_2$pyrrolidine;

$R_{3e}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen and fluoro;

$R_{3f}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CF_3$ and $CH_3$;

$R_{3g}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

$R_{3h}$ is selected from the group consisting of hydrogen, halo, $C_{1-6}$alkyl and $C_{1-6}$haloalkyl, especially hydrogen, fluoro, chloro, $C_{1-3}$alkyl and $C_{1-3}$haloalkyl, more especially hydrogen, fluoro, $CH_3$ and $CF_3$;

Each $R_{3i}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3j}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3k}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3l}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

Each $R_{3m}$ is independently selected from the group consisting of hydrogen, $C_{1-6}$alkyl and $C_{1-6}$haloalkyl, especially hydrogen, $C_{1-3}$alkyl and $C_{1-3}$haloalkyl, more especially hydrogen, $CH_3$ and $CF_3$;

m is 0 or an integer 1 to 3, especially where m is 0, 1 or 2;

p is 1, 2 or 3;

or a pharmaceutically acceptable salt, stereoisomer or solvate thereof.

Particular compounds of formula (VII) are compounds 11, 44, 49 and 54 as shown in the examples.

The compounds of formula (I) may be made by methods known in the art. For example, Scheme 1 shows the preparation of key Intermediates I to II. Representative methodology for Method A is described in Tao X. et al. J. Org. Chem. 2012, 77, pp 612-616, Method B in Azzouz, R. et al. Synlett, 2006, 12, pp 1908-1912 and Method C in Deane K. J. et al., ACS Med. Chem. Lett., 2014, 5, pp 576-581 and Shi J. et al. ACS Omega, 2017, 2, 3406-3416. The general transformations Methods D, E and G shown in Schemes 1-3 are well known and have been described generally in references such as Protective Groups in Organic Synthesis, Green T. W. and Wuts P. G. M. John Wiley & Sons, New York, 1999 and Comprehensive Organic Transformations: A Guide to Functional Group Preparations, Larock, R. C. John Wiley & Sons, New York, 2018. Scheme 2 outlines the transformation of the key intermediate I/II to the compound of formula (I) and scheme 3 outlines the preparation of intermediates III-IV and their subsequent conversion to compounds of formula (I). Additional representative methodology is again described in the literature where Method F is widely described and exemplified by the work of Wu, J. et al. Chem. Commun., 2010, 46, pp 3687-3689, Method H employs the methods generally described by Beak P. et al. J. Org. Chem. 1993, 58, pp 1109-1117 or Barker G. et al. Org. Lett. 2010, 12, pp 4176-4179.

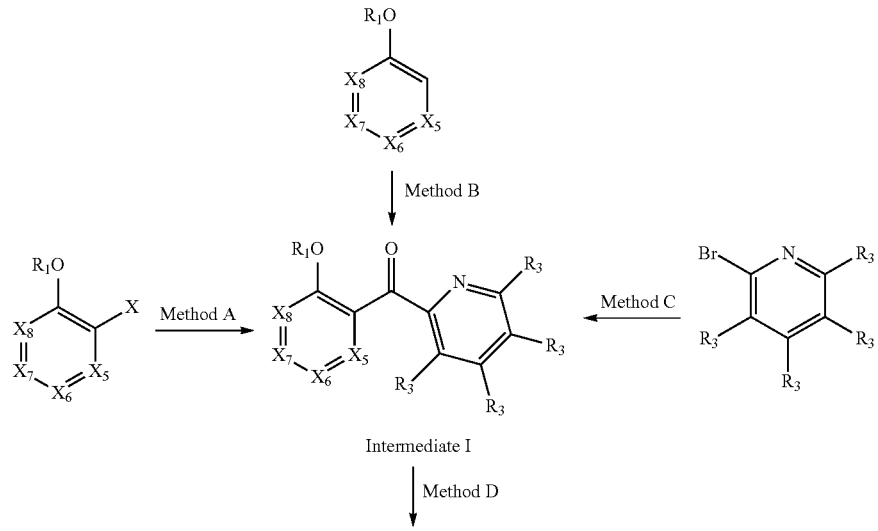

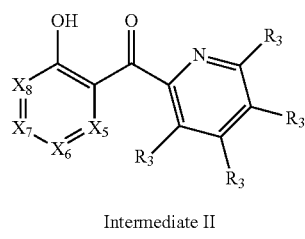

Scheme 2
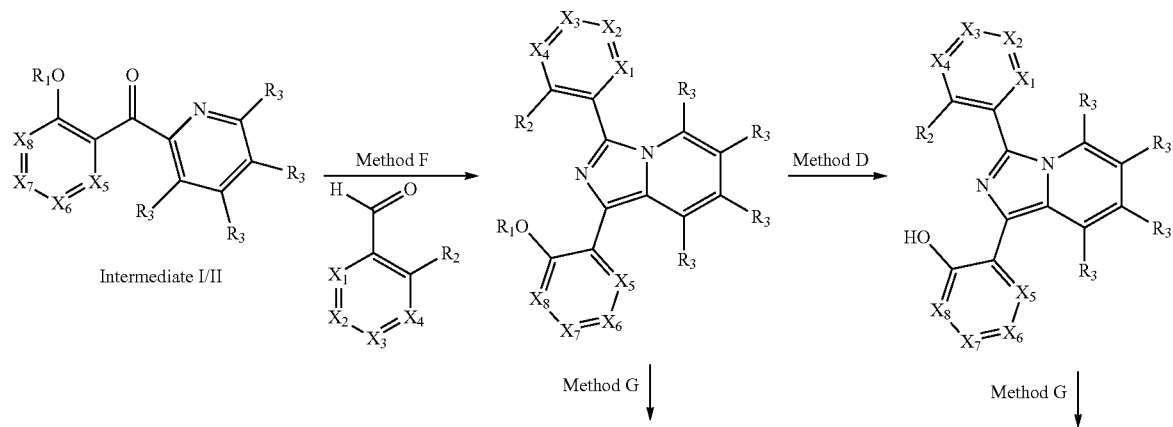
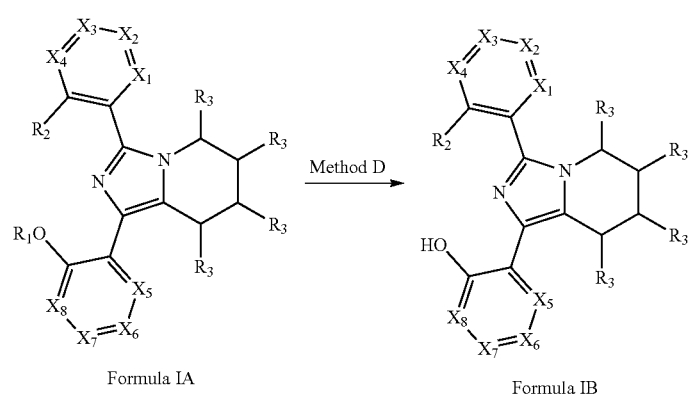
Formula IA
Formula IB

Scheme 3

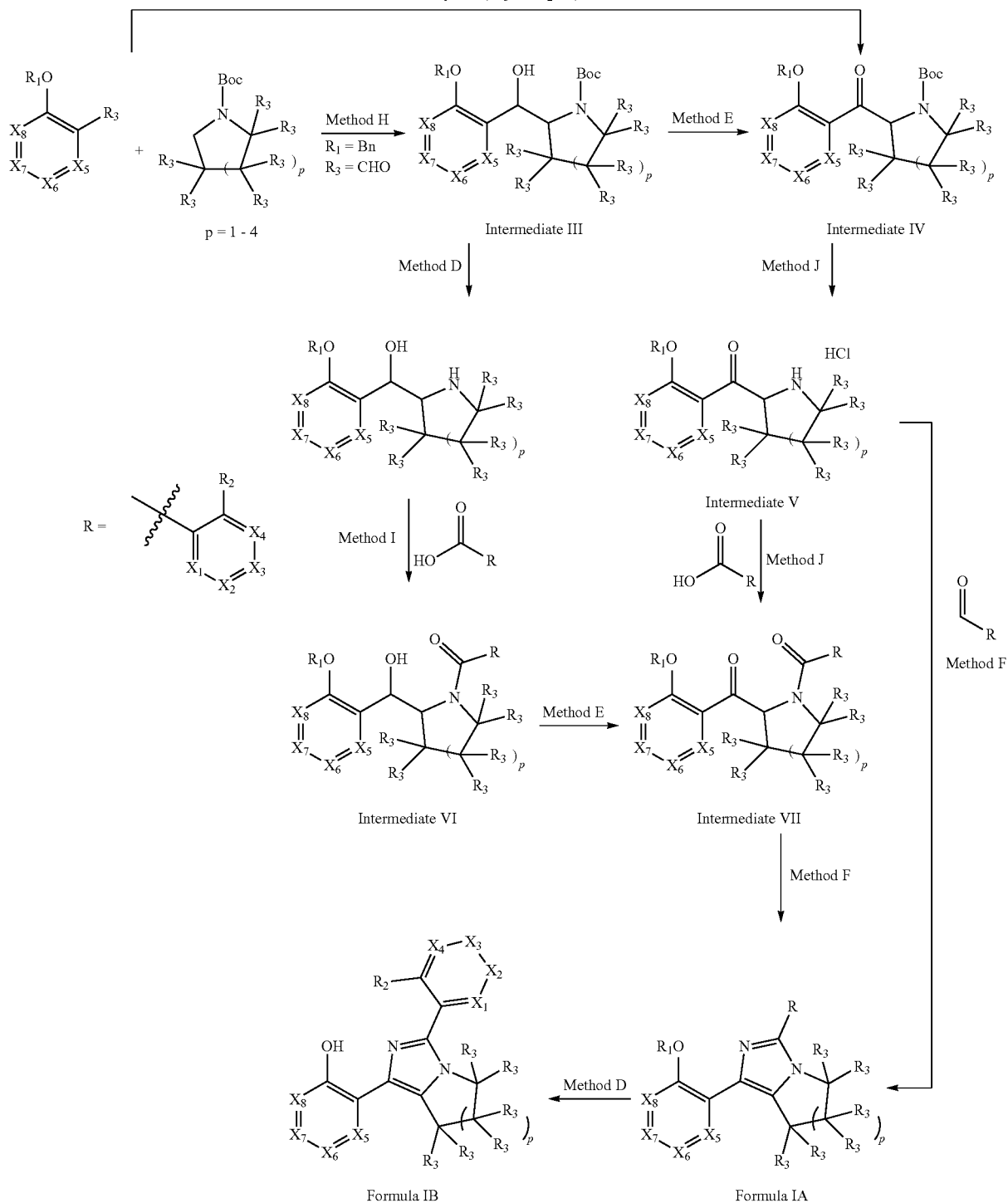

Methods of the Invention

For the treatment of metal-associated neurological disorders such as Parkinson's disease, it is highly desirable to find iron modulators. It has now been found in accordance with the present invention that certain iron modulators are capable of removing iron from cells, thus making them suitable candidates for treatment of Parkinson's disease and other metal associated neurological disorders.

In one aspect of the invention there is provided a method of treating or preventing a metal ion associated disorder comprising administering to a subject a compound of formula (I) or a pharmaceutically acceptable salt or solvate thereof. In a particular embodiment, the disorder is a neurological disorder.

In a further aspect of the invention, there is provided a compound of formula (I) or a pharmaceutically acceptable salt or solvate thereof for use in treating or preventing a metal ion associated neurological disorder. In a particular embodiment, the disorder is a neurological disorder.

In yet a further aspect of the invention, there is provided a use of a compound of formula (I) or a pharmaceutically acceptable salt or solvate thereof in the manufacture of a medicament for treating or preventing a metal ion associated disorder. In a particular embodiment, the disorder is a neurological disorder.

Excess iron in vital organs increases the risk of many diseases, liver disease (cancer, cirrhosis), heart attack or heart failure, cardiotoxicity, diabetes mellitus, osteoarthritis, osteoporosis, metabolic syndrome, hypothyroidism, hypogonadism and is associated with onset of or acceleration of neurodegenerative diseases such as Alzheimer's disease, Parkinson's disease, Huntington's disease, epilepsy and multiple sclerosis.

In particular embodiment, the metal associated neurological disease is Parkinson's disease, Alzheimers disease, Huntington's disease, amylotrophic lateral sclerosis (ALS), fronto temporal dementia (FTD), multiple system atrophy (MSA), tardive dyskinesia (TD), Hallervorden-Spatz syndrome, Friedreich's ataxia, epilepsy and multiple sclerosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individuals to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 μg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include amelioration or alleviation of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body. Other therapies may include: a MAO-B inhibitor such as selegiline, rasagiline, lazabemide, and caroxazone; a dopamine agonist such as bromocriptine, cabergoline, lisuride, pergolide; levodopa; carbidopa; inirole; apomorphine, sumanirole; rotigotine; talipexole; dihydroergocriptine or; a catechol-O-methyltransferase inhibitor such as tolcapone or entacapone. Further therapies may also include those administered for ALS, such as Riluzole or Edaravone.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt, stereoisomer or solvate thereof and at least one pharmaceutically acceptable carrier.

The carrier(s) and/or excipients must be "acceptable" in the sense of being compatible with the other ingredients of the composition and not deleterious to the recipient thereof.

Pharmaceutical formulations include those suitable for oral, rectal, nasal, topical (including buccal and sub-lingual) or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to 1000 milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "composition" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized moulds, allowed to cool, and thereby to solidity.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a hydrofluoroalkane (HFA) or chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 50 microns or less. Such a particle size may be obtained by means known in the art, for example by micronization.

When desired, formulations adapted to give sustained release of the active ingredient may be employed.

The pharmaceutical compositions are preferably in unit dosage forms. In such form, the composition is subdivided into unit doses containing appropriate quantities of the active component. The unit dosage form can be a packaged composition, the package containing discrete quantities of composition, such as packeted tablets, capsules, and powders in vials or ampoules. Also, the unit dosage form can be a capsule, tablet, cachet, or lozenge itself, or it can be the appropriate number of any of these in packaged form.

The invention will now be described with reference to the following Examples which illustrate some preferred aspects of the present invention. However, it is to be understood that the particularity of the following description of the invention is not to supersede the generality of the preceding description of the invention.

EXAMPLES

| Abbreviations | |
|---|---|
| ACN | acetonitrile |
| AcOH | acetic acid |
| Boc | tert-butyloxycarbonyl |
| Bn | benzyl |
| CDI | carbonyl diimidazole |
| Conc. | concentrated |
| CV | column volume/s |
| DCM | dichloromethane |
| DMSO | dimethylsulfoxide |
| DMP | Dess-Martin periodinane |
| eq | equivalent/s |
| $Et_2O$ | diethylether |
| EtOAc | ethyl acetate |
| EtOH | ethanol |
| h | hour/s |
| HBSS | Hanks' balanced salt solution |
| HPLC | high performance liquid chromatography |
| i-PrOH | isopropanol |
| KOAc | potassium acetate |
| MeOH | methanol |
| min | minute/s |
| ms | mass spectrometry |
| $NH_4OAc$ | ammonium acetate |
| n-BuLi | n-butyl lithium |
| O/N | overnight |
| RBF | round bottom flask |
| RT | room temperature |
| sat. | saturated |
| sec-BuLi | sec-butyl lithium |
| TFA | trifluoroacetic acid |
| THF | tetrahydrofuran |
| TMEDA | tetramethylethylene diamine |
| $t_R$ | retention time |
| TMSOTf | trimethylsilyl trifluoromethanesulfonate |

HPLC

HPLC was carried out using Column: Alltech Hypersil BDS C18 5 µm, 4.6 mm×150 mm using water/ACN eluents with both containing 0.1% TFA. Two gradient methods were employed specified as HPLC1 or HPLC2 and detailed in the protocols below.

| HPLC1 gradient protocol | | | HPLC2 gradient protocol | | | |
|---|---|---|---|---|---|---|
| Time | 0.1% TFA in $H_2O$ | 0.1% TFA in ACN | Flow (mL/min) | Time | 0.1% TFA in $H_2O$ | 0.1% TFA in ACN | Flow (mL/min) |
| 0 | 95 | 5 | 1.0 | 0 | 100 | 0 | 1.0 |
| 0.5 | 95 | 5 | 1.0 | 20 | 0 | 100 | 1.0 |
| 6.5 | 0 | 100 | 1.0 | 21 | 0 | 100 | 1.0 |
| 7.5 | 0 | 100 | 1.0 | 21.1 | 100 | 0 | 1.0 |
| 8.0 | 95 | 5 | 1.0 | 25 | 100 | 0 | 1.0 |
| 12 | 95 | 5 | 1.0 | | | | |

The following generalised methods were used to prepare compounds of Intermediates I to VII and compounds of Formula I as referred to in Schemes 1, 2 and 3.

Method A i) Grignard: Magnesium (1.1 eq) was placed into a RBF and just covered with THF before a crystal of iodine was added followed by a small portion of the neat bromoanisole. The mixture was alternatively sonicated and heated until the Grignard formation initiated. Once initiated, the remaining bromoanisole in THF was added and the resultant mixture heated to reflux for 0.5 h. The Grignard solution was cooled to 0° C. before the appropriate nitrile, ester or amide (0.9 eq) in THF was added dropwise before quenching either after 1-2 h or after storing at 4° C. overnight. The reaction was quenched with sat. $NH_4Cl_{(aq)}$ and extracted with DCM. The combined organic extracts were dried and concentrated under reduced pressure to afford the crude ketone. Where a nitrile was used, the isolated imine intermediate was suspended/dissolved in ether and conc. HCl (3:1). The mixture was stirred for 0.5 h then neutralised using 2M $NaOH_{(aq)}$ before extraction with EtOAc. The combined organic extracts were dried ($Na_2SO_4$) and concentrated under reduced pressure to afford the crude ketone. The crude ketone was used as is or purified by crystallisation or flash chromatography.

ii) Organolithium: An aryl iodide (1-2 eq) in $Et_2O$ or THF was cooled to ~−70° C. before n-BuLi in hexanes was slowly added to the mixture keeping the temperature below −65° C. The resultant solution was stirred for 15 min before the nitrile, ester or amide (1-2 eq) in $Et_2O$ or THF was added. The reaction was either kept cool or, in the case of nitriles, allowed to warm to −10° C. over 2 h before quenching with sat. $NH_4Cl_{(aq)}$ and extraction with DCM. The combined extracts were dried and the solvent evaporated to yield the crude ketone. Where a nitrile was used the imine was treated as described in i) to yield the crude ketone. The crude ketone was used as is or was purified by crystallisation or flash chromatography.

Method B 3-(Ethoxymethoxy)pyridine (1 eq) was dissolved in THF and cooled to −78° C. before n-BuLi in hexanes (1 eq) was added keeping the temperature at or below −78° C. The reaction was stirred for 0.5 h then the ester or amide (1 eq) dissolved in THF was added keeping temperature at or below −70° C. Whilst keeping cold, the reaction was stirred for 1.5 h after which time it was quenched with i-PrOH followed by sat. $NH_4Cl_{(aq)}$. The reaction was allowed to warm to RT before being extracted with EtOAc (3×), dried and the solvent evaporated to yield the crude ketone. The crude ketone was used as is or was purified by crystallisation or flash chromatography.

Method C

These methods are based on those described in the literature as represented by Deane K. J. et al., ACS Med. Chem. Lett., 2014, 5, pp 576-581 and Shi J. et al, ACS Omega, 2017, 2, pp 3406-3416.

i) n-BuLi in hexanes (1.17 eq) was added to a solution of 2-bromopyridine (1.0 eq) in THF and ether (1:1) at −110° C. The reaction was warmed to −10° C. over 0.5 h. The flask was again cooled to −110° C. and a solution/suspension of the ester (1.0 eq) in toluene (1.3 mL/mmol) was added. The reaction was stirred at RT for 17 h, after which time it was quenched with sat. $NH_4Cl_{(aq)}$, followed by water. The mixture was extracted with EtOAc (3×) and the combined layers were washed with water, brine and then dried ($Na_2SO_4$). After concentration under reduced pressure the crude product was adsorbed onto $SiO_2$ and purified by flash chromatography.

ii) 2-Bromopyridine (1.0 eq) in THF (5.5 mL/mmol) was added dropwise to a solution of n-BuLi in hexane (1.0 eq) over 1 h at −78° C. The reaction was stirred at −78° C. for a further 1 h before a concentrated solution of the ester (1.0 eq) in THF was added and the reaction slowly allowed to warm to −20° C. then being maintained at this temperature for 2 h or until MS showed no sign of starting material. When complete, the reaction was quenched with a 10%

$HCl_{(aq)}$ and the pH adjusted to pH6 using a 2M $HCl_{(aq)}$. The mixture was extracted with DCM (3×), dried and concentrated under reduced pressure to yield the crude ketone. The crude ketone was used as is or was purified by crystallisation or flash chromatography.

Method D

Standard techniques as described in Protective Groups in Organic Synthesis, Green, T. W. and Wuts P. G. M. John Wiley & Sons, New York, 1999 were employed to deprotect Intermediates I, III, IV, VI or Formula IA. In general, HBr or $BBr_3$ were employed to remove methyl and benzyl ether or hydrogenation where applicable. HCl, TFA or TMSOTf was used to remove acetals or Boc groups.

i) The ether was suspended in 48% $HBr_{(aq)}$ and heated at 60-130° C. for 0.5-5 d. The reaction was cooled then concentrated under reduced pressure to afford a solid. The solid was treated with sat. $NaHCO_{3(aq)}$ and extracted with EtOAc (3×). The combined organic extracts were washed with brine, dried and concentrated under reduced pressure to afford the crude product. Alternatively, the reaction can be diluted with water and neutralised with conc. $NH_{3(aq)}$ (re-buffering with AcOH if required) before being extracted with EtOAc. If required, samples were further purified by flash chromatography or crystallisation.

ii) The ether was dissolved in DCM and cooled to 0° C. before boron tribromide (6-12 eq) was added dropwise and the reaction warmed to RT. The mixture was stirred at for 17-48 h before MeOH was added and the solvent evaporated. MeOH was again added and the solvent evaporated (2×) before the residue was dissolved in EtOAc and washed with water (1×). The organic extract was dried and concentrated under reduced pressure to yield the crude product. Further purification may be achieved by trituration, crystallisation or chromatography.

Method E

Standard techniques as described in Comprehensive Organic Transformations: A Guide to Functional Group Preparations, Larock, R. C. John Wiley & Sons, New York, 2018 were employed to convert Intermediate III to IV or Intermediate VI to Intermediate VII. In general, mild oxidants such as $SeO_2$, pyridine.$SO_3$ or Dess-Martin periodinane were used.

Method F

This general methodology is widely described in the literature and is exemplified by that described by Wu, J. et al. Chem. Commun., 2010, 46, pp 3687-3689.

Intermediates I, II, V or VII (1.0 eq), aldehyde (1.5-3 eq, except for intermediate VII) and $NH_4OAC$ (5-10 eq) were suspended in AcOH in a sealed vial. The contents were heated at between 40-110° C. for 16-72 h then cooled. The reaction mixture was poured onto iced water and the product isolated either by filtration or extraction and the crude product further purified, if required, by trituration, crystallisation or flash chromatography.

Method G

Hydrogenations were carried out at RT under an atmosphere of $H_{2(g)}$ supplied by a balloon using 10% Pd/C (0.1-1 w/w equivalent). Starting materials were dissolved or suspended in low MW alcohols, THF, EtOAc or a combination of these solvents. Reaction times ranged from 1-48 h and upon completion, usually determined by MS, the reaction catalyst was filtered and the solvent evaporated to yield the crude product which was purified using normal techniques if required.

Method H

Boc-cyclic amines were metalated with sec-BuLi under the conditions described by either Beak P. et al. J. Org. Chem. 1993, 58, pp 1109-1117 or Barker G. et al. Org. Lett. 2010, 12, pp 4176-4179 using the appropriate electrophile.

Method I

CDI (1.1 eq) was added to a carboxylic acid (1.5 eq) in THF and the solution heated to 50° C. After stirring for 30 mins the reaction was cooled to RT before being added to a solution/suspension of the amine or ammonium salt. The resultant mixture was stirred for 15-72 h after which time the reaction was diluted with water and extracted with EtOAc (3×). The EtOAc was subsequently extracted with 10% $HCl_{(aq)}$ (2×) and the resultant aqueous extract neutralised with sat. $NaHCO_{3(aq)}$ before again being extracted with EtOAc (3×). The combined extracts were dried and the solvent evaporated to yield the crude product which was used directly or purified using standard techniques.

Method J

CDI (2 eq) was added to salicylic acid (2 eq) in 1,4-dioxane (1 mL) and the mixture heated to 50° C. After stirring for 30 min the reaction was cooled to yield the acylating solution. At the same time Boc-amine (1 eq) in 1,4-dioxane was treated with HCl in 1,4-dioxane and the solution stirred at RT. After ~30 min $Et_2O$, hexanes or a mixture was added to aid the precipitation of the HCl salt. The solvent was decanted and the hygroscopic solid either washed with $Et_2O$ (3×) or filtered and washed with $Et_2O$ before being dried briefly in vacuo and suspended again in 1,4-dioxane. In the case of the pyrrolidine salt, this suspension was added to the cooled acylating solution whereas the acylating solution was added to the cooled azepane salt solution. The reactions were stirred overnight after which time the samples were diluted with water and extracted with EtOAc (3×). The combined extracts were passed through a $SiO_2$ plug, eluting with EtOAc before the solution was evaporated to yield the crude acylated amine. After MS confirmation of the target, the material was used without further manipulation. The crude product was usually a mixture of the target along with diacylated target with acylation presumed to be on the phenol. This acyl group was removed under the conditions employed in the subsequent step.

Synthesis of Selected Starting Materials and Condensation Precursors

Synthesis of Substituted Benzaldehydes

2-Hydroxy-3-(morpholinomethyl)benzaldehyde

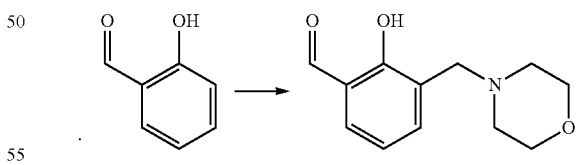

Morpholine (10.7 g, 12.2 mmol) was added to a solution of salicylaldehyde (10.0 g, 0.08 mol) and paraformaldehyde (3.7 g, 12.2 mmol) in EtOH (80 mL) and heated at reflux for 17 h. The reaction was cooled, concentrated under reduced pressure then the residue was redissolved in DCM and dried ($Na_2SO_4$). Concentration again gave an orange oil which was loaded onto silica (5 g). This product (in two batches) was purified by column chromatography (silica, 40 g) eluting with hexane (3CV) then 0-40% EtOAc in hexane gave 2-hydroxy-3-(morpholinomethyl)benzaldehyde (combined yield 1.00 g, 6%). MS: m/z ($MH^+$) 222.11. $^1H$ NMR ($CDCl_3$, 600MHZ) δ 10.22 (1H, s), 7.60 (1H, dd, J 1.8, 7.8 Hz), 7.37 (1H, d, J 7.2 Hz), 6.91 (1H, t, 7.2 Hz), 3.75 (4H, t, J 4.8 Hz), 3.68 (2H, s), 2.57 (4H, s).

Synthesis of
2-hydroxy-3-(2-morpholinoethyl)benzaldehyde

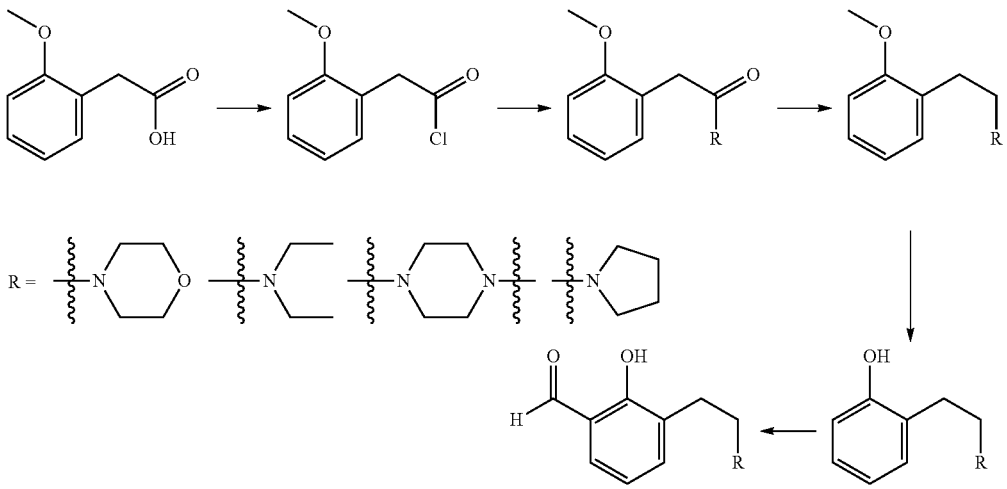

2-(2-Methoxyphenyl)-1-morpholinoethanone 2-(2-Methoxyphenyl)acetic acid (10.0 g, 0.06 mol) was dissolved in DCM (78 mL) to which was added thionyl chloride (10.7 g, 0.09 mol) and DMF (0.04 g, 0.6 mol). The reaction was stirred at RT under argon for 17 h, then concentrated under reduced pressure to give the 2-(2-methoxyphenyl)acetyl chloride as a yellow oil. The acid chloride (2.0 g, 11.0 mmol) was diluted in DCM (44 mL) and cooled to 0° C. Morpholine (2.8 g, 0.03 mol) was diluted in DCM (27 mL) and added dropwise to the cooled solution and left at 0° C. for 15 min. The reaction was then stirred at RT for 5.5 h, or until TLC showed one spot. A 10% aqueous solution of HCl (20 mL) was added to the reaction mixture and the DCM layer removed. The aqueous solution was extracted with DCM again (20 mL×2) and the combined organic layers were washed with brine (20 mL) and dried ($Na_2SO_4$). Concentration gave 2-(2-methoxyphenyl)-1-morpholinoethanone as a yellow oil (2.58 g, 100%). $^1$H NMR ($CDCl_3$, 600 MHz) δ 7-24-7.21 (2H, m), 6.90 (1H, td, 0.6, 7.2 Hz), 6.85 (1H, d, J 8.4 Hz), 3.81 (3H, s), 3.68 (2H, s), 3.63 (4H, bs), 3.51 (2H, bs), 3.45 (2H, bs).

4-(2-Methoxyphenethyl)morpholine 2-(2-Methoxyphenyl)-1-morpholinoethanone (2.87 g, 12.0 mmol) in THF (24 mL) was added dropwise to a suspension of $LiAlH_4$ (0.65 g, 17.0 mmol) in THF (18 mL) at RT. The reaction was stirred for 2 h then cooled to around 0° C. A 2M aqueous solution of NaOH was added cautiously to quench the reaction. The reaction was filtered through celite, washed with ether (×4) and the filtrate dried ($Na_2SO_4$). Concentration under reduced pressure gave 4-(2-methoxyphenethyl)morpholine as a yellow oil (2.15 g, 81%). $^1$H NMR ($CDCl_3$, 600 MHz) δ 7.16 (1H, td, J 1.8, 7.8 Hz), 7.13 (1H, d, 1.0, 7.8 Hz), 6.89 (1H, t, J 7.8 Hz), 6.83 (1H, d, J 7.8 Hz), 3.80 (3H, s), 3.75 (2H, s), 3.74 (2H, s), 2.81 (2H, m), 2.56-2.54 (6H, m).

2-(2-Morpholinoethyl)phenol 4-(2-Methoxyphenethyl)morpholine (2.15 g, 9.70 mmol) was heated in 48% aqueous HBr solution (1 mL) at 120° C. for 17 h. The reaction mixture was concentrated under reduced pressure and the residue was made basic by the additions of an aqueous solution of $NaHCO_3$. The aqueous mixture was extracted with DCM (50 mL×3). The extracts were combined and washed with brine (5 mL), dried ($Na_2SO_4$) and concentrated to give 2-(2-morpholinoethyl)phenol as a red solid/oil (1.90 g, 95%). $^1$H NMR ($CDCl_3$, 600 MHz) δ 7.12 (1H, td, J 1.8, 8.4 Hz), 6.98 (1H, dd, 1.2, 7.2 Hz), 6.87 (1H, dd, J 1.2, 8.4 Hz), 6.74 (1H, td, J 1.2, 7.2 Hz), 3.82 (4H, t, J 4.2 Hz), 2.84 (2H, t, J 4.8 Hz), 2.73 (6H, m).

2-Hydroxy-3-(2-morpholinoethyl)benzaldehyde 2-(2-Morpholinoethyl)phenol (1.90 g, 9.20 mmol) was dissolved in MeCN (6 mL) and triethylamine (4.8 mL, 0.25 mol) was added. Paraformaldehyde (1.86 g, 0.06 mol) and magnesium chloride (1.77 g, 18.0 mmol) were added and the reaction was heated at reflux under argon for 17 h. The reaction was cooled then diluted with an aqueous 0.1 M Na/K tartrate solution (100 mL). The mixture was extracted with DCM (20 mL×3), washed with brine (20 mL), dried ($Na_2SO_4$) and concentrated to give 2-hydroxy-3-(2-morpholinoethyl)benzaldehyde as a brown oil that was used in the next step without additional purification (1.01 g, 47%). $^1$HNMR ($CDCl_3$, 600 MHz) δ 11.95 (1H, bs), 10.05 (1H, s), 7.48 (1H, d, J 7.8 Hz), 7.36 (1H, d, 6.6 Hz), 6.90 (1H, t, J 7.2 Hz), 3.79 (4H, bs), 2.91 (2H, s), 2.45 (6H, m). MS: m/z ($MH^+$) 236.13.

Synthesis of
3-(2-(diethylamino)ethyl)-2-hydroxybenzaldehyde

The procedures for the synthesis of 2-hydroxy-3-(2-morpholinoethyl)benzaldehyde were used with diethylamine to give 3-(2-(diethylamino)ethyl)-2-hydroxybenzaldehyde as a yellow solid (2.92 g, 26%). $^1$HNMR ($CDCl_3$, 600 MHz) δ 10.31 (1H, bs), 7.55 (1H, dd, J 1.8, 7.8 Hz), 7.26 (1H, d, 6.6 Hz), 6.79 (1H, t, J 7.2 Hz), 2.89 (2H, bs), 2.81-2.77 (6H, m), 1.16 (6H, t, J 6.6 Hz). MS: m/z ($MH^+$) 222.15.

Synthesis of 2-hydroxy-3-(2-(4-methylpiperazin-1-yl)ethyl)benzaldehyde

The procedures for the synthesis of 2-hydroxy-3-(2-morpholinoethyl)benzaldehyde were used with 1-methylpiperazine to give 2-hydroxy-3-(2-(4-methylpiperazin-1-yl)ethyl)benzaldehyde as brown gummy solid (0.22 g, 14%). $^1$H NMR (CDCl$_3$, 600 MHz) δ 10.20 (1H, s), 7.51 (1H, dd, J 1.2, 7.2 Hz), 7.30 (1H, dd, J 1.2, 7.8 Hz), 6.84 (1H, t, 7.8 Hz), 2.86 (2H, t, 6.6 Hz), 2.69-2.40 (10H, m), 2.32 (3H, s). MS: m/z (MH$^+$) 249.16.

Synthesis of 2-hydroxy-3-(2-(pyrrolidin-1-yl)ethyl)benzaldehyde

The procedures for the synthesis of 2-hydroxy-3-(2-morpholinoethyl)benzaldehyde were used with pyrrolidine to give 2f-hydroxy-3-(2-(pyrrolidin-1-yl)ethyl)benzaldehyde (0.22 g, 7%). $^1$H NMR (CDCl$_3$, 600MHz) δ 11.50 (1H, bs), 10.30 (1H, s), 7.55 (1H, d, J 7.8 Hz), 7.24 (1H, d, J 7.2 Hz), 6.77 (1H, t, 7.2 Hz), 2.87 (2H, d, 5.4 Hz), 2.82 (2H, d, 5.4 Hz), 2.77 (4H, bs), 1.89 (4H, bs). MS: m/z (MH$^+$) 220.13.

Synthesis of 2-hydroxy-3-(3-morpholinopropyl)benzaldehyde

Based on the methodology of Fumitaka, I., Hiroki K., Asata M., WO03064425 (A1), 2003.

(E)-3-(2-Methoxyphenyl)acrylic acid

A well stirred solution of 2-methoxybenzaldehyde (10.9 g, 0.08 mol), malonic acid (19.7 g, 0.16 mol), piperidine (3.1 g, 0.04 mol) and pyridine (100 ml) were heated at 80-90° C. for 2.5 h, then stirred at RT overnight. The reaction was poured onto an aqueous 3M solution of HCl in iced water (700 mL) and stirred. The precipitate was filtered off then resuspended in cold water (500 mL) and stirred for 10 min. Filtration followed by washing the solid with water, hexane and ether gave a white solid that was dried under reduced pressure (11.6 g, 81%). $^1$H NMR (d$_6$-Acetone, 600 MHz) δ 7.98 (1H, d, J 16.2 Hz), 7.65 (1H, dd, 1.8, 7.8 Hz), 7.39 (1H, td, J 1.8, 7.8 Hz), 7.07 (1H, d, J 8.4 Hz), 6.98 (1H, t, J 7.8 Hz), 6.53 (1H, d, J 16.2 Hz), 3.92 (3H, s).

3-(2-Methoxyphenyl)propanoic acid (E)-3-(2-Methoxyphenyl)acrylic acid (11.6 g, 0.07 mol) was reduced in EtOH (500 mL) using 10% Pd—C (1.5 g) according the general Method G. A cream solid was isolated that did not require further purification (11.4 g, quantitative yield). $^1$H NMR (CDCl$_3$, 600 MHz) δ 7.19 (1H, td, J 1.2, 7.8 Hz), 7.15 (1H, dd, 1.2, 7.2 Hz), 6.87 (1H, dd, 1.2, 7.8 Hz), 6.84 (1H, d, 8.4 Hz), 3.01 (3H, s), 2.94 (2H, t, 7.8 Hz), 2.65 (2H, t, 7.8 Hz).

3-(2-Methoxyphenyl)propan-1-ol 3-(2-Methoxyphenyl)propanoic acid (11.4 g, 0.0 mol) dissolved in ether (126 mL) was added slowly to a suspension of LiAlH$_4$ (6.0 g, 0.16 mol) in ether (190 mL) at RT. The reaction was headed at reflux overnight, then cooled to RT before the reaction was quenched with water (100 mL). The reaction was filtered through a pad of celite washing with water (20 mL) and EtOAc (200 mL). The EtOAc layer was removed and the aqueous layer was extracted with more EtOAc (100 mL×2). The EtOAc layers were washed with brine (100 mL) and dried (Na$_2$SO$_4$). Concentration gave a yellow/brown oil (5.1 g). Rewashing the celite pad with water (100 mL) and DCM (200 mL), and extracting the aqueous layer with more DCM (20 mL×3) afforded more product (1.61 g). Total yield (6.71 g, 67%). $^1$H NMR (CDCl$_3$, 600 MHz) δ 7.18 (1H, t, J 7.8 Hz), 7.14 (1H, d, J 6.6 Hz), 6.89 (1H, t, J 7.2 Hz), 6.85 (1H, d, J 7.8 Hz), 3.82 (3H, s), 3.60 (2H, t, J 6.0 Hz), 2.71 (2H, t, J 7.2 Hz), 1.90 (1H, bs), 1.84 (2H, t, J 6.6 Hz).

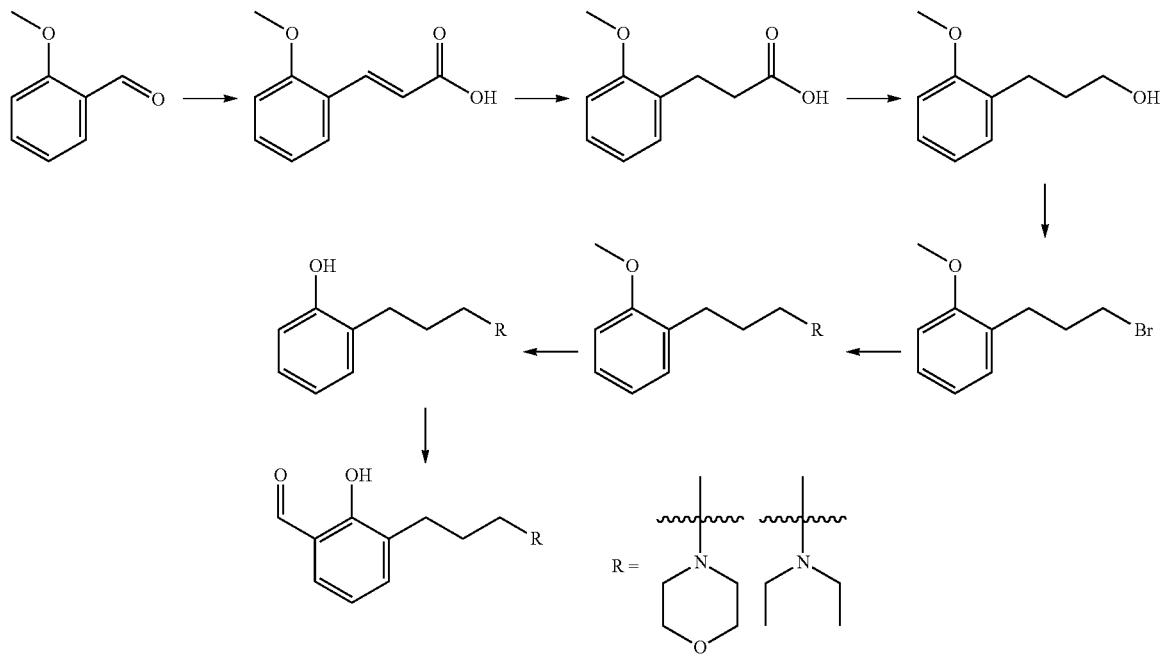

1-(3-Bromopropyl)-2-methoxybenzene 3-(2-Methoxyphenyl)propan-1-ol (1.6 g, 9.7 mmol) was dissolved in DCM (43 mL) to which was added triphenylphosphine (2.7 g, 0.01 mol). The solution was cooled in an ice bath and bromine (1.6 g, 0.01 mol) was added dropwise over 4 h whilst the reaction was maintained at 0-5° C. The reaction was quenched with a saturated aqueous solution of NaHCO$_3$ (15 mL), the DCM layer removed and the aqueous layer extracted with more DCM (50 mL×3). The combined organic layers were dried (Na$_2$SO$_4$) and concentrated to give a yellow solid. The solid was loaded onto silica (1 g) and purified by chromatography (silica, 24 g) eluting with hexane (3CV), 0-100% EtOAc in hexane (40CV) and EtOAc (CV). A clear oil was obtained (1.81 g, 81%). $^1$H NMR (CDCl$_3$, 600 MHz) δ 7.19 (1H, td, J 1.8, 7.8 Hz), 7.14 (1H, dd, J 1.2, 7.2 Hz), 6.87 (1H, td, J 0.6, 7.2 Hz), 6.84 (1H, d, J 8.4 Hz), 8.31 (3H, s), 3.39 (2H, t, J 6.6 Hz), 2.75 (2H, t, J 7.2 Hz), 2.13 (2H, t, J 7.2 Hz).

4-(3-(2-Methoxyphenyl)propyl)morpholine 1-(3-Bromopropyl)-2-methoxybenzene (1.8 g, 7.9 mmol), potassium carbonate (2.17 g, 16.0 mmol) and morpholine (1.1 g, 0.01 mol) were heated at reflux in ACN (4 mL) for 17 h. The reaction was concentrated then resuspended in EtOAc (50 mL), and washed with an aqueous 10% solution of HCl (50 mL). The aqueous layer was made basic with a 2M aqueous solution of NaOH and extracted with DCM (20 mL×3). The combined organic layers were dried (Na$_2$SO$_4$) and concentrated to give an oil which was loaded onto silica (2 g). Purification by chromatography (silica, 12 g) eluting with 0-100% EtOAc in hexane (30CV) gave a colourless oil (0.88 g, 48%). $^1$HNMR (CDCl$_3$, 500 MHz) δ7.18 (1H, td, J 1.5, 7.5 Hz), 7.13 (1H, d, J 7.5 Hz), 6.88 (1H, td, J 0.5, 7.0 Hz), 6.84 (1H, d, J 8.5 Hz), 3.82 (3H, s), 3.72 (4H, m), 2.64 (2H, t, J 8.0 Hz), 2.45 (4H, bs), 2.38 (2H, m), 1.78 (2H, m).

2-(3-Morpholinopropyl)phenol 4-(3-(2-Methoxyphenyl)propyl)morpholine (0.88 g, 3.73 mmol) was diluted with a 48% aqueous solution of HBr (7 mL) and heated at 120° C. for 17 h. The reaction was concentrated then a saturated aqueous solution of NaHCO$_3$ was added to the residue (pH 10-12). The solution was extracted with EtOAc (50 mL), then the pH of the aqueous solution was adjusted to pH9 and the solution extracted again with EtOAc (2 mL×2). The combined organic layers were washed with brine (15 mL), dried (Na$_2$SO$_4$) and concentrated to give reddish oil (0.73 g, 93%). $^1$H NMR (CDCl$_3$, 500MHZ) δ 7.12 (1H, td, J 2.0, 7.0 Hz), 7.07 (1H, dd, J 1.5, 7.5 Hz), 6.88 (1H, d, J 7.5 Hz), 6.84 (1H, td, J 1.5 Hz, 7.5 Hz), 3.84 (4H, bs), 2.69 (2H, t, J 6.0 Hz), 2.53 (4H, bs), 2.31 (2H, t, 4.5 Hz), 1.89 (2H, t, 6.0 Hz).

2-Hydroxy-3-(3-morpholinopropyl)benzaldehyde 2-(3-Morpholinopropyl)phenol (0.73 g, 3.3 mmol) was diluted in ACN (33 mL) to which was added triethylamine (1.0 g, 9.9 mmol), magnesium chloride (0.63 g, 6.6 mmol) and lastly paraformaldehyde (0.50 g, 16.0 mmol). The reaction was heated at reflux for 17 h, cooled then concentrated under reduced pressure. An 10% aqueous solution of HCl (50 mL) and DCM (50 mL) were added and the DCM layer removed. The aqueous layer was extracted exhaustively with DCM (30 mL×3) and EtOAc (30 mL×3). The combined organic layers were washed with a saturated aqueous solution of NaHCO$_3$ (20 mL), dried (Na$_2$SO$_4$) and concentrated to give yellow gum (0.68 g, 83%). $^1$H NMR (CDCl$_3$, 500 MHz) δ 9.98 (1H, s), 7.45 (1H, dd, J 1.5, 8.0 Hz), 7.39 (1H, dd, 1.0, 7.0 Hz), 6.95 (1H, t, J 8.0 Hz), 3.78-3.77 (4H, m), 2.73-2.68 (2H, m), 2.52 (4H, bs), 2.46-2.38 (2H, m), 1.91-1.85 (2H, m). MS: m/z (MH$^+$) 250.14.

Synthesis of 3-(3-(diethylamino)propyl)-2-hydroxybenzaldehyde

The procedures for the synthesis of 2-hydroxy-3-(3-morpholinopropyl)benzaldehyde were used with diethylamine to give 3-(3-(diethylamino)propyl)-2-hydroxybenzaldehyde as a gummy solid (1.17 g, 78%). MS: m/z (MH$^+$) 236.16.

Synthesis of 2-hydroxy-4-(morpholinomethyl)benzaldehyde 3-(Morpholinomethyl)phenol (1.60 g, 8.3 mmol) was diluted in ACN (42 mL) to which was added triethylamine (4.2 g, 0.04 mol), magnesium chloride (1.6 g, 16.5 mmol) and lastly paraformaldehyde (2.5 g, 0.08 mmol). The reaction was performed according to the method for 2-hydroxy-3-(3-morpholinopropyl)benzaldehyde, except that for the initial extraction, the pH of the aqueous solution was adjusted to pH 7 using a aqueous 2M solution of NaOH. A yellow oil was obtained (1.32 g, 72%). $^1$H NMR (CDCl$_3$, 500 MHz) δ 11.04 (1H, s), 9.87 (1H, s), 7.51 (1H, d, J 8.0 Hz), 7.02 (2H, m), 3.73 (4H, m), 3.51 (2H, s), 2.45 (4H, t, J 4.5 Hz).

Synthesis of Ketone Precursors

(2-Methoxypyridin-3-yl)(pyridin-2-yl)methanone

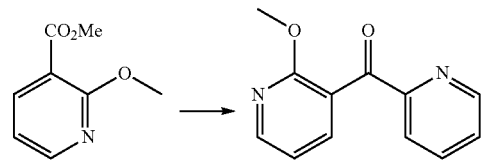 [SMILES: COC(=O)c1cccnc1OC ; COc1ncccc1C(=O)c1ccccn1]

The ketone was formed according to the general Method C(ii), using 2-bromopyridine (1.86 g, 11.7 mmol) in THF (50 mL) and a 2.37M w-BuLi in hexane (5.0 mL, 11.7 mmol) then methyl 2-methoxynicotinate (1.8 g, 11.7 mmol) in THF (3 mL). The green solid was used without any further purification (1.86 g, 74%). $^1$H NMR (CDCl$_3$, 600 MHz) δ 8.62 (1H, dq, J 1.2, 5.4 Hz), 8.31 (1H, dd, J 1.8, 4.8 Hz), 8.01 (1H, dd, J 1.2, 7.8 Hz), 7.86 (2H, dd, J 1.8, 7.2 Hz), 7.44 (1H, dddd, J 1.2, 4.2, 7.2, 12.0 Hz), 6.99 (1H, dd, J 5.4, 7.2 Hz), 3.81 (3H, s). MS: m/z (MH$^+$) 215.08.

(3-Hydroxypyridin-4-yl)(pyridin-2-yl)methanone

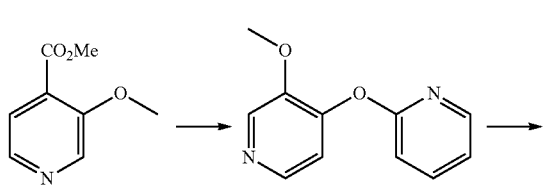

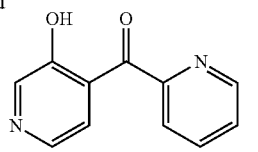

(3-Methoxypyridin-4-yl)(pyridin-2-yl)methanone

The ketone was formed according to the general Method C(i), using 2-bromopyridine (0.56 g, 3.5 mmol) in THF (4 mL) and ether (4 mL) followed by a 2.28M n-BuLi solution in hexane (1.8 mL, 4.1 mmol) then methyl 3-methoxyisonicotinate (0.59 g, 3.5 mmol). The brown gum was dry loaded onto silica then purified by chromatography (silica, 12 g) eluting with 0-100% EtOAc in hexane over 50CV. The desired product eluted from the column last to afford a pale-yellow solid (0.30 g, 42%). $^1$H NMR (CDCl$_3$, 600 MHz) δ 8.63 (1H, dd, J 0.6, 4.8 Hz), 8.43 (1H, s), 8.39 (1H, d, J 4.8 Hz), 8.09 (1H, d, J 7.8 Hz), 7.89 (1H, td, J 1.2, 7.8 Hz), 7.47 (1H, dd, J 4.8, 7.8 Hz), 7.31 (1H, d, J 4.8 Hz), 3.79 (3H, s).

(3-Hydroxypyridin-4-yl)(pyridin-2-yl)methanone (3-Methoxypyridin-4-yl)(pyridin-2-yl)methanone (0.30 g, 1.4 mmol) was reacted with a concentrated aqueous solution of HBr (4 mL) according to the general Method D(i), and heated for 48 h. A yellow solid was obtained (0.24 g, 86%). $^1$H NMR (d$_6$-DMSO, 600 MHz) δ 13.7 (1H, bs), 8.72 (1H, ddd, J 1.2, 1.8, 5.4 Hz), 8.57 (1H, d, J 1.8 Hz), 8.23 (1H, dt, J 0.6, 7.8 Hz), 8.21 (1H, dd, J1.8, 5.4 Hz), 8.06 (1H, td, J 1.8, 7.8 Hz), 7.96 (1H, dd, J 1.2, 5.4 Hz), 7.67 (1H, td, J 4.8, 7.2 Hz).

(4-Methoxypyridin-3-yl)(pyridine-2-yl)methanone

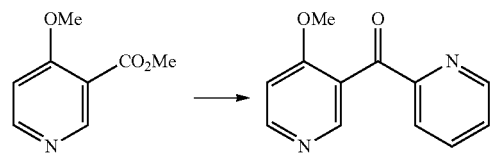 [SMILES: COC(=O)c1cnccc1OC ; COc1ccncc1C(=O)c1ccccn1]

2-Bromopyridine (0.87 g, 5.5 mmol), methyl 4-methoxynicotinate (0.92 g, 5.5 mmol) diluted in THF (2 mL) and a 2.37 M solution of n-butyl lithium in hexane (2.3 mL, 5.5 mmol) were reacted in THF (25 mL) according to the general Method C(ii). A light brown gummy solid resulted (0.78 g, 67%) that was used in the next step without additional purification. $^1$H NMR (CDCl$_3$, 600 MHz) δ8.62 (1H, dq, J 0.6, 4.8 Hz), 8.61 (1H, s), 8.60 (1H, d, J 6.0 Hz), 8.05 (1H, td, J 1.2, 7.8 Hz), 7.87 (1H, td, J 1.2, 7.8 Hz), 7.45 (1H, dddd, J 1.2, 4.8, 7.8, 12.0 Hz), 6.90 (1H, d, J 5.4 Hz), 3.75 (3H, s). MS: m/z (MH$^+$) 215.08.

(3-(Benzyloxy)-6-methylpyridin-2-yl)(pyridin-2-yl) methanone

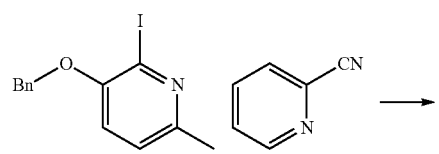

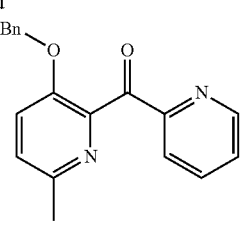

Prepared using 3-(benzyloxy)-2-iodo-6-methylpyridine (130 mg), picolinonitrile (390 mg) with THF as the solvent and 2.27M M-BuLi in hexanes (1.94 mL) using general Method A ii). The crude product was purified on 12 g SiO$_2$ using EtOAc/hexanes gradient 0-0% 3CV, 0-100% 30CV. The product fractions were combined and evaporated to yield the title compound as an oil which slowly solidified (456 mg) and was used without further manipulation. $^1$H NMR (CDCl$_3$, 600MHZ) δ 8.63 (1H, d, J 4.2 Hz), 8.12 (1H, d, J 7.8 Hz), 7.84 (1H, t, J 7.8 Hz), 7.42 (1H, dd, J 4.7, 7.4 Hz), 7.27-7.18 (5H, m), 7.07-7.03 (2H, m), 4.99 (2H, s), 2.55 (3H, s).

(2-Hydroxyphenyl)(pyridine-2-yl)methanone

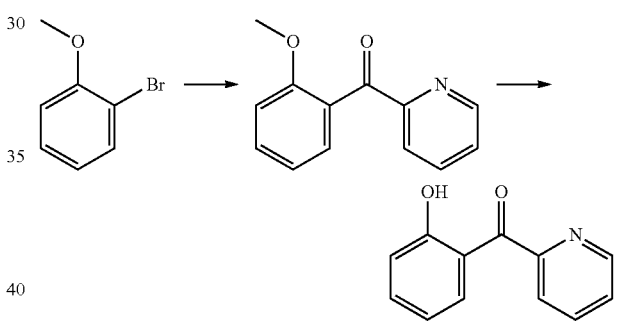

(2-Methoxyphenyl)(pyridine-2-yl)methanone

This compound was prepared from 2-bromoanisole (6.0 g, 32 mmol), 2-pyridylcarbonitrile (3.0 g, 29 mmol) and magnesium (0.86 g, 35 mmol) following the general Method A(i). The title compound was isolated as pale-yellow crystals (1.76 g, 26%). $^1$H NMR (d$_6$-DMSO, 600 MHz) δ 8.63 (1H, d, J 3.6 Hz), 7.97 (1H, d, J 7.8 Hz), 7.84 (1H, t, J 7.8 Hz), 7.52 (1H, d, J 7.2 Hz), 7.47 (1H, d, J 7.8 Hz), 7.41 (1H, t, J 4.8 Hz), 7.04 (1H, t, J 7.2 Hz), 7.96 (1H, d, J 8.4 Hz), 3.64 (3H, s).

(2-Hydroxyphenyl) (pyridine-2-ylmethanone (2-Methoxyphenyl)(pyridine-2-yl)methanone (0.15 g, 0.7 mmol) was reacted with HBr$_{(aq)}$ (12 mL) according to the general Method D(i), and heated for 17 h. The title compound was isolated as a brown oil (0.11 g, 78%). $^1$H NMR (d$_6$-DMSO, 600 MHz) δ 10.90 (1H, bs), 8.65 (1H, d, J 4.8 Hz), 8.02 (1H, t, J 7.8 Hz), 7.90 (1H, d, J 7.8 Hz), 7.61 (2H, d, J 7.8 Hz), 7.44 (1H, t, J 7.2 Hz), 6.88-6.93 (2H, m).

tert-Butyl 2-((3-(benzyloxy)-6-methylpyridin-2-yl)(hydroxy)methyl)pyrrolidine-1-carboxylate and tert-butyl 2-(3-(benzyloxy)-6-methylpicolinoyl)pyrrolidine-1-carboxylate

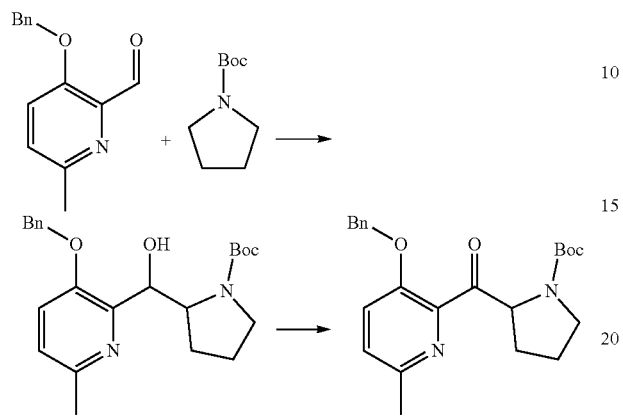

tert-Butyl 2-((3-(benzyloxy)-6-methylpyridin-2-yl)(hydroxy)methyl)pyrrolidine-1-carboxylate tert-Butyl pyrrolidine-1-carboxylate (4 g) was dissolved in $Et_2O$ (35 mL) and cooled to $-78°$ C. before treating with distilled TMEDA (3.3 mL). 1.28M s-BuLi (17.2 mL) was added, keeping the temperature $<-78°$ C. during the addition. Once complete, the reaction was stirred at this temperature for 30 min after which time 2-carboxy-3-benzyloxy-6-methylpyridine (4.0 g) in $Et_2O$ (100 mL) was added, again keeping the temperature $<-78°$ C. The reaction was continued for a further 1.5 h whilst the reaction was allowed to warm to $\sim-60°$ C. The reaction was quenched with sat. $NH_4Cl_{(aq)}$ and allowed to warm to RT before extracting with $Et_2O$ (3×). The combined extracts were dried and the solvent evaporated to yield the crude product (8.66 g). The sample was adsorbed onto $SiO_2$ before purifying on 40 g $SiO_2$ (254/280 nm) using EtOAc/hexanes gradient 0-0% 3CV, 0-25% 20CV, 25-50% 10CV to yield the title compound (3.41 g, m/z (MH$^+$) 399.23) as a mixture of diastereomers and rotamers which was used without further manipulation.

tert-Butyl 2-(3-(benzyloxy)-6-methylpicolinoyl)pyrrolidine-1-carboxylate tert-Butyl 2-((3-(benzyloxy)-6-methylpyridin-2-yl)(hydroxy)methyl)pyrrolidine-1-carboxylate (1.04 g) was dissolved in DCM (15 mL) and Dess-Martin periodinane (2.44 g) was slowly added. The reaction was stirred at RT for 22 h after which time the reaction was diluted with water (~10 mL) and stirred for 10 min. The resultant precipitate was filtered and the DCM layer separated. The DCM extract was further washed with 2M $NaOH_{(aq)}$ (2×) then sat. $NaHCO_3$ $_{(aq)}$. The combined extracts were dried and the solvent evaporated to yield the crude product. The crude product was adsorbed onto $SiO_2$ and purified on a 12 g $SiO_2$ column (254/280 nm) using EtOAc/hexanes gradient 0-0% 3CV, 0-50% 30CV. The fractions containing the product were combined and evaporated to yield the title compound as an oil which solidified to a waxy solid on extended standing (805 mg). NMR displayed the product as a mixture of rotamers in 3:2 ratio. Unless specified peaks refers to both rotamers $^1$H NMR (CDCl$_3$, 500 MHz) δ 7.49-7.44 (2H, m), 7.44-7.26 (3H, m), 7.23-7.14 (2H, m), 5.63 (1H minor rotamer, dd, J 8.9, 3.1 Hz), 5.41 (1H major, dd, J 8.9, 4.5 Hz), 5.17 (1H minor, d not resolved), 5.16 (2H major, s), 5.14 (1H minor, d, J 12.6 Hz), 3.67-3.59 (2H, m), 3.55-3.50 (2H, m), 2.50 (3H major, s), 2.48 (3H minor, s), 2.33-2.23 (2H major, m), 2.05-1.80 (2H major 4H minor, m), 1.45 (9H minor, s), 1.27 (9H major, s); m/z (MH$^+$) 397.21.

tert-Butyl 2-(2-methoxynicotinoyl)pyrrolidine-1-carboxylate

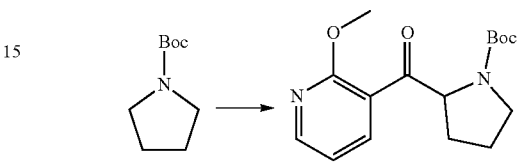

tert-Butyl pyrrolidine-1-carboxylate (1.5 mmol, 0.26 g) was diluted with THF (10 mL) and cooled to $-40°$ C. sec-BuLi was added dropwise to this solution and the reaction was maintained at $-40°$ C. for 5 min before methyl 2-methoxynicotinate (3.0 mmol, 0.50 g) in THF (2 mL) was added. The reaction was stirred at $-40°$ C. for 10 min then warmed to RT over 15 min. The reaction was quenched with a saturated aqueous solution of ammonium chloride then extracted with DCM (15 mL×3). The combined organic extracts were dried ($Na_2SO_4$), then concentrated under reduced pressure to give a clear oil. The oil was loaded onto silica and purified by chromatography (silica, 12 g) eluting with hexane (3CV) then 0-50% EtOAc in hexane (40CV) then 50-80% EtOAc in hexane (15CV). The product was the last off the column and was isolated as a clear gum (0.20 g, 43%). The title compound appeared as a 1.1 (major): 1 (minor) mixture of rotamers. Unless specified, peaks refer to both rotamers. $^1$H NMR (CDCl$_3$, 500 MHz) δ8.29 (1H major, dd, J 1.5, 5.9 Hz), 8.28 (1H minor, dd, J 2.0, 4.5 Hz), 8.19 (1H minor, dd J 2.0, 4.5 Hz), 8.11 (1H major, dd J 2.0, 7.5 Hz), 7.01-6.95 (1H major, 1H minor, m), 5.29 (1H minor, dd, J 3.0, 9.0 Hz), 5.21 (1H major, dd, J 3.5, 9.0 Hz), 4.04 (3H major, s), 4.02 (3H minor, s), 3.66-3.56 (2H minor, m), 3.48-3.41 (2H major, m), 2.30-2.24 (2H minor, m), 1.95-1.92 (2H major, m), 1.91-1.86 (2H, m), 1.45 (9H major, s), 1.26 (9H minor, s). MS: m/z (MH$^+$) 307.16.

tert-Butyl 2-(3-(benzyloxy)-6-methylpicolinoyl)azepane-1-carboxylate

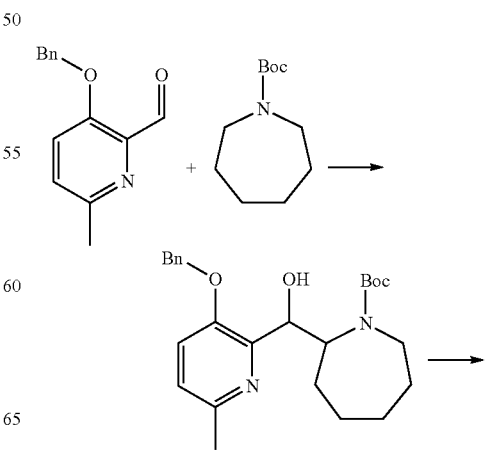

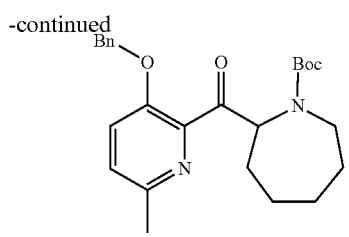

tert-Butyl 2-((3-(benzyloxy)-6-methylpyridin-2-yl)(hydroxy)methyl)azepane-1-carboxylate General Method H was used following the procedure of Beak, P. et al. where tert-butyl azepane-1-carboxylate (2.6 g) was dissolved in Et$_2$O (20 mL), was cooled to −78° C. then treating with distilled TMEDA (1.9 mL) before 1.28M sec-BuLi (10.2 mL) was added whilst keeping the temperature <−78° C. during the addition. Once complete, the reaction was stirred and allowed to warm to −40° C. during 1.5 h. The reaction was cooled and 2-carboxy-3-benzyloxy-6-methylpyridine (2.3 g) in Et$_2$O (50 mL, gently heated to dissolve in dropping funnel) was prepared and added to the reaction whilst keeping the temperature <−78° C. The reaction was continued for a further 1 h, allowing the temperature to increase to −60° C. The reaction was quenched with sat. NH$_4$Cl$_{(aq)}$ and allowed to warm to RT before being extracted with Et$_2$O (3×). The combined extracts were dried and the solvent evaporated to yield the crude alcohol. The sample was adsorbed onto SiO$_2$ before being purified on 40 g SiO$_2$ (254/280 nm) using EtOAc/hexanes gradient 0-0% 2CV, 0-25% 30CV. Fractions containing the target mass were identified by MS and combined to yield the title compound as a mixture of diastereomers and rotamers (898 mg, m/z (MH$^+$) 427.26) which was used without further manipulation.

tert-Butyl 2-(3-(benzyloxy)-6-methylpicolinoyl)azepane-1-carboxylate tert-Butyl 2-((3-(benzyloxy)-6-methylpyridin-2-yl)(hydroxy)methyl)azepane-1-carboxylate (1.04 g) was dissolved in DCM (15 mL) and DMP (2.44 g) was slowly added. The reaction was stirred at RT for 18 h after which time the reaction was diluted with water (10 mL) and stirred for 10 min. The resultant precipitate was filtered and the DCM separated. The DCM extract was washed with 2M NaOH$_{(aq)}$ then sat. NaHCO$_{3(aq)}$. The combined extracts were dried and the solvent evaporated to yield the crude ketone. The crude product was adsorbed onto SiO$_2$ and purified on a 12 g SiO$_2$ column (254/280 nm) using EtOAc/hexanes gradient 0-0% 3CV, 0-50% 30CV. The fractions containing the product were combined and evaporated to yield the title compound as an oil which solidified to a waxy solid on extended standing (676 mg) as a 1.4:1 mixture of rotamers. Unless specified peaks refers to both rotamers $^1$H NMR (CDCl$_3$, 500 MHz) δ 7.45-7.41 (2H, m), 7.40-7.26 (3H, m), 7.22 (1H major, d, J 8.5 Hz), 7.18 (1H minor, d, J 8.5 Hz), 7.15 (1H major, d, J 8.6 Hz), 7.12 (1H minor, d, J 8.5 Hz), 5.78 (1H minor, dd, J 6.4, 12.1 Hz), 5.39 (1H major, dd, J5.1, 11.8 Hz), 5.17 (1H minor, d, J 12.7 Hz), 5.15 (1H minor, d not resolved), 5.15 (1H major, d not resolved), 5.13 (1H major, d, J 13.0 Hz), 3.94-3.85 (1H minor, m), 3.22 (1H major, dd, J 10.4, 14.0 Hz), 3.07 (1H minor, ddd, J 1.6, 11.6, 14.8 Hz), 2.49 (3H major, s), 2.48 (3H minor, s), 2.44 (1H minor, m), 2.23-2.16 (1H major, m), 1.86-. 1.67 (4H, m), 1.59-1.42 (3H, m), 1.43 (9H minor, s), 1.27 (9H major, s).

Synthesis of compounds of Formula I

2-(3-(2-Hydroxyphenyl)-5,6,7,8-tetrahydroimidazo[1,5-a]pyridin-1-yl)-6-methylpyridin-3-ol (1)

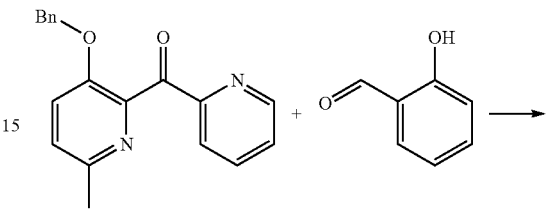

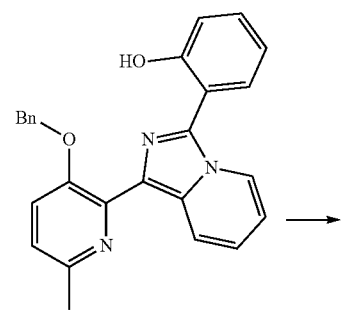

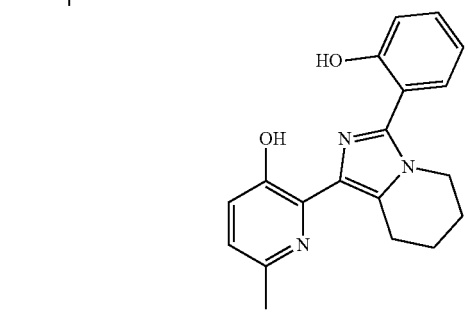

2-(1-(3-(Benzyloxy)-6-methylpyridin-2-yl) imidazo[1,5-a]pyridin-3-yl)phenol

The title compound was prepared employing the general Method F using 2-hydroxybenazaldehyde (39 μL), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 40 h. The extracted crude product was adsorbed onto SiO$_2$ and purified by flash chromatography using an EtOAc/hexanes gradient 0-75% 30CV. The desired fractions were combined and evaporated to yield the title compound (50 mg); $^1$H NMR (CDCl$_3$, 600 MHz) δ 12.5 (1H, bs), 8.56 (1H, d, J 7.2 Hz), 8.43 (1H, d, J 9.2 Hz), 7.80 (1H, dd, J 1.0, 7.7 Hz), 7.44 (2H, bd, J 7.3 Hz), 7.33-7.28 (3H, m), 7.28-7.23 (1H, m), 7.20 (1H, d, J 8.4 Hz), 7.16 (1H, d, J 8.1 Hz), 7.00 (1H, t, J 7.5 Hz), 6.95 (1H, d, J 8.4 Hz), 6.91 (1H, dd, J 6.6, 8.9 Hz), 6.74 (1H, t, J 6.9 Hz), 5.27 (2H, s), 2.56 (3H, s).

2-(3-(2-Hydroxyphenyl)-5,6,7,8-tetrahydroimidazo[1,5-a]pyridin-1-yl)-6-methylpyridin-3-ol (1)

The title compound was prepared employing the general Method G using 2-(1-(3-(benzyloxy)-6-methylpyridin-2-yl)

imidazo[1,5-a]pyridin-3-yl)phenol (48 mg), 10% Pd/C (25 mg) in a 1:1 mixture of EtOAc:EtOH (4 mL). The reaction was stirred at RT for 3 h, filtered and the solvent evaporated to yield the title compound as a tan solid (26 mg); $t_R$ 4.64 min (HPLC1); $^1$H NMR (d$_6$-Acetone, 600 MHz) δ 7.44 (1H, dd, J 1.5, 7.4 Hz), 7.39-7.31 (1H, m), 7.10-7.04 (1H, bs), 7.05 (1H, d, 8.2 Hz), 6.99 (1H, t, 7.4 Hz), 6.89 (1H, d, 8.2 Hz), 4.06 (2H, bt, 5.7 Hz), 3.35 (2H, t, 6.5 Hz), 2.42 (3H, s), 2.00-1.95 (2H, m), 1.94-1.89 (2H, m); m/z (MH$^+$) 322.16, (MH$_2^{2+}$) 161.58.

2-(3-(3-Fluoro-2-hydroxyphenyl)-5,6,7,8-tetrahydro-imidazo[1,5-a]pyridin-1-yl)-6-methylpyridin-3-ol
(2)

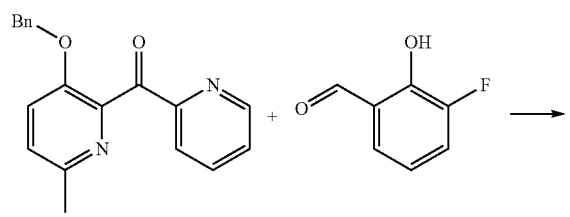

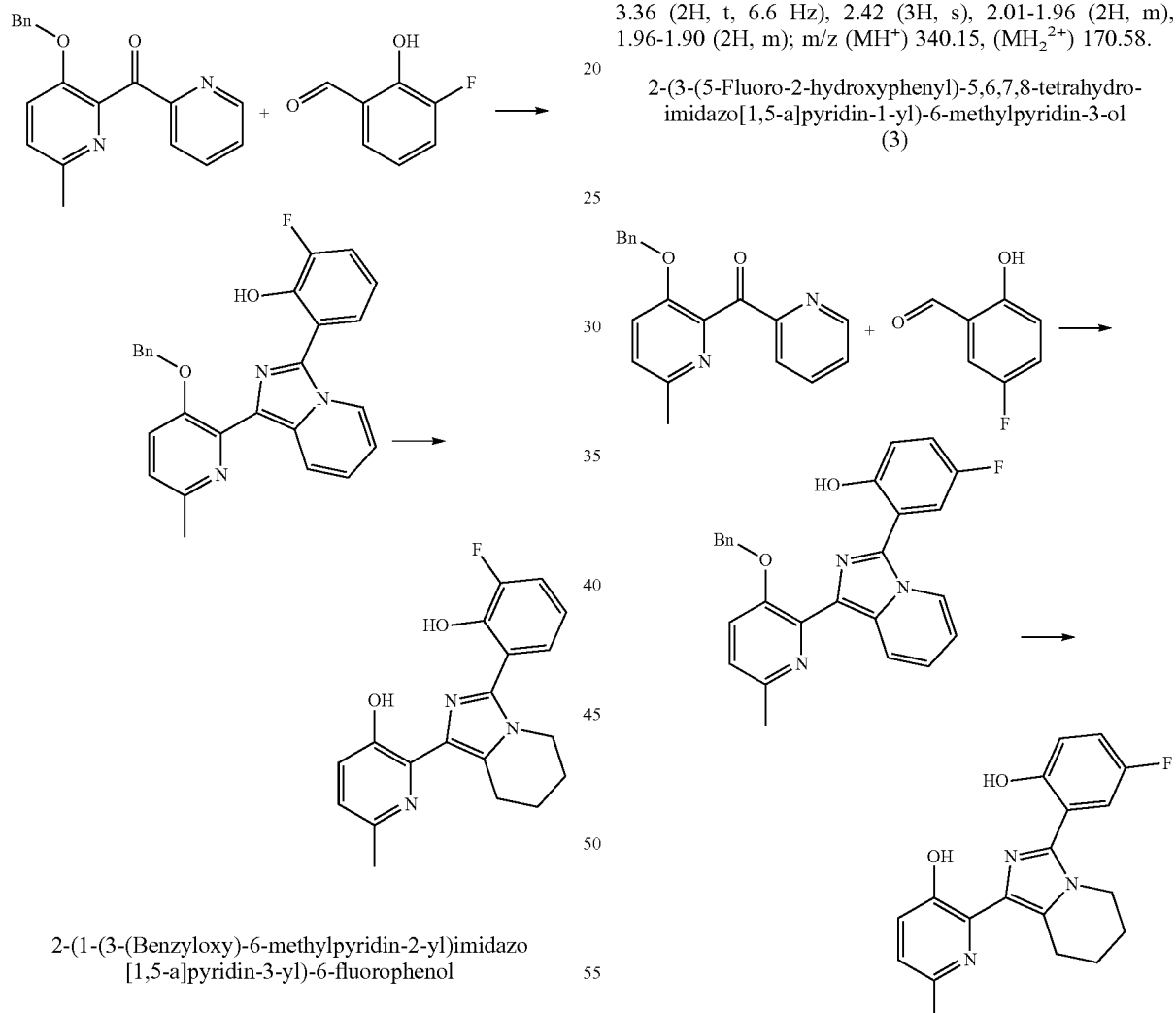

2-(1-(3-(Benzyloxy)-6-methylpyridin-2-yl)imidazo
[1,5-a]pyridin-3-yl)-6-fluorophenol The title compound was prepared employing the general Method F using 3-fluoro-2-hydroxybenzaldehyde (68 mg), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 40 h. The extracted crude product was adsorbed onto SiO$_2$ and purified by flash chromatography using an EtOAc/hexanes gradient 0-75% 30CV. The desired fractions were combined and evaporated to yield the title compound (40 mg); $^1$H NMR (CDCl$_3$, 600 MHz) δ 13.0 (1H, vbs), 8.57 (1H, d, J 7.2 Hz), 8.50 (1H, d, J 9.2 Hz), 7.60 (1H, d, J 7.9 Hz), 7.43 (2H, d, J 7.3 Hz), 7.34-7.29 (2H, m), 7.28-7.24 (1H, m), 7.21 (1H, d, J 8.4 Hz), 7.13 (1H, t, 9.4 Hz), 6.99-6.89 (3H, m), 6.80 (1H, t, J 6.7 Hz), 5.30 (2H, s), 2.57 (3H, s).

2-(3-(3-Fluoro-2-hydroxyphenyl)-5,6,7,8-tetrahydro-imidazo[1,5-a]pyridin-1-yl)-6-methylpyridin-3-ol
(2)

The title compound was prepared employing the general Method F using 2-(1-(3-(benzyloxy)-6-methylpyridin-2-yl) imidazo[1,5-a]pyridin-3-yl)-6-fluorophenol (41 mg), 10% Pd/C (25 mg) in a 1:1 mixture of EtOAc:EtOH (4 mL). The reaction was stirred at RT for 3 h, filtered and the solvent evaporated to yield the title compound as a beige solid (24 mg); $t_R$ 4.74 min (HPLC1); $^1$H NMR (d$_6$-Acetone, 600 MHz) δ 7.29-7.25 (2H, m), 7.05 (1H, d, 8.2 Hz), 6.98 (1H, dt 4.9, 8.0 Hz), 6.90 (1H, d, 8.2 Hz), 4.07 (2H, t, 5.9 Hz), 3.36 (2H, t, 6.6 Hz), 2.42 (3H, s), 2.01-1.96 (2H, m), 1.96-1.90 (2H, m); m/z (MH$^+$) 340.15, (MH$_2^{2+}$) 170.58.

2-(3-(5-Fluoro-2-hydroxyphenyl)-5,6,7,8-tetrahydro-imidazo[1,5-a]pyridin-1-yl)-6-methylpyridin-3-ol
(3)

2-(1-(3-(Benzyloxy)-6-methylpyridin-2-yl)imidazo
[1,5-a]pyridin-3-yl)-4-fluorophenol The title compound was prepared employing the general Method H using 5-fluoro-2-hydroxybenzaldehyde (54 mg), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 40 h.

The extracted crude product was adsorbed onto SiO$_2$ and purified by flash chromatography using an EtOAc/hexanes gradient 0-75% 30CV. The desired fractions were combined and evaporated to yield the title compound (48 mg); $^1$H NMR (CDCl$_3$, 600 MHz) δ 12.4 (1H, vbs), 8.53 (1H, d, J 7.2 Hz), 8.46 (1H, d, J 9.2 Hz), 7.50 (1H, dd, J 2.9, 9.5 Hz), 7.43 (2H, d, J 7.3 Hz), 7.33-7.28 (2H, m), 7.28-7.24 (1H, m), 7.22 (1H, d, J 8.4 Hz), 7.08 (1H, dd, J 5.0, 8.9 Hz), 7.01 (1H, dt, J 3.0, 9.0 Hz), 6.99-6.40 (2H, m), 6.82 (1H, dt, 1.2, 6.7 Hz), 5.27 (2H, s), 2.57 (3H, s).

2-(3-(5-Fluoro-2-hydroxyphenyl)-5,6,7,8-tetrahydroimidazo[1,5-a]pyridin-1-yl)-6-methylpyridin-3-ol (3)

The title compound was prepared employing the general Method G using 2-(1-(3-(benzyloxy)-6-methylpyridin-2-yl)imidazo[1,5-a]pyridin-3-yl)-4-fluorophenol (50 mg), 10% Pd/C (25 mg) in a 1:1 mixture of EtOAc:EtOH (4 mL). The reaction was stirred at RT for 3 h, filtered and the solvent evaporated to yield the title compound as a light brown solid (32 mg); t$_R$ 4.84 min (HPLC1); $^1$H NMR (d$_6$-Acetone, 600 MHz) δ 7.21 (1H, dd, J 2.9, 9.0 Hz), 7.16-7.10 (1H, m), 7.08-7.02 (1H, bm), 7.05 (1H, d, J 8.2 Hz), 6.89 (1H, d, J 8.2 Hz), 4.09 (2H, bt, J 5.6 Hz), 3.35 (2H, t, J 6.6 Hz), 2.42 (3H, s), 2.01-1.95 (2H, m), 1.95-1.89 (2H, m); m/z (MH$^+$) 340.15, (MH$_2^{2+}$) 170.58.

2-(3-(2-Fluoro-6-hydroxyphenyl)-5,6,7,8-tetrahydroimidazo[1,5-a]pyridin-1-yl)-6-methylpyridin-3-ol (4)

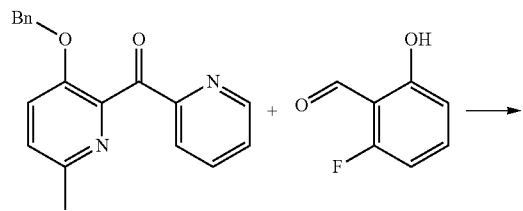

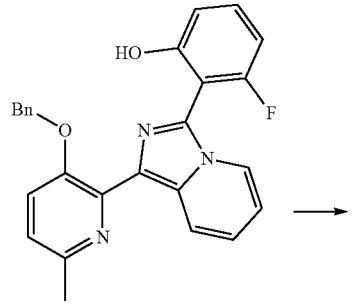

2-(1-(3-(Benzyloxy)-6-methylpyridin-2-yl)imidazo[1,5-a]pyridin-3-yl)-3-fluorophenol The title compound was prepared employing the general Method F using 2-fluoro-6-hydroxybenzaldehyde (68 mg), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 20 h then 60° C. for further 20 h. The extracted crude product was adsorbed onto SiO$_2$ and purified by flash chromatography using an EtOAc/hexanes gradient 0-75% 30CV. The desired fractions were combined and evaporated to yield the title compound (43 mg); $^1$H NMR (CDCl$_3$, 600MHZ) δ 11.4 (1H, vbs), 8.38 (1H, d, J 9.1 Hz), 8.00 (1H, dd, J 4.9, 6.0 Hz), 7.44 (2H, d, J 7.1 Hz), 7.33-7.25 (4H, m), 7.23 (1H, d, J 8.3 Hz), 7.00-6.95 (2H, m), 6.93 (1H, d, J 8.1 Hz), 6.80-6.75 (2H, m), 5.26 (2H, s), 2.58 (3H, s).

2-(3-(2-Fluoro-6-hydroxyphenyl)-5,6,7,8-tetrahydroimidazo[1,5-a]pyridin-1-yl)-6-methylpyridin-3-ol (4)

The title compound was prepared employing the general Method G using 2-(1-(3-(benzyloxy)-6-methylpyridin-2-yl)imidazo[1,5-a]pyridin-3-yl)-3-fluorophenol (45 mg), 10% Pd/C (25 mg) in a 1:1 mixture of EtOAc:EtOH (4 mL). The reaction was stirred at RT for 3 h, filtered and the solvent evaporated to yield the title compound as a beige solid (28 mg); t$_R$ 4.87 min (HPLC1); $^1$H NMR (d$_6$-Acetone, 600 MHz) δ 7.38 (1H, m), 7.04 (1H, d, J 8.2 Hz), 6.92-6.87 (1H, bm), 6.88 (1H, d, J 8.2 Hz), 6.76 (1H, t, J 8.8 Hz), 3.92 (2H, t, J 5.9 Hz), 3.35 (2H, t, J 6.5 Hz), 2.42 (3H, s), 2.00-1.95 (2H, m), 1.94-1.89 (2H, m); m/z (MIT) 340.15, (MH$_2^{2+}$) 170.58.

2-(3-(2-Hydroxy-5-methylphenyl)-5,6,7,8-tetrahydroimidazo[1,5-a]pyridin-1-yl)-6-methylpyridin-3-ol (5)

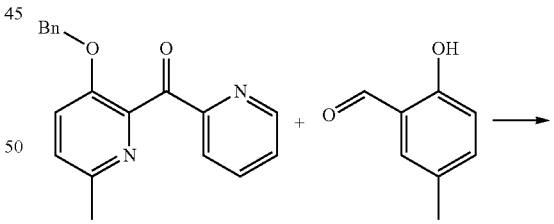

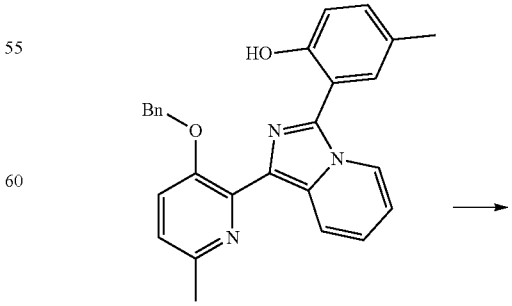

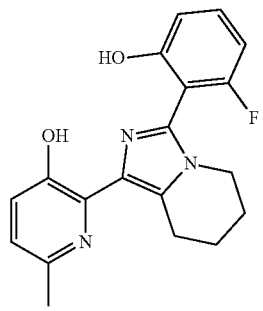

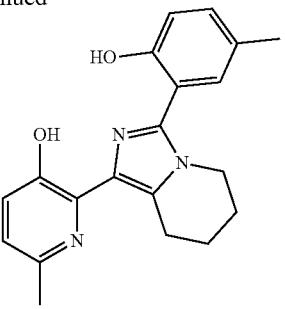

2-(1-(3-(Benzyloxy)-6-methylpyridin-2-yl)imidazo[1,5-a]pyridin-3-yl)-4-methylphenol The title compound was prepared employing the general Method F using 2-hydroxy-5-methylbenzaldehyde (54 mg), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 40 h. The extracted crude product was adsorbed onto SiO$_2$ and purified by flash chromatography using an EtOAc/hexanes gradient 0-75% 30CV. The desired fractions were combined and evaporated to yield the title compound (46 mg); $^1$H NMR (CDCl$_3$, 600 MHz) δ 12.2 (1H, vbs), 8.59 (1H, d, J 7.3 Hz), 8.42 (1H, d, J 9.2 Hz), 7.60 (1H, bs), 7.43 (2H, d, J 7.3 Hz), 7.33-7.28 (2H, m), 7.28-7.23 (1H, m), 7.20 (1H, d, J 8.4 Hz), 7.12 (1H, d, J 8.4 Hz), 7.06 (1H, d, J 8.3 Hz), 6.95 (1H, d, J 8.4 Hz), 6.92 (1H, dd, J 6.4, 9.2 Hz), 6.77 (1H, t, J 6.8 Hz), 5.27 (2H, s), 2.57 (3H, s), 2.40 (3H, s).

2-(3-(2-Hydroxy-5-methylphenyl)-5,6,7,8-tetrahydroimidazo[1,5-a]pyridin-1-yl)-6-methylpyridin-3-ol (5)

The title compound was prepared employing the general Method G using 2-(1-(3-(benzyloxy)-6-methylpyridin-2-yl)imidazo[1,5-a]pyridin-3-yl)-4-methylphenol (46 mg), 10% Pd/C (25 mg) in a 1:1 mixture of EtOAc:EtOH (4 mL). The reaction was stirred at RT for 3 h, filtered and the solvent evaporated to yield the title compound as a dark mustard solid (25 mg); t$_R$ 4.94 min (HPLC1); $^1$H NMR (d$_6$-Acetone, 600 MHz) δ 7.25-7.23 (1H, m), 7.17-7.14 (1H, m), 7.04 (1H, d, J 8.2 Hz), 6.98-6.92 (1H, bm), 6.88 (1H, d, J 8.2 Hz), 4.06-4.04 (2H, m), 3.35 (2H, t, J 6.5 Hz), 2.42 (3H, s), 2.30 (3H, s), 1.99-1.94 (2H, m), 1.94-1.89 (2H, m); m/z (MH$^+$) 336.17, (MH$_2$$^{2+}$) 168.59.

2-(3-(2-Hydroxy-3-methylphenyl)-5,6,7,8-tetrahydroimidazo[1,5-a]pyridin-1-yl)-6-methylpyridin-3-ol (6)

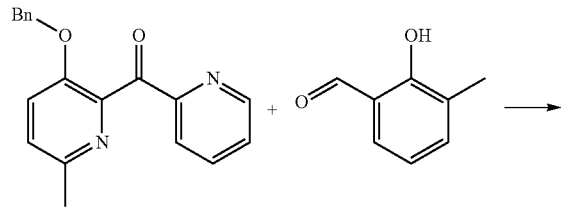

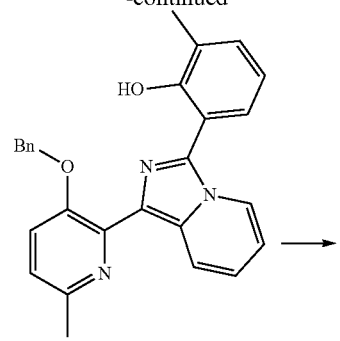

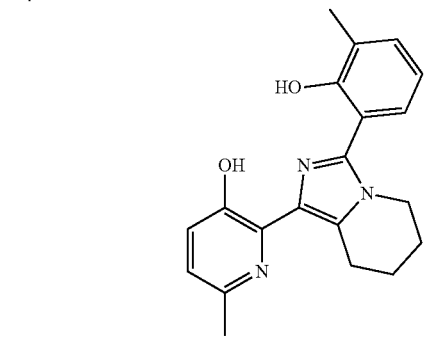

2-(1-(3-(Benzyloxy)-6-methylpyridin-2-yl)imidazo[1,5-a]pyridin-3-yl)-6-methylphenol The title compound was prepared employing the general Method F using 2-hydroxy-3-methylbenzaldehyde (60 μL), (3-(benzyloxy)-6-methylpyridin-2-yl)(pyridin-2-yl)methanone (50 mg) and NH$_4$OAc (126 mg) suspended in AcOH (0.5 mL) with the reaction being heated at 40° C. for 40 h then at 60° C. for further 28 h. The extracted crude product was adsorbed onto SiO$_2$ and purified by flash chromatography using an EtOAc/hexanes gradient 0-75% 30CV. The desired fractions were combined and evaporated to yield the title compound (47 mg); $^1$H NMR (CDCl$_3$, 600MHZ) δ 12.4 (1H, bs), 8.57 (1H, d, J 7.2 Hz), 8.43 (1H, d, J 9.1 Hz), 7.64 (1H, d, J 7.5 Hz), 7.47 (2H, d, J 7.1 Hz), 7.35-7.29 (2H, m), 7.29-7.22 (2H, m), 7.17 (1H, d, J 7.0 Hz), 6.98 (1H, d, J 8.4 Hz), 7.93-6.88 (2H, m), 6.73 (1H, t, J 6.7 Hz), 5.27 (2H, s), 2.58 (3H, s), 2.38 (3H, s).

2-(3-(2-Hydroxy-3-methylphenyl)-5,6,7,8-tetrahydroimidazo[1,5-a]pyridin-1-yl)-6-methylpyridin-3-ol (6)

The title compound was prepared employing the general Method G using 2-(1-(3-(benzyloxy)-6-methylpyridin-2-yl)imidazo[1,5-a]pyridin-3-yl)-6-methylphenol (48 mg), 10% Pd/C (25 mg) in a 1:1 mixture of EtOAc:EtOH (4 mL). The reaction was stirred at RT for 3 h, filtered and the solvent evaporated to yield the title compound as a tan solid (28 mg); t$_R$ 4.91 min (HPLC1); $^1$H NMR (d$_6$-Acetone, 600 MHz) δ 7.33 (1H, dd, J 1.5, 7.6 Hz), 7.24 (1H, dd, J 1.2, 7.4 Hz), 7.08 (1H, d, J 8.2 Hz), 6.92 (1H, d, J 8.2 Hz), 6.91 (1H, t, J 11.1 Hz), 4.12-4.10 (2H, m), 3.34 (2H, t, J 6.5 Hz), 2.43 (3H, s), 2.29 (3H, s), 2.02-1.96 (2H, m), 1.96-1.90 (2H, m); m/z (MH$^+$) 336.17, (MH$_2$$^{2+}$) 168.59.

63

2,2'-(5,6,7,8-tetraHydroimidazo[1,5-a]pyridine-1,3-diyl)diphenol (7)

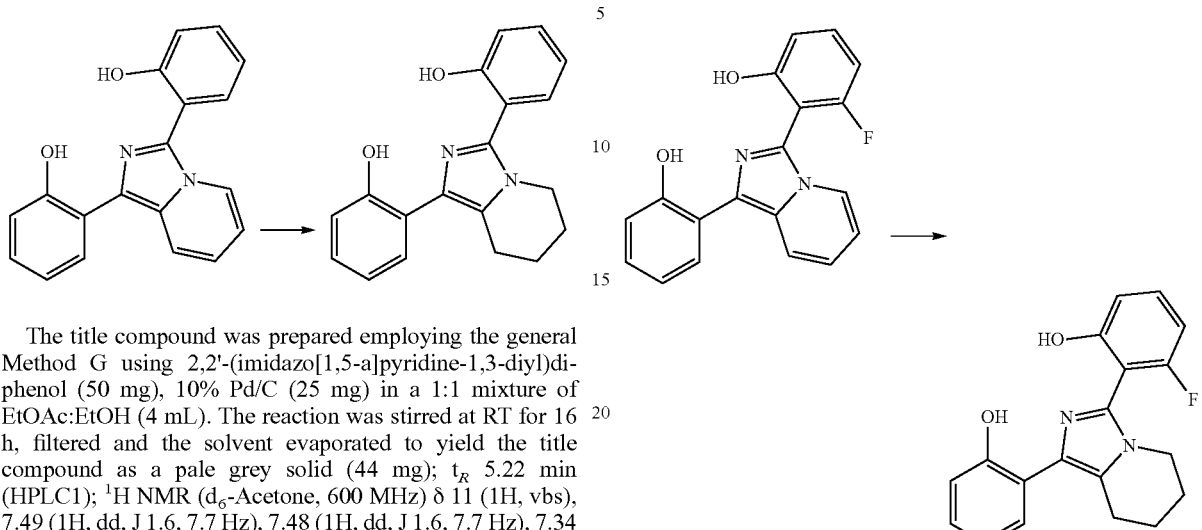

The title compound was prepared employing the general Method G using 2,2'-(imidazo[1,5-a]pyridine-1,3-diyl)diphenol (50 mg), 10% Pd/C (25 mg) in a 1:1 mixture of EtOAc:EtOH (4 mL). The reaction was stirred at RT for 16 h, filtered and the solvent evaporated to yield the title compound as a pale grey solid (44 mg); $t_R$ 5.22 min (HPLC1); $^1$H NMR ($d_6$-Acetone, 600 MHz) δ 11 (1H, vbs), 7.49 (1H, dd, J 1.6, 7.7 Hz), 7.48 (1H, dd, J 1.6, 7.7 Hz), 7.34 (1H, t, J 7.6 Hz), 7.10 (1H, dt, J 1.6, 8.9 Hz), 7.04 (1H, bd, J 8.1 Hz), 6.98 (1H, t, J 7.5 Hz), 6.88-6.83 (2H, m), 4.17 (2H, t, J 6.0 Hz), 3.09 (2H, t, J 6.2 Hz), 2.02-1.93 (4H, m); m/z (MH$^+$) 307.14.

2-(1-(2-Hydroxyphenyl)-5,6,7,8-tetrahydroimidazo[1,5-a]pyridin-3-yl)-4-methylphenol (8)

The title compound was prepared employing the general Method G using 2-(1-(2-hydroxyphenyl)imidazo[1,5-a]pyridin-3-yl)-4-methylphenol (20 mg), 10% Pd/C (25 mg) in a 1:1 mixture of EtOAc:EtOH (1 mL). The reaction was stirred at RT for 6 h, filtered and the solvent evaporated to yield the title compound as a white lyopholised solid (17 mg); $t_R$ 5.42 min (HPLC1); $^1$H NMR ($d_6$-Acetone, 600 MHz) δ 11.8 (1H, vbs), 9.6 (1H, vbs), 7.48 (1H, d, J 7.8 Hz), 7.29 (1H, bs), 7.15 (1H, bd, J 6.9 Hz), 7.09 (1H, ddd, J 1.5, 7.1, 8.2 Hz), 6.93 (1H, bd, J 7.9 Hz), 6.87-6.83 (2H, m), 4.11 (2H, bt, J 5.5 Hz), 3.09 (2H, bt, J 6.1 Hz), 2.30 (3H, s), 2.02-1.93 (4H, m); m/z (MH$^+$) 321.16.

64

3-Fluoro-2-(1-(2-hydroxyphenyl)-5,6,7,8-tetrahydroimidazo[1,5-a]pyridin-3-yl)phenol (9)

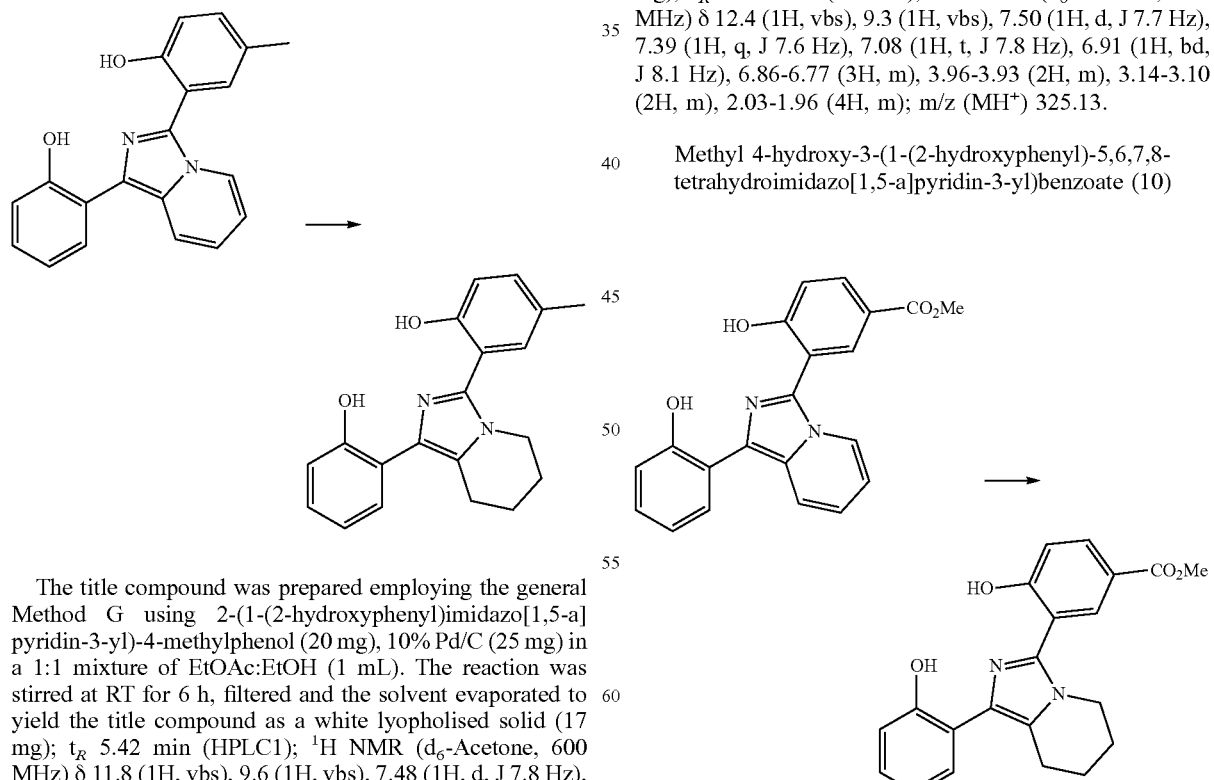

The title compound was prepared employing the general Method G using 3-fluoro-2-(1-(2-hydroxyphenyl)imidazo[1,5-a]pyridin-3-yl)phenol (15 mg), 10% Pd/C (10 mg) in a 1:1 mixture of EtOAc:EtOH (1 mL). The reaction was stirred at RT for 5 h, filtered and the solvent evaporated to yield the title compound as a white lyopholised solid (14 mg); $t_R$ 5.29 min (HPLC1); $^1$H NMR ($d_6$-Acetone, 600 MHz) δ 12.4 (1H, vbs), 9.3 (1H, vbs), 7.50 (1H, d, J 7.7 Hz), 7.39 (1H, q, J 7.6 Hz), 7.08 (1H, t, J 7.8 Hz), 6.91 (1H, bd, J 8.1 Hz), 6.86-6.77 (3H, m), 3.96-3.93 (2H, m), 3.14-3.10 (2H, m), 2.03-1.96 (4H, m); m/z (MH$^+$) 325.13.

Methyl 4-hydroxy-3-(1-(2-hydroxyphenyl)-5,6,7,8-tetrahydroimidazo[1,5-a]pyridin-3-yl)benzoate (10)

The title compound was prepared employing the general Method G using methyl 4-hydroxy-3-(1-(2-hydroxyphenyl)

imidazo[1,5-a]pyridin-3-yl)benzoate (20 mg), 10% Pd/C (10 mg) in a 1:1 mixture of EtOAc:EtOH (1 mL). The reaction was stirred at RT for 5 h, filtered and the solvent evaporated to yield the title compound as a white lyopholised solid (18 mg); $t_R$ 5.33 min (HPLC1); $^1$H NMR ($d_6$-Acetone, 600 MHz) δ 11.1 (1H, vbs), 8.16 (1H, d, J 2.0 Hz), 7.96 (1H, d, J 7.0 Hz), 7.47 (1H, d, J 8.0 Hz), 7.14-7.08 (2H, m), 6.90-6.83 (2H, m), 4.15 (2H, bt, J 5.7 Hz), 3.85 (3H, s), 3.08 (2H, bt, J 6.3 Hz), 2.03-1.93 (4H, m); m/z (MH$^+$) 365.15.

2-(3-(Pyridin-2-yl)-5,6,7,8-tetrahydroimidazo[1,5-a]pyridin-1-yl)phenol (11)

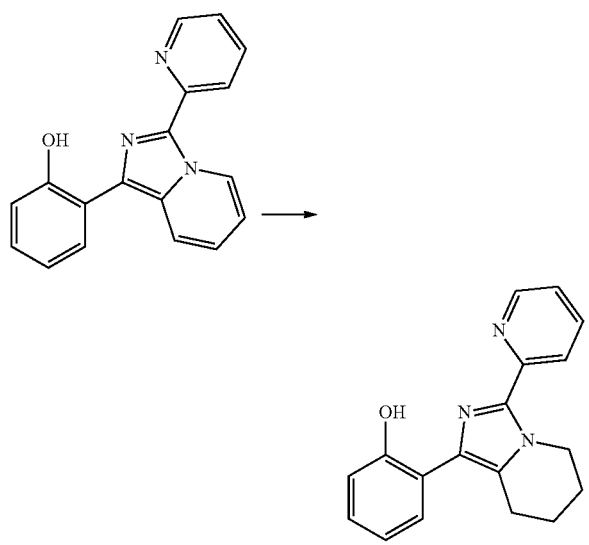

The title compound was prepared employing the general Method G using 2-(3-(pyridin-2-yl)imidazo[1,5-a]pyridin-1-yl)phenol (10 mg), 10% Pd/C (5 mg) in a 1:1 mixture of EtOAc:EtOH (1 mL). The reaction was stirred at RT for 5 h, filtered and the solvent evaporated to yield the title compound as a white lyopholised solid (5 mg); $t_R$ 5.21 min (HPLC1); $^1$H NMR ($d_6$-Acetone, 600 MHz) δ 12.6 (1H, bs), 8.65 (1H, bd, J 4.8 Hz), 8.09 (1H, d, J 8.0 Hz), 7.93 (1H, dt, J 1.4, 7.6 Hz), 7.52 (1H, dd, J 1.3, 7.8 Hz), 7.36 (1H, dd, J 6.0, 7.5 Hz), 7.11 (1H, dt, J 1.3, 8.3 Hz), 6.89 (1H, d, J 8.2 Hz), 6.85 (1H, t, J 7.5 Hz), 4.68 (2H, t, J 6.0 Hz), 3.15 (2H, t, J 6.4 Hz), 2.08-2.04 (2H, m), 2.00-1.96 (2H, m); m/z (MH$^+$) 292.14.

Synthesis of 2-(1-(2-hydroxyphenyl)-5,6,7,8-tetrahydroimidazo[1,5-a]pyridin-3-yl)-6-(morpholinomethyl)phenol (12)

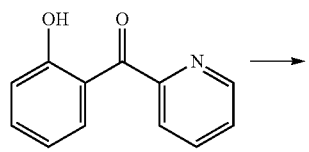

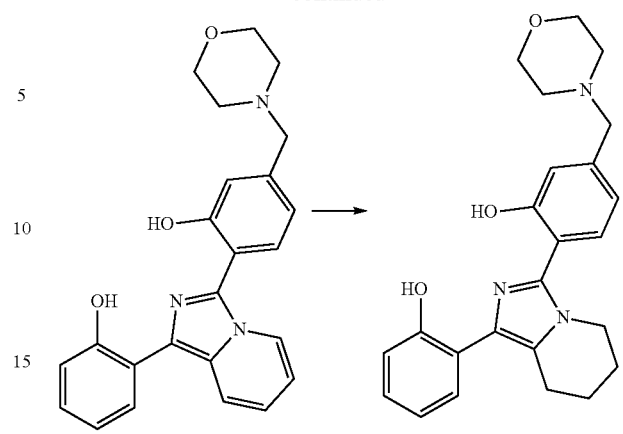

2-(1-(2-Hydroxyphenyl)imidazo[1,5-a]pyridine-3-yl)-5-(morpholinomethyl)phenol

2-Hydroxy-4-(morpholinomethyl)benzaldehyde (0.26 g, 1.2 mmol), (2-hydroxyphenyl)(pyridine-2-yl)methanone (1.2 g, 6.0 mmol) and NH$_4$OAc (2.3 g, 30.0 mmol) were suspended in AcOH (3 mL) and reacted according to the general Method F. The crude product was isolated by extraction with EtOAc (×3). The brown gum obtained was absorbed onto silica (0.5 g) and purified by silica chromatography (12 g) eluting with 0-100% EtOAc in hexane over 25CV, followed by EtOAc (20CV). A solid was obtained that was sonicated in EtOAc, filtered, washed with ether and air dried. A pale-yellow solid resulted (120 mg, 50%). HPLC (230 nm; HPLC2) $t_R$ 8.68 (99%) min. $^1$H NMR ($d_6$-DMSO, 600 MHz) δ 12.01 (1H, s), 10.38 (1H, s), 8.08 (1H, d, J 9.6 Hz), 7.85 (2H, m), 7.45 (1H, d, 7.8 Hz), 7.12 (1H, td, J 1.8, 9.0 Hz), 7.05 (1H, s), 7.00 (1H, dd, J 5.4, 9.0 Hz), 6.94-6.90 (3H, m), 6.82 (1H, t, J 7.2 Hz), 3.58 (4H, s), 3.47 (2H, s), 2.47 (4H, s). MS: m/z (MH$^+$) 402.18.

2-(1-(2-Hydroxyphenyl)-5,6,7,8-tetrahydroimidazo[1,5-a]pyridin-3-yl)-6-(morpholinomethyl)phenol (12)

2-(1-(2-Hydroxyphenyl)imidazo[1,5-a]pyridine-3-yl)-5-(morpholinomethyl)phenol (47.0 mg, 0.12 mmol) was suspended in MeOH (7 mL) and THF (7 mL) to which was added palladium on carbon (10 wt %) (10 mg) and reacted according to the general Method G for 17 h. A cream solid resulted which was sonicated in EtOAc, filtered, washed with EtOAc and air dried to afford the title compounds as a white solid (21.0 mg, 45%). HPLC (230 nm; HPLC2) $t_R$ 11.13 (99%) min. $^1$HNMR ($d_6$-DMSO, 600 MHz) δ 7.41 (1H, dd, J 1.2, 7.8 Hz), 7.18 (1H, d, 7.8 Hz), 7.04 (1H, td, J 1.2, 7.8 Hz), 6.82-6.78 (2H, m), 6.77 (1H, s), 6.70 (1H, d, 7.8 Hz), 3.89 (2H, s), 3.00 (2H, s), 2.47 (4H, s), 2.26 (4H, s), 1.84 (6H, s). MS: m/z (MH$^+$) 406.21.

Synthesis of 3-(3-(2-hydroxy-5-methylphenyl)-5,6,7,8-tetrahydroimidazo[1,5-a]pyridine-1-yl)pyridine-2-ol (13), 3-(3-(3-chloro-2-hydroxyphenyl)-5,6,7,8-tetrahydroimidazo[1,5-a]pyridin-1-yl)pyridin-2-ol (14) and 3-(3-(2-hydroxyphenyl)-5,6,7,8-tetrahydroimidazo[1,5-a]pyridin-1-yl)pyridin-2-ol (15)

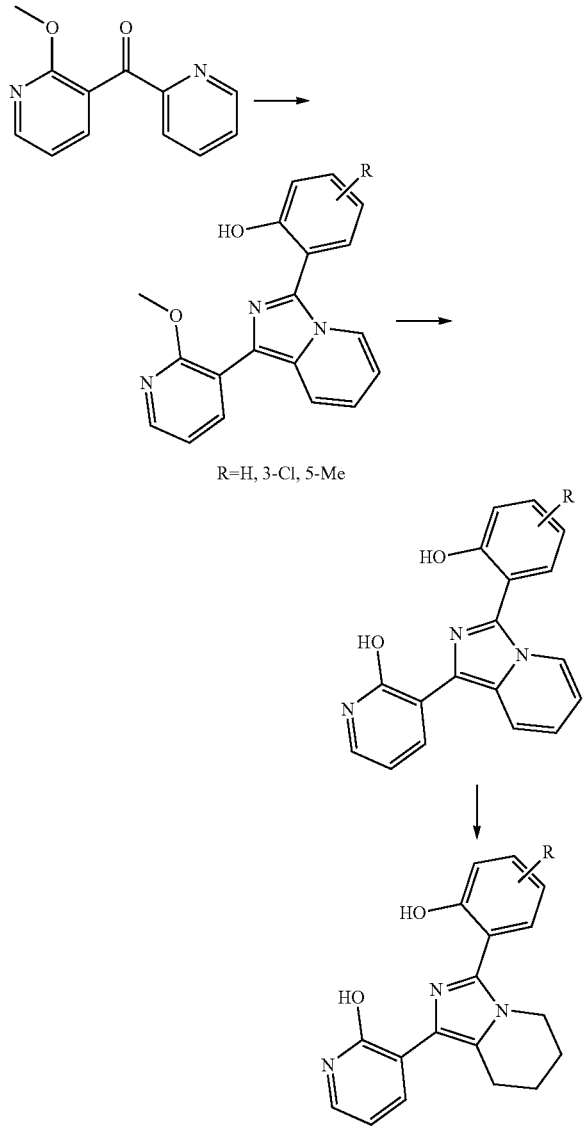

R=H, 3-Cl, 5-Me 3-(3-(2-Hydroxy-5-methylphenyl)-5,6,7,8-tetrahydroimidazo[1,5-a]pyridine-1-yl)pyridine-2-ol (13)

2-(1-(2-Methoxypyridin-3-yl)imidazo[1,5-a]pyridin-3-yl)-4-methylphenol (2-Methoxypyridin-3-yl)(pyridin-2-yl)methanone (0.15 g, 0.70 mmol), 5-methylsalicylaldehyde (0.29 g, 2.1 mmol) and NH$_4$OAc (0.2 g, 3.5 mmol) were suspended in AcOH (4.0 mL) and reacted according to the general Method F. The product was isolated by extraction with EtOAc (×3). The yellow solid obtained was purified on silica (12 g), eluting with 0-30% EtOAc in hexane (30CV) to afford a pale-yellow solid (0.14 g, 59%). HPLC (280 nm; HPLC2) t$_R$ 8.60 (99%) min. $^1$H NMR (CDCl$_3$, 600MHZ) δ 8.45 (1H, bd, J 4.2 Hz), 8.20 (1H, dd, 1.8, 4.8 Hz), 8.05 (1H, d, J 6.6 Hz), 7.70 (1H, td, J 1.2, 9.6 Hz), 7.53 (1H, s), 7.12-7.03 (3H, m), 6.88 (1H, dd, J 6.6, 8.4 Hz), 6.75 (1H, t, J 7.2 Hz), 4.05 (3H, s), 2.37 (3H, s). MS: m/z (MH$^+$) 332.14.

3-(3-(2-Hydroxy-5-methylphenyl)imidazo[1,5-a]pyridin-1-yl)pyridin-2-ol 2-(1-(2-Methoxypyridin-3-yl)imidazo[1,5-a]pyridin-3-yl)-4-methylphenol (0.13 g, 0.40 mmol) was heated in a 48% HBr$_{(aq)}$ (0.5 mL) at 120° C. for 17 h, according to the general Method D(i). The solid obtained was treated with a saturated aqueous solution of NaHCO$_3$ (10 mL) and sonicated to gain a uniform suspension, then filtered and the residue was washed with water (×2), hexane (×1), ether (×1) and air dried. A yellow coloured solid was obtained (108 mg, 85%). HPLC (280 nm; HPLC2) t$_R$ 7.66 (98%) min. $^1$H NMR (CDCl3, 600 MHz) δ 12.21 (1H, s), 10.59 (1H, s), 8.06 (1H, d, J 9.6 Hz), 7.99 (1H, d, 6.6 Hz), 7.95 (1H, d, J 7.2 Hz), 7.54 (1H, d, J 6.0 Hz), 7.40 (1H, s), 7.32 (1H, d, J 7.8 Hz), 7.16 (1H, t, J 7.2 Hz), 7.01-7.05 (2H, m), 6.43 (1H, t, J 6.6 Hz), 2.29 (3H, s). MS: m/z (MH$^+$) 318.12.

3-(3-(2-Hydroxy-5-methylphenyl)-5,6,7,8-tetrahydroimidazo[1,5-a]pyridine-1-yl)pyridine-2-ol (13)

3-(3-(2-Hydroxy-5-methylphenyl)imidazo[1,5-a]pyridin-1-yl)pyridin-2-ol (0.02 g, 0.06 mmol) was dissolved in MeOH (2 mL) and EtOAc (2 mL), to which was added palladium on carbon (10 wt %) (2 mg). The reaction was conducted according to the general Method G, and stirred at RT for 1.5 h. A grey solid was obtained (17.1 mg, 84%). HPLC (280 nm; HPLC2) IR 7.55 (94%) min. $^1$H NMR (CDCl3, 600 MHz) δ 7.83 (1H, d, J 6.6 Hz), 7.48 (1H, d, 6.0 Hz), 7.28 (1H, s), 7.22 (1H, d, J 8.4 Hz), 6.88 (1H, d, J 8.4 Hz), 6.51 (1H, t, J 6.0 Hz), 4.09 (2H, t, J 6.0 Hz), 2.95 (2H, t, J 6.6 Hz), 2.30 (3H, s), 2.00 (2H, m), 1.92 (2H, m). MS: m/z (MH$^+$) 322.16.

3-(3-(3-Chloro-2-hydroxyphenyl)-5,6,7,8-tetrahydroimidazo[1,5-a]pyridin-1-yl)pyridin-2-ol (14) and 3-(3-(2-hydroxyphenyl)-5,6,7,8-tetrahydroimidazo[1,5-a]pyridin-1-yl)pyridin-2-ol (15)

2-Chloro-6-(1-(2-methoxypyridin-3-yl)imidazo[1,5-a]pyridin-3-yl)phenol (2-Methoxypyridin-3-yl)(pyridin-2-yl)methanone (0.15 g, 0.70 mmol), 3-chloro-2-hydroxybenzaldehyde (0.33 g, 2.1 mmol) and NH$_4$OAc (0.26 g, 3.5 mmol) were suspended in AcOH (4.0 mL) and reacted according to the general Method F. The product was isolated by extraction with EtOAc (×3). The yellow solid obtained was purified on silica (12 g), eluting with 0-30% EtOAc in hexane (30CV) to afford a pale-yellow solid (0.17 g, 70%). HPLC (280 nm; HPLC2) t$_R$ 8.77 (92%) min. $^1$H NMR (CDCl$_3$, 600 MHz) δ 8.48 (1H, d, J 7.2 Hz), 8.21 (1H, dd, 1.8, 5.4 Hz), 8.04 (1H, dd, J 1.8, 7.2 Hz), 7.75 (1H, dt, J 1.2, 9.0 Hz), 7.71 (1H, dd, J 1.2, 7.8 Hz), 7.41 (1H, dd, J 1.2, 7.8 Hz), 7.04 (1H, dd, J 4.8, 7.2 Hz), 6.97 (1H, t, J 7.8 Hz), 6.91 (1H, ddd, J 0.6, 6.6, 9.0 Hz), 6.78 (1H, td, J 1.2, 7.8 Hz), 4.06 (3H, s). MS: m/z (MH$^+$) 352.08.

3-(3-(3-Chloro-2-hydroxyphenyl)imidazo[1,5-a]pyridin-1-yl)pyridin-2-ol

2-Chloro-6-(1-(2-methoxypyridin-3-yl)imidazo[1,5-a]pyridin-3-yl)phenol (0.16 g, 0.46 mmol) was heated in a 48% HBr$_{(aq)}$ (0.5 mL) at 120° C. for 17 h according to the general Method D(i). The obtained solid was treated with a saturated aqueous solution of NaHCO$_3$ (10 mL) and sonicated to gain a uniform suspension, then filtered and the residue was washed with water (×2), hexane (×2), ether (×2) and air dried. A yellow coloured solid was obtained (15 mg, 100%). HPLC (280 nm; HPLC2) t$_R$ 7.45 (100%) min. $^1$H NMR (d$_6$-DMSO, 600 MHz) δ 11.67 (1H, s), 8.11 (1H, d, J 9.6 Hz), 7.97 (1H, dd, 1.8, 6.6 Hz), 7.83 (1H, bs), 7.30 (1H, bs), 7.20 (1H, bs), 1.65 (1H, bs), 6.72 (1H, t, J 7.2 Hz), 6.54 (1H, bs), 6.32 (1H, bs), 6.18 (1H, bs). MS: m/z (MH$^+$) 338.07.

3-(3-(3-Chloro-2-hydroxyphenyl)-5,6,7,8-tetrahydroimidazo[1,5-a]pyridin-1-yl)pyridin-2-ol (14) and 3-(3-(2-hydroxyphenyl)-5,6,7,8-tetrahydroimidazo[1,5-a]pyridin-1-yl)pyridin-2-ol (15)

3-(3-(3-Chloro-2-hydroxyphenyl)imidazo[1,5-a]pyridin-1-yl)pyridin-2-ol (46 mg, 0.14 mmol) was suspended in MeOH (10 mL) and EtOAc (10 mL), to which was added palladium on carbon (10 wt %) (2 mg) and reacted according to the general Method G, for 48 h. The grey solid was loaded on to silica (0.5 g) and purified by column chromatography (silica, 4 g) eluting with 0 to 10% MeOH in DCM (100CV). 3-(3-(3-chloro-2-hydroxyphenyl)-5,6,7,8-tetrahydroimidazo[1,5-a]pyridin-1-yl)pyridin-2-ol (6.5 mg, 16%) was obtained as a yellow solid. HPLC (280 nm; HPLC2) t$_R$ 9.10 (84%) min. $^1$H NMR (CDCl$_3$, 600 MHz) δ 7.81 (1H, dd, J 1.8, 7.2 Hz), 7.49 (1H, d, 7.8 Hz), 7.37 (1H, dd, J 1.8, 6.6 Hz), 7.32 (1H, d, J 8.4 Hz), 6.81 (1H, t, J 7.8 Hz), 7.37 (1H, t, J 6.6 Hz), 4.28 (2H, m), 3.05 (2H, m), 2.05 (2H, m), 1.9 (2H, m). MS: m/z (MH$^+$) 342.10. 3-(3-(2-Hydroxyphenyl)-5,6,7,8-tetrahydroimidazo[1,5-a] pyridin-1-yl)pyridin-2-ol was also obtained as a white solid (4.8 mg, 10%). HPLC (280 nm; HPLC2) t$_R$ 8.66 (99%) min. $^1$H NMR (CDCl$_3$, 600 MHz) δ 7.81 (1H, d, J 6.0 Hz), 7.55 (1H, d, 7.8 Hz), 7.37 (1H, d, J 6.0 Hz), 7.22 (1H, m), 7.08 (1H, d, J 7.8 Hz), 6.87 (1H, t, J 7.2 Hz), 6.38 (1H, t, J 6.6 Hz), 4.29 (2H, t, J 6.0 Hz), 3.05 (2H, t, J 6.6 Hz), 2.03-2.00 (2H, m), 1.92-1.89 (2H, m). MS: m/z (MH$^+$) 308.14.

The following compounds were prepared in a similar manner. IDC-76 TRE

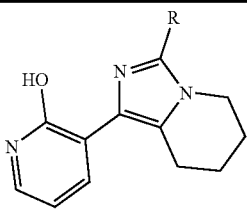

| ID | R = | MS m/z (MH$^+$) |
|---|---|---|
| 16 | HO-phenyl-F | 326.13 |
| 17 | HO-phenyl-CH$_2$-morpholine | 407.21 |

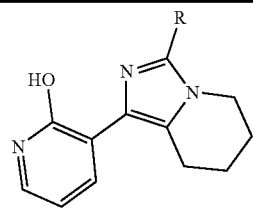

| ID | R = | MS m/z (MH$^+$) |
|---|---|---|
| 18 | HO-phenyl-CH$_2$CH$_2$-N(Et)$_2$ | 407.24 |
| 19 | HO-phenyl-CH$_2$CH$_2$-morpholine | 421.22 |
| 20 | HO-phenyl-CH$_2$CH$_2$CH$_2$-N(Et)$_2$ | 421.26 |

Synthesis of 4-(3-(2-hydroxyphenyl)-5,6,7,8-tetrahydroimidazo[1,5-a]pyridin-1-yl)pyridin-3-ol (21) and 4-(3-(3-(2-(diethylamino)ethyl)-2-hydroxyphenyl)-5,6,7,8-tetrahydroimidazo[1,5-a]pyridin-1-yl)pyridin-3-ol (22)

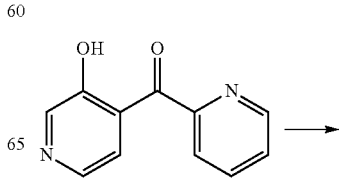

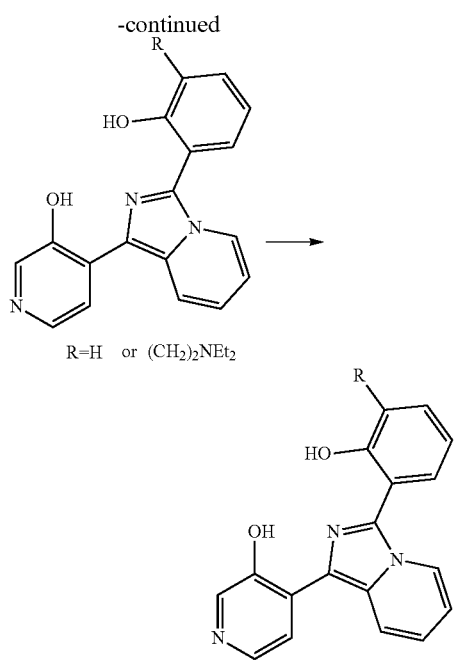

4-(3-(2-Hydroxyphenyl)imidazo[1,5-a]pyridin-1-yl)pyridin-3-ol (3-hydroxypyridin-4-yl)(pyridin-2-yl)methanone. (0.05 g, 0.24 mmol), salicylaldehyde (0.09 g, 0.72 mmol) and NH₄OAc (0.09 g, 1.2 mmol) were suspended in AcOH (2.5 mL) and reacted according to the general Method F. The crude product was isolated by extraction with EtOAc (×3). The obtained solid was sonicated in hexane/ether to afford on filtration and drying a yellow solid (48 mg, 66%). HPLC (280 nm; HPLC2) t$_R$ 7.95 (95%) min. ¹H NMR (d₆-DMSO, 500 MHz) δ 12.16 (1H, bs), 10.37 (1H, bs), 8.25-8.24 (2H, m), 8.11 (1H, d, J 5.0 Hz), 7.93 (1H, d, J 7.0 Hz), 7.86 (1H, d, J 5.5 Hz), 7.53 (1H, d, J 6.5 Hz), 7.44 (1H, t, J 8.0 Hz), 7.17 (1H, dd, J 6.5, 9.0 Hz), 7.09 (1H, d, J 8.0 Hz), 7.05 (1H, t, J 7.5 Hz), 6.92 (1H, t, J 5.5 Hz). MS: m/z (MH⁺) 304.11.

4-(3-(2-Hydroxyphenyl)-5,6,7,8-tetrahydroimidazo[1,5-a]pyridin-1-yl)pyridin-3-ol (21)

4-(3-(2-hydroxyphenyl)imidazo[1,5-a]pyridin-1-yl)pyridin-3-ol (0.2 g, 0.73 mmol) was suspended in MeOH (10 mL) and EtOAc (10 mL), to which was added 10% palladium on carbon (20 mg) and reacted according to the Method G, for 48 h. A brown solid resulted which was sonicated in EtOAc to afford 4-(3-(2-hydroxyphenyl)-5,6,7,8-tetrahydroimidazo[1,5-a] pyridin-1-yl)pyridin-3-ol (84.0 mg, 37%) as a yellow solid. HPLC (254 nm; HPLC2) t$_R$ 7.94 (94%) min. ¹H NMR (d₆-DMSO, 500 MHz) δ 8.13 (1H, s), 8.00 (1H, d, 5.4 Hz), 7.37 (1H, d, J 4.8 Hz), 7.33-7.30 (2H, m), 6.99 (1H, d, J 7.8 Hz), 6.90 (1H, t, J 7.2 Hz), 3.89 (2H, s), 3.09 (2H, bs), 1.89 (4H, bs), 1.9 (2H, m). MS: m/z (MH⁺) 308.14.

4-(3-(3-(2-(Diethylamino)ethyl)-2-hydroxyphenyl)imidazo[1,5-a]pyridin-1-yl)pyridin-3-ol (22)

(3-hydroxypyridin-4-yl)(pyridin-2-yl)methanone (0.05 g, 0.26 mmol), 3-(2-diethylamino)ethyl-2-hydroxybenzaldehyde (0.12 g, 0.52 mmol) and NH₄OAc (0.10 g, 1.3 mmol) were suspended in AcOH (3.0 mL) and reacted according to the Method F. The crude product was isolated by extraction with EtOAc (×3). Chromatography on silica (4 g), eluting with hexane (2CV), 0-100% EtOAc in hexane (20CV) and finally EtOAc (50CV) afforded a yellow oil/gum. A yellow solid was obtained that was identified as 4-(3-(3-(2-(diethylamino)ethyl)-2-hydroxyphenyl)imidazo[1,5-a]pyridin-1-yl)pyridin-3-ol after sonication in EtOAc (34 mg, 34%). HPLC (230 nm; HPLC2) t$_R$ 9.05 (99%) min. ¹H NMR (d₆-DMSO, 600 MHz) δ 12.30 (1H, bs), 8.22 (1H, d, J 9.6 Hz), 8.21 (1H, s), 8.08 (1H, d, J 4.8 Hz), 7.86 (1H, d, J 7.2 Hz), 7.84 (1H, d, J 4.8 Hz), 7.31 (1H, d, J 7.8 Hz), 7.23 (1H, d, J 7.8 Hz), 7.14 (1H, dd, J 6.6, 7.2 Hz), 6.87 (1H, t, J 7.2 Hz), 6.79 (1H, t, J 7.8 Hz), 2.88 (2H, t, J 3.6 Hz), 2.79 (2H, t, J 5.4 Hz), 2.68 (4H, q, J 7.2 Hz), 0.95 (6H, t, J 7.2 Hz) MS: m/z (MH⁺) 403.22.

4-(3-(3-(2-(Diethylamino)ethyl)-2-hydroxyphenyl)-5,6,7,8-tetrahydroimidazo[1,5-a]pyridin-1-yl)pyridin-3-ol (22)

4-(3-(3-(2-(Diethylamino)ethyl)-2-hydroxyphenyl)imidazo[1,5-a]pyridin-1-yl)pyridin-3-ol (0.02 g, 0.06 mmol) was suspended in MeOH (10 mL) and THF (10 mL), to which was added palladium on carbon (10 wt %) (2 mg) and reacted according to the general Method G, for 17 h. A grey solid resulted which was sonicated in ether to afford the title compound (8.0 mg, 37%) as a white solid. HPLC (230 nm; HPLC2) t$_R$ 7.89 (93%) min. ¹H NMR (d₆-DMSO, 500 MHz) δ 8.11 (1H, s), 8.00 (1H, d, 4.8 Hz), 7.37 (1H, d, J4.8 Hz), 7.16 (1H, dd, J 0.6, 7.2 Hz), 7.11 (1H, d, J 7.2 Hz), 6.19 (1H, t, J 7.2 Hz), 3.87 (2H, s), 3.09 (2H, m), 2.81 (2H, m), 2.71 (2H, m), 2.62 (4H, q, J 6.6 Hz), 1.85 (4H, m), 0.96 (6H, t, J 7.2 Hz). MS: m/z (MH⁺) 407.24.

Additional compounds prepared using same methodology IDA&4_TRE

| ID | R = | MS m/z (MH⁺) |
|---|---|---|
| 23 | 2-hydroxy-5-fluorophenyl | 326.13 |
| 24 | 2-hydroxy-3-fluorophenyl | 326.12 |

73
-continued

| ID | R = | MS m/z (MH+) |
|---|---|---|
| 25 | (morpholinoethyl-hydroxyphenyl) | 421.22 |
| 26 | (4-methylpiperazinyl-ethyl-hydroxyphenyl) | 434.25 |
| 27 | (hydroxy-morpholinomethyl-phenyl) | 407.20 |
| 28 | (morpholinopropyl-hydroxyphenyl) | 435.23 |

74

Synthesis of 3-(3-(2-hydroxyphenyl)-5,6,7,8-tetrahydroimidazo[1,5-a]pyridin-1-yl)pyridin-4-ol (29) and 3-(3-(3-fluoro-2-hydroxyphenyl)-5,6,7,8-tetrahydroimidazo[1,5-a]pyridin-1-yl)pyridin-4-ol (30)

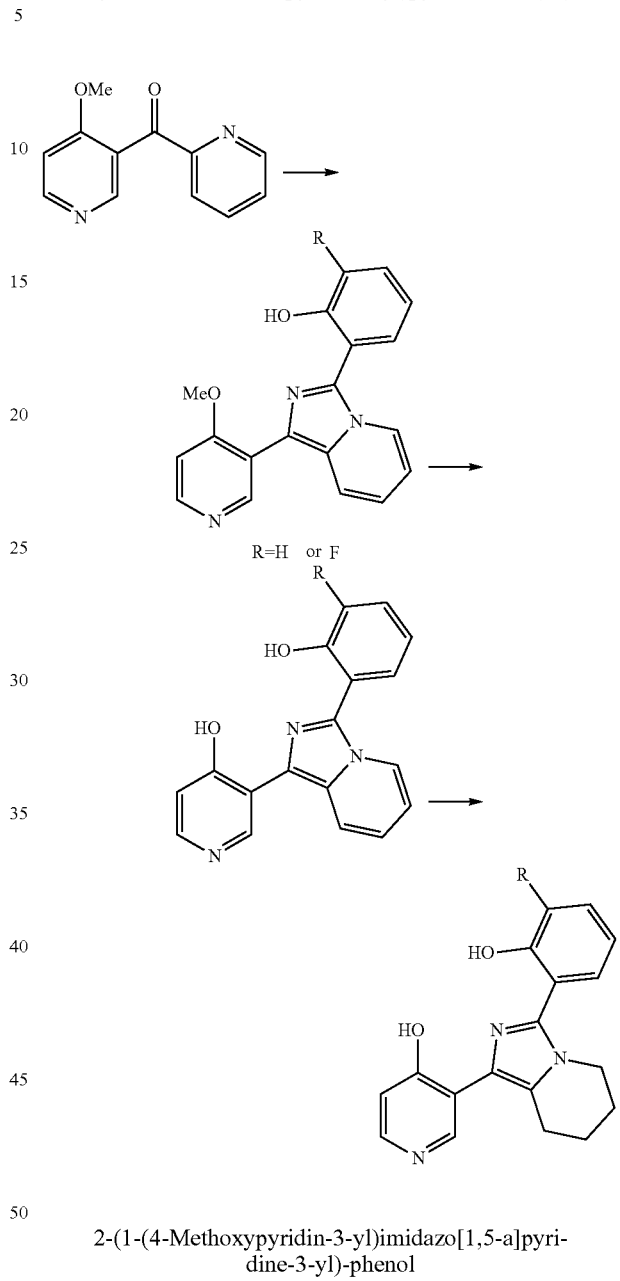

R=H or F

2-(1-(4-Methoxypyridin-3-yl)imidazo[1,5-a]pyridine-3-yl)-phenol (4-Methoxypyridin-3-yl)(pyridine-2-yl)methanone (0.24 g, 1.1 mmol), salicylaldehyde (0.41 g, 3.4 mmol) and NH₄OAc (0.26 g, 3.5 mmol) were suspended in AcOH (10.0 mL) and reacted according to the general Method F. The crude product was isolated by extraction with EtOAc (×3). The brown gum obtained was purified on silica (12 g), eluting with 0-100% EtOAc in hexane (15CV), then 100% EtOAc (15CV) to afford a yellow solid (166 mg, 36%). ¹H NMR (CDCl₃, 500MHZ) δ 8.81 (1H, s), 8.57 (1H, d, 6.0 Hz), 8.53 (1H, d, J 6.0 Hz), 7.81 (1H, dd, J 2.0, 8.0 Hz), 7.62 (1H, d, J 9.5 Hz), 7.33 (1H, dt, J 2.0, 8.5 Hz), 7.19 (1H, dd, J 1.0, 8.0 Hz), 7.03 (1H, dt, J 1.5, 9.0 Hz), 6.97 (1H, d, 6.0 Hz), 6.88 (1H, dd, J 6.5, 10.0 Hz), 6.75 (1H, dt, 1.5, 7.5 Hz), 3.98 (3H, s). MS: m/z (MH⁺) 318.12.

3-(3-(2-Hydroxyphenyl)imidazo[1,5-a]pyridin-1-yl)pyridin-4-ol 2-(1-(4-Methoxypyridin-3-yl)imidazo[1,5-a]pyridine-3-yl)-phenol (0.17 g, 0.52 mmol) was heated in a 48% aqueous solution of HBr (0.5 mL) and reacted according to the general Method D(i), at a temperature of 125° C. for 24 h. On workup the solid precipitate was isolated and not extracted with solvent. The pH was adjusted to pH6 before filtration. A yellow coloured solid was obtained (80 mg, 60%). $^1$H NMR (d$_6$-DMSO, 600 MHz) δ 10.4 (1H, bs), 8.39 (1H, s), 8.06 (1H, d, 9.6 Hz), 7.84 (1H, bd, J 6.6 Hz), 7.81 (1H, d, J 7.2 Hz), 7.51 (1H, d, J 6.6 Hz), 7.36 (1H, t, J 7.2 Hz), 7.04 (1H, d, J 7.8 Hz), 6.98 (1H, t, J 6.6 Hz), 6.81 (1H, t, J 7.2 Hz), 6.72 (1H, t, J 6.6 Hz), 6.53 (1H, bd, J 5.4 Hz).

3-(3-(2-Hydroxyphenyl)-5,6,7,8-tetrahydroimidazo[1,5-a]pyridin-1-yl)pyridin-4-ol (29)

3-(3-(2-Hydroxyphenyl)imidazo[1,5-a]pyridin-1-yl)pyridin-4-ol (0.08 g, 0.2 mmol) was suspended in MeOH (15 mL) and EtOAc (15 mL), to which was added palladium on carbon (10 wt %) (8 mg) and reacted according to the general Method G, for 72 h. A grey solid resulted which was loaded onto silica then purified by column chromatography (silica, 4 g), eluting with 0-15% MeOH in DCM (70CV). A clear gum/solid was obtained that was sonicated in ether/EtOAc to afford the title compound (10.0 mg, 12%) as a white solid. HPLC (254 nm; HPLC2) t$_R$ 7.14 (93%) min. $^1$H NMR (CD$_3$OD, 600 MHz) δ 8.09 (1H, s), 7.82 (1H, d, 7.2 Hz), 7.48 (1H, d, J 6.6 Hz), 7.42 (1H, t, J 7.8 Hz), 7.02-7.00 (2H, m), 6.57 (1H, d, J 7.2 Hz), 4.09 (2H, t, 5.4 Hz), 2.92 (2H, t, 6.6 Hz), 2.01 (2H, m), 1.93 (2H, m). MS: m/z (MH$^+$) 308.14.

3-(3-(3-Fluoro-2-hydroxyphenyl)-5,6,7,8-tetrahydro-imidazo[1,5-a]pyridin-1-yl)pyridin-4-ol (30)

2-Fluoro-6-(1-(4-methoxypyridin-3-yl)imidazo[1,5-a]pyridin-3-yl)phenol (4-Methoxypyridin-3-yl)(pyridin-2-yl)methanone (0.24 g, 1.1 mmol), 3-fluoro-2-hydroxybenzaldehyde (0.47 g, 3.4 mmol) and NH$_4$OAc (0.43 g, 5.6 mmol) were suspended in AcOH (10.0 mL) and reacted according to the general Method F. The crude product was isolated by extraction with EtOAc (×3). The brown gum obtained was purified on silica (12 g), eluting with 0-100% EtOAc in hexane (15CV), then 100% EtOAc (15CV) to afford a yellow solid (164 mg, 44%). $^1$H NMR (CDCl$_3$, 500 MHz) δ 8.79 (1H, s), 8.56-8.54 (2H, m), 7.66 (1H, d, J 9.5 Hz), 7.60 (1H, d, J 8.5 Hz), 7.16 (1H, t, J 9.0 Hz), 7.00-6.69 (2H, m), 6.92 (1H, t, J 7.0 Hz), 6.80 (1H, t, 6.0 Hz), 3.98 (3H, s). MS: m/z (MH$^+$) 336.11.

3-(3-(3-Fluoro-2-hydroxyphenyl)imidazo[1,5-a]pyridin-1-yl)pyridin-4-ol

2-Fluoro-6-(1-(4-methoxypyridin-3-yl)imidazo[1,5-a]pyridin-3-yl)phenol (0.16 g, 0.49 mmol) was heated in a 48% aqueous solution of HBr (0.5 mL) and reacted according to the general Method D(i), at a temperature of 125° C. for 24 h. On workup the precipitate was isolated not extracted with solvent. The pH was adjusted to pH6 before filtration. A yellow coloured solid was obtained (91 mg, 58%). $^1$H NMR (d$_6$-DMSO, 600 MHz) δ 8.19 (1H, bs), 8.05 (1H, d, J 9.0 Hz), 7.86 (1H, d, 7.2 Hz), 7.66 (1H, bs), 7.21 (1H, bs), 7.10 (1H, bs), 6.75 (1H, bs), 6.63 (1H, bs), 6.55 (1H, bs), 6.32 (1H, bs).

3-(3-(3-Fluoro-2-hydroxyphenyl)-5,6,7,8-tetrahydro-imidazo[1,5-a]pyridin-1-yl)pyridin-4-ol (30)

3-(3-(3-Fluoro-2-hydroxyphenyl)imidazo[1,5-a]pyridin-1-yl)pyridin-4-ol (0.09 g, 0.28 mmol) was suspended in MeOH (15 mL) and EtOAc (15 mL), to which was added palladium on carbon (10 wt %) (8 mg) and reacted according to the general Method G, for 17 h. A brown gum resulted which was sonicated in EtOAc/MeOH to afford a solid. This was further sonicated in THF to give the title compound (10.0 mg, 12%) as a grey solid. HPLC (254 nm; HPLC2) t$_R$ 7.85 (90%) min. $^1$HNMR (CD$_3$OD, 600 MHz) δ 8.09 (1H, s), 7.82 (1H, d, J 6.6 Hz), 7.32 (1H, d, 9.6 Hz), 7.30 (1H, d, J 7.8 Hz), 6.98-7.01 (1H, m), 6.58 (1H, d, J 7.2 Hz), 4.11-4.06 (2H, m), 2.93 (2H, t, J, 6.6 Hz), 2.02-2.04 (2H, m), 1.95-1.93 (2H, m). MS: m/z (MH$^+$) 326.13.

Synthesis of 2,2'-(6-(trifluoromethyl)-5,6,7,8-tetra-hydroimidazo[1,5-a]pyridine-1,3-diyl)diphenol (36)

R=H, R'=CF$_3$
R=Me, R'=Me
R=Me, R'=CF$_3$

2,2'-(6-(Trifluoromethyl)-5,6,7,8-tetrahydroimidazo[1,5-a]pyridine-1,3-diyl)diphenol (36)

To a solution of 2,2'-(6-(trifluoromethyl)imidazo[1,5-a]pyridine-1,3-diyl)diphenol (15 mg, 0.044 mmol) in MeOH (7 mL) was added 10% Pd/C (8 mg). The reaction was conducted as outline in the general Method G to afford the title compound as a light brown powder (4.0 mg, 24%). $^1$H NMR (CDCl$_3$, 600MHZ) δ 7.41 (1H, dd, J 1.2, 8.4 Hz), 7.37-7.33 (2H, m), 7.22-7.19 (1H, m), 7.10 (1H, dd, J 1.2, 8.4 Hz), 7.01 (2H, m), 6.91 (1H, dt, J 1.2, 7.2 Hz), 4.46 (1H, dq, J 5.4, 13.2 Hz), 4.17 (1H, t, J 11.4 Hz), 3.5-3.32 (1H, m), 3.15-3.09 (1H, m), 2.78-2.68 (1H, m), 2.45-2.40 (1H, m), 1.92 (1H, ddd, J 13.2, 5.4 Hz). MS: m/z (MH$^+$) 375.13.

2-(1-(2-Hydroxyphenyl)-6-methyl-5,6,7,8-tetrahydroimidazo[1,5-a]pyridin-3-yl)-4-methylphenol (37)

To a solution of 2-(1-(2-hydroxyphenyl)-6-methylimidazo[1,5-a]pyridin-3-yl)-4-methylphenol (12 mg, 0.03 mmol) in MeOH (7 mL) was added 10% Pd/C (9 mg). The reaction was conducted as outline in the general Method G to afford the title compound as a light grey powder (1.5 mg, 12%). $^1$H NMR (CDCl$_3$, 600MHZ) δ 10.01 (1H, bs), 9.90 (1H, s), 7.58-7.52 (1H, m), 7.37 (1H, d, J 7.8 Hz), 7.24 (1H, m), 7.18 (1H, t, J 7.2 Hz), 7.11 (1H, d, J 7.8 Hz), 7.04-6.98 (1H, m), 6.92 (1H, t, J 7.2 Hz), 4.32-4.28 (1H, m), 4.21-4.15 (1H, m), 3.23-3.18 (1H, m), 2.67-2.62 (1H, m), 2.34 (3H, s), 2.10 (1H, d, J 13.0 Hz), 2.08-2.01 (1H, m), 1.67-1.62 (1H, m), 1.24 (3H, d, J 6.0 Hz). MS: m/z (MH$^+$) 335.17.

2-(1-(2-Hydroxyphenyl)-6-(trifluoromethyl)-5,6,7,8-tetrahydroimidazo[1,5-a]pyridin-3-yl)-4-methylphenol (38)

To a solution of 2-(1-(2-hydroxyphenyl)-6-(trifluoromethyl)imidazo[1,5-a]pyridin-3-yl)-4-methylphenol (21 mg, 0.054 mmol) in MeOH (8 mL) was added 10% Pd/C (11 mg). The reaction was conducted as outline in the general Method G to afford the title compound as a pink solid (10 mg, 20%). $^1$H NMR (CDCl$_3$, 600 MHz) δ 9.77 (2H, bs), 7.34 (1H, d, J 7.2 Hz), 7.21 (1H, t, J 7.2 Hz), 7.19-7.14 (2H, m), 7.01 (2H, t, J 9.0 Hz), 6.92 (1H, t, J 7.2 Hz), 4.43 (1H, dd, J 4.2, 12.0 Hz), 4.16 (1H, t, J 12.0 Hz), 3.36-3.32 (1H, m), 3.15-3.10 (1H, m), 3.12-3.08 (1H, m), 2.77-2.73 (1H, m), 2.37 (3H, s), 1.96-1.92 (1H, m). MS: m/z (MH$^+$) 389.14.

Synthesis of 2-(1-(2-methoxypyridin-3-yl)-6,7-dihydro-5H-pyrrolo[1,2-c]imidazol-3-yl)phenol

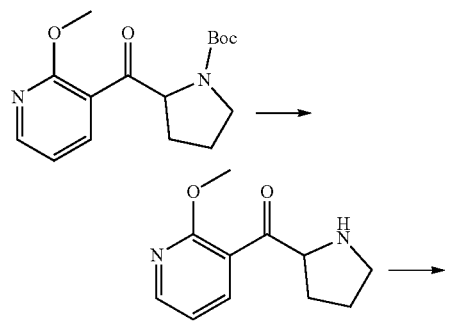

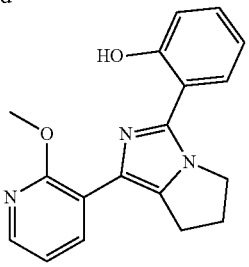

(2-Methoxypyridin-3-yl)(pyrrolidin-2-yl)methanone tert-Butyl 2-(2-methoxynicotinoyl)pyrrolidine-1-carboxylate (0.20 g, 0.66 mmol) was diluted with 1,4-dioxane (5 mL) containing 4M aqueous solution of HCl (0.66 mL). The solution was stirred at RT for 2.5 h. The reaction was made basic with a 2M aqueous solution of NaOH and extracted with DCM (15 mL×3), dried (Na$_2$SO$_4$), then concentrated under reduced pressure to give a brown gum (0.10 g) that was used directly in the next step. MS: m/z (MH$^+$) 207.11.

2-(1-(2-Methoxypyridin-3-yl)-6,7-dihydro-5H-pyrrolo[1,2-c]imidazol-3-yl)phenol (39)

(2-Methoxypyridin-3-yl)(pyrrolidin-2-yl)methanone (0.10 g, 0.48 mmol), salicylaldehyde (0.18 g, 1.5 mmol) and NH$_4$OAc (0.19 g, 2.4 mmol) were heated in AcOH (4.5 mL) and reacted according to the general Method F. The crude product was isolated by extraction with EtOAc (15 mL×3). The brown gum was loaded onto silica and purified by chromatography (silica, 12 g) eluting with hexane (3CV), 0-60% EtOAc in hexane (30CV) then 60-100% (20CV). 2-(1-(2-Methoxypyridin-3-yl)-6,7-dihydro-5H-pyrrolo[1,2-c]imidazol-3-yl)phenol was isolated as a tan solid (6.2 mg, 4%). $^1$HNMR (CDCl$_3$, 500 MHz) δ 8.14 (1H, dd, J 1.5, 7.5 Hz), 8.09 (1H, dd, J 1.5, 4.5 Hz), 7.57 (1H, J 1.0, 7.5 Hz), 7.24 (1H, dd, J 1.0, 8.0 Hz), 7.08 (1H, dd, J 1.0, 8.5 Hz), 6.99 (1H, dd, J 5.0, 7.5 Hz), 6.89 (1H, td, J 1.0, 8.0 Hz), 4.38 (2H, t, J 7.0 Hz), 4.04 (3H, s), 3.16 (2H, t, J 7.5 Hz), 2.73 (2H, m). MS: m/z (MH$^+$) 308.14.

Synthesis of 6,7-dihydro-5H-pyrrolo[1,2-c]imidazoles and 6,7,8,9-tetrahydro-5H-imidazo[1,5-a]azepines

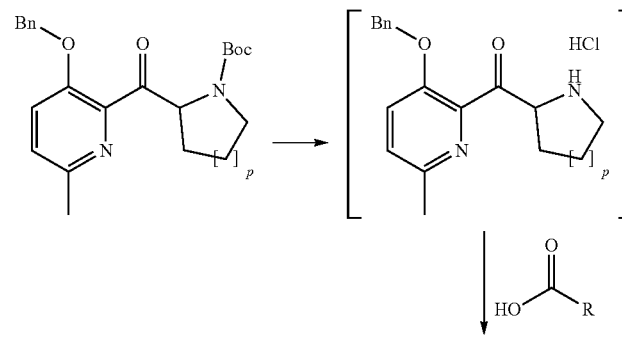

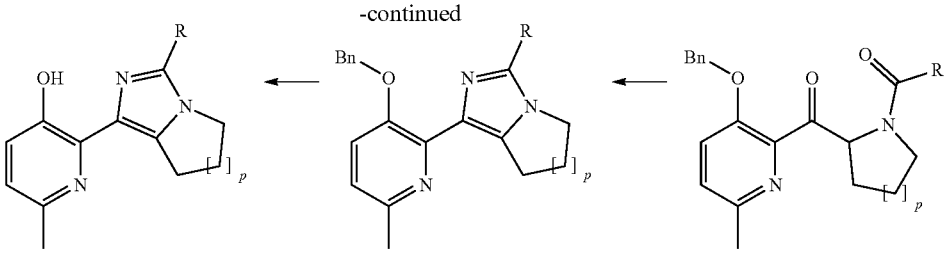

(2-(3-(Benzyloxy)-6-methylpicolinoyl)pyrrolidin-1-yl)(2-hydroxyphenyl)methanone (A)

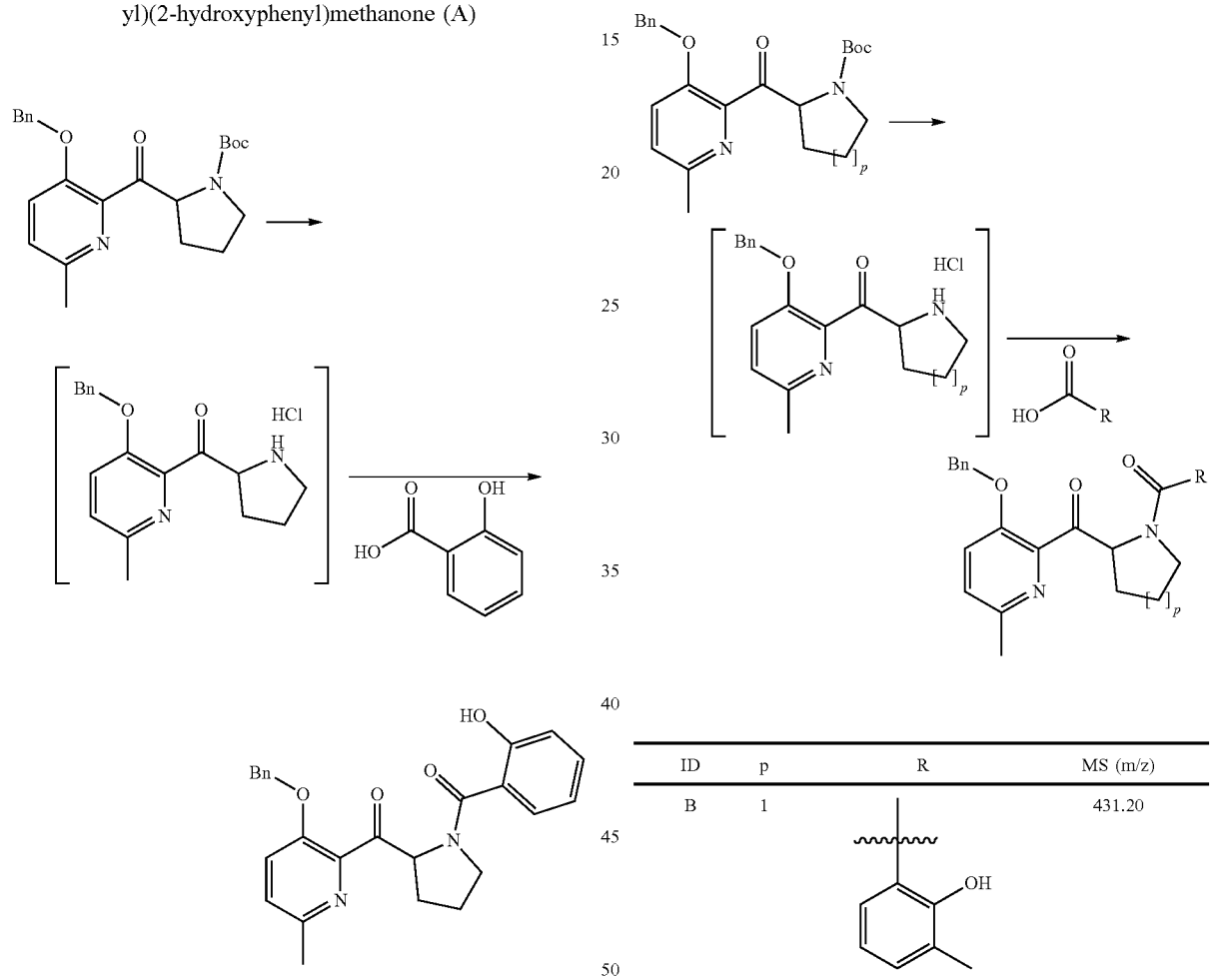

General Method J was used with CDI (106 mg) and salicylic acid (91 mg) in 1,4-dioxane (1 mL) for the acylating solution. Separately tert-butyl 2-(3-(benzyloxy)-6-methylpicolinoyl)pyrrolidine-1-carboxylate (130 mg) in 1,4-dioxane (1 mL) was treated with HCl in 1,4-dioxane (1 mL) at RT. The solid was isolated by trituration with an $Et_2O$/hexanes mixture. The residual solvent was removed in vacuo before the solid was re-suspended in 1,4-dioxane and used, along with the acylating solution, as described in the general method. When complete by MS, the reaction was processed in the way outlined and the crude product isolated (42 mg, m/z ($MH^+$) 417.18). The crude product was a mixture of both the target and the di-acylated target (m/z ($MH^+$) 537.20. The sample was used without further manipulation.

Using the same methodology, the following examples were also prepared.

-continued

| ID | p | R | MS (m/z) |
|---|---|---|---|
| E | 1 | 3-hydroxypyridin-2-yl | 418.17 |
| F | 3 | 2-hydroxyphenyl | 445.21 |
| G | 3 | 2-hydroxy-3-methylphenyl | 459.23 |
| H | 3 | 4-fluoro-2-hydroxyphenyl | 463.20 |
| I | 3 | 2-hydroxy-4-methylphenyl | 459.23 |
| J | 3 | 3-hydroxypyridin-2-yl | 446.21 |

2-(1-(3-(Benzyloxy)-6-methylpyridin-2-yl)-6,7-dihydro-5H-pyrrolo[1,2-c]imidazol-3-yl)phenol (40)

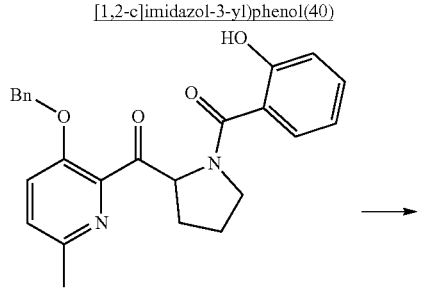

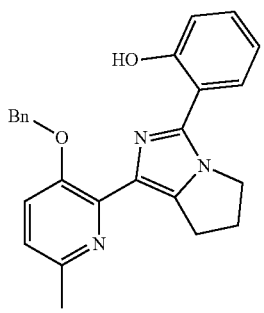

General Method F was used with (2-(3-(benzyloxy)-6-methylpicolinoyl)pyrrolidin-1-yl)(2-hydroxyphenyl)methanone A (42 mg) and NH₄OAc (10 eq) in AcOH (1 mL) with heating of the mixture at 50° C. for 40 h, after which time the reaction was partitioned between water and EtOAc with sufficient sat. NaCl$_{(aq)}$ to enable the organic layer to separate. The EtOAc layer was separated and the aqueous layer further extracted with EtOAc (3×) before the combined extracts were dried and the solvent evaporated to yield the crude product. The sample was adsorbed onto SiO₂ and purified on 4 g SiO₂ (254/280 nm) using EtOAc/hexanes gradient 0-0% 3CV, 0-100% 30CV with the target being identified by MS. The desired fractions were combined and the solvent evaporated to yield the title compound (26 mg) as a white solid. ¹H NMR (CDCl₃, 500MHZ) δ 9.1 (1H, vbs), 7.51 (1H, d, J 8.3 Hz), 7.41 (2H, d, J 7.5 Hz), 7.34 (2H, t, J 7.3 Hz), 7.31-7.26 (1H, m), 7.21 (1H, t, J 7.6 Hz), 7.11 (1H, d, J 8.5 Hz), 7.07 (1H, d, J 8.1 Hz), 6.90 (1H, d, J 8.4 Hz), 6.84 (1H, t, J 7.4 Hz), 5.18 (2H, s), 4.29 (2H, t, J 7.5 Hz), 3.01 (2H, t, J 7.5 Hz), 2.63 (2H, p, J 7.5 Hz), 2.50 (3H, s).

Using the same methodology, the following examples were also prepared.

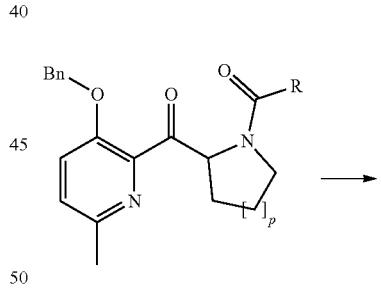

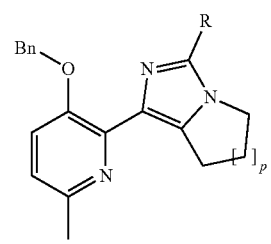

| No. | Ketone | p | R | MS/NMR |
|---|---|---|---|---|
| 41 | B | 1 | 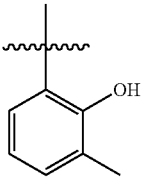 [SMILES: *c1cccc(C)c1O] | $^1$H NMR (CDCl$_3$, 500 MHz) δ 7.43 (2H, d, J 7.3 Hz), 7.40 (1H, d, J 7.7 Hz), 7.35 (2H, t, J 7.5 Hz), 7.33-7.28 (1H, m), 7.14 (1H, d, J 8.6 Hz), 7.09 (1H, d, J 7.1 Hz), 6.92 (1H, d, J 8.4 Hz), 6.76 (1H, t, J 7.3 Hz), 5.16 (2H, s), 4.30 (2H, t, J 7.1 Hz), 3.03 (2H, t, J 7.1 Hz), 2.63 (2H, p, J 7.2 Hz), 2.51 (3H, s), 2.32 (3H, s) |
| 42 | C | 1 | 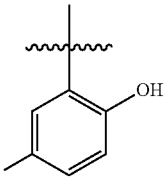 | $^1$H NMR (CDCl$_3$, 500 MHz) δ 7.41 (2H, d, J 7.0 Hz), 7.34 (2H, t, J 7.5 Hz), 7.32-7.28 (1H, m), 7.20 (1H, dd, J 9.5, 2.8 Hz), 7.12 (1H, d, J 8.5 Hz), 6.98 (1H, dd, J 8.9, 5.0 Hz), 6.94-6.89 (2H, m), 5.18 (2H, s), 4.28 (2H, t, J 7.3 Hz), 3.02 (2H, t, J 7.6 Hz), 2.65 (2H, p, J 7.5 Hz), 2.50 (3H, s) |
| 43 | D | 1 | 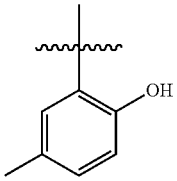 | $^1$H NMR (CDCl$_3$, 500 MHz) δ 7.41 (2H, d, J 7.6 Hz), 7.34 (2H, t, J 7.8 Hz), 7.32-7.27 (2H, m), 7.11 (1H, d, J 8.1 Hz), 7.02 (1H, d, J 8.1 Hz), 6.97 (1H, d, J 8.3 Hz), 6.90 (1H, d, J 8.3 Hz), 5.18 (2H, s), 4.32 (2H, t, J 7.2 Hz), 3.02 (2H, t, J 7.6 Hz), 2.64 (2H, p, J 7.3 Hz), 2.50 (3H, s), 2.31 (3H, s) |
| 44 | E | 1 | 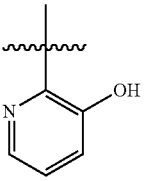 [SMILES: *c1ncccc1O] | $^1$H NMR (CDCl$_3$, 500 MHz) δ 8.08 (1H, dd, J 1.2, 4.4 Hz), 7.41 (2H, d, J 7.3 Hz), 7.35 (2H, t, J 7.6 Hz), 7.32-7.28 (2H, m), 7.14 (1H, d, J 8.3 Hz), 7.10 (1H, dd, J 8.3, 4.5 Hz), 6.93 (1H, d, J 8.4 Hz), 5.18 (2H, s), 4.53 (2H, t, J 7.2 Hz), 3.02 (2H, t, J 7.5 Hz), 2.59 (2H, p, J 7.2 Hz), 2.52 (3H, s); m/z 399.18 |
| 45 | F | 3 | 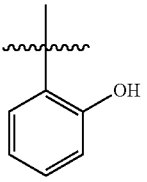 [SMILES: *c1ccccc1O] | m/z 426.22 |
| 46 | G | 3 | 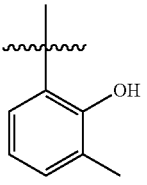 [SMILES: *c1cccc(C)c1O] | m/z 440.23 |
| 47 | H | 3 | 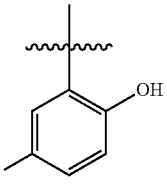 | m/z 444.21 |
| 48 | I | 3 | 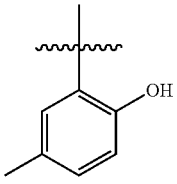 | m/z 440.23 |

-continued

| No. | Ketone | p | R | MS/NMR |
|---|---|---|---|---|
| 49 | J | 3 | 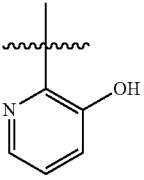 [SMILES: *c1ncccc1O] | m/z 427.21 |

2-(3-(2-Hydroxyphenyl)-6,7-dihydro-5H-pyrrolo[1,2-c]imidazol-1-yl)-6-methylpyridin-3-ol (50)

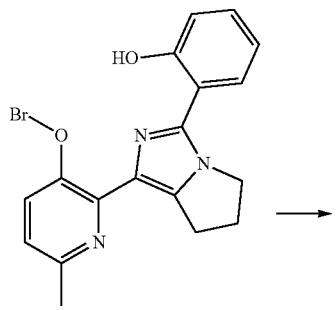

General Method G was used where 2-(1-(3-(benzyloxy)-6-methylpyridin-2-yl)-6,7-dihydro-5H-pyrrolo[1,2-c]imidazol-3-yl)phenol (40) (26 mg) was dissolved/suspended in EtOAc/EtOH (~1:2, 6 mL). 10% Pd/C (20 mg) was added and the system placed under atm of $H_{2(g)}$ for 30 min after which time MS indicated that the reaction was complete. The catalyst was filtered off and the solvent evaporated to yield the crude product. The sample was adsorbed onto $SiO_2$ and purified using MeOH/DCM gradient 0-0% 5CV, 0-5% 20CV. The target fractions were combined to yield the title compound as a pale yellow amorphous solid (6.5 mg). HPLC1 $t_R$ 5.74 min. $^1$HNMR ($d_6$-Acetone, 500 MHz) δ 10.5-10 (1H, bs), 7.65 (1H, dd, J 1.2, 7.8 Hz), 7.31 (1H, t, 7.5 Hz), 7.11 (1H, d, J 8.3 Hz), 7.03 (1H, d, J 8.2 Hz), 6.99 (1H, t, J 7.6 Hz), 6.94 (1H, d, J 8.2 Hz), 4.38 (2H, t, J 7.1 Hz), 3.26 (2H, t, J 7.3 Hz), 2.77 (2H, p, J 7.2 Hz), 2.42 (3H, s); m/z ($MH_+$) 308.14, ($M2H^{2+}$) 154.57.

Using the same methodology, the following examples were also prepared.

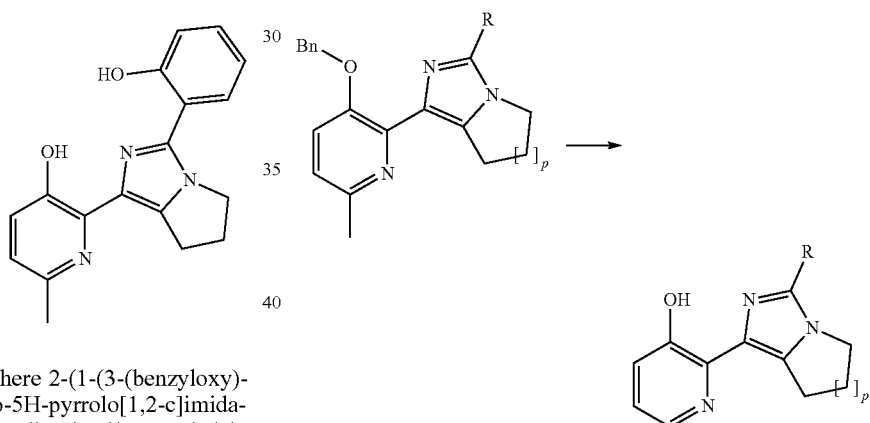

| ID | p | R | NMR/MS |
|---|---|---|---|
| 21 | 1 | 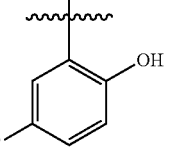 | $^1$H NMR ($d_6$-Acetone, 500 MHz) δ 10-10.4 (~2H, bs), 7.38 (1H, dd, J 3.0, 9.4 Hz), 7.12 (1H, d, J 8.2 Hz), 7.09 (1H, dt, J 3.0, 8.1 Hz), 7.03 (1H, dd, J 4.8, 8.9 Hz), 6.94 (1H, d, J 8.3 Hz), 4.40 (2H, t, J 7.1 Hz), 3.25 (2H, t, J 7.3 Hz), 2.77 (2H, p, J 7.2 Hz), 2.41 (3H, s); m/z (MH$^+$) 326.13, (MH$^{2+}$) 163.57 |
| 52 | 1 | 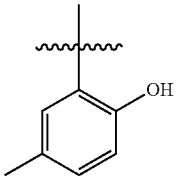 [SMILES: *c1cc(C)ccc1O] | $^1$H NMR ($d_6$-Acetone, 500 MHz) δ 10.6-9.7 (1H, bs), 7.45 (1H, s), 7.13-7.09 (2H, m), 6.94-6.91 (2H, m), 4.36 (2H, t J 7.1 Hz), 3.25 (2H, t J 7.3 Hz), 2.76 (2H, p, J 7.2 Hz), 2.41 (3H, s), 3.31 (3H, s); m/z (MH$^+$) 322.16, (M2H$^{2+}$) 161.58 |

-continued

| ID | p | R | NMR/MS |
|---|---|---|---|
| 53 | 1 | 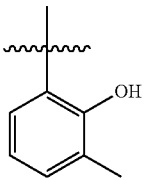 [SMILES: *c1cccc(C)c1O] | $^1$H NMR (d$_6$-Acetone, 500 MHz) δ 10.5-9.5 (2H, 2xbs), 7.54 (1H, d, J 7.8 Hz), 7.24-7.19 (1H, m), 7.15 (1H, d, J 8.3 Hz), 6.97 (1H, d, J 8.3 Hz), 6.90 (1H, t, J 7.6), 4.45 (2H, t, J 7.1 Hz), 3.28 (2H, t, J 7.4 Hz), 2.82-2.79 (2H, m), 2.43 (3H, s), 2.23 (3H, s); m/z (MH$^+$) 322.16, (M2H$^{2+}$) 161.58 |
| 54 | 1 | 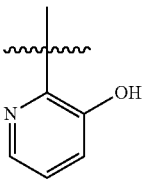 [SMILES: *c1ncccc1O] | $^1$H NMR (CDCl$_3$, 500 MHz) δ 8.18 (1H, d, J 4.4 Hz), 7.74 (1H, d, J 7.1 Hz), 7.21-7.14 (2H, m), 6.92 (1H, d, J 4.5 Hz), 4.60 (2H, t, J 7.3 Hz), 3.30 (2H, t, J 7.5 Hz), 2.34 (2H, p, J 7.3 Hz), 2.47 (3H, s,); m/z (MH$^+$) 309.13, (M2H$^{2+}$) 155.07 |
| 55 | 2 | 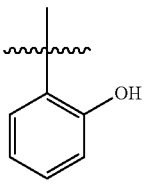 [SMILES: *c1ccccc1O] | $^1$H NMR (d$_6$-Acetone, 500 MHz) δ 12.56 (1H, bs), 8.85 (1H, bs), 7.41-7.36 (2H, m), 7.07-7.03 (1H, m), 7.04 (1H, d, J 8.2 Hz), 7.01 (1H, t, J 7.5 Hz), 6.91 (1H, d, J 8.2 Hz), 4.06-4.02 (2H, m), 3.88-3.64 (2H, bm), 2.41 (3H, s), 1.93-1.87 (2H, m), 1.87-1.81 (2H, m), 1.78-1.71 (2H, m); m/z (MH$^+$) 336.17, (M2H$^{2+}$) 168.59 |
| 56 | 3 | 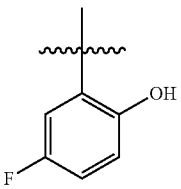 [SMILES: *c1cc(F)ccc1O] | $^1$H NMR (d$_6$-Acetone, 500 MHz) δ 7.19-7.12 (2H, m), 7.10-7.05 (1H, m), 7.05 (1H, d, J 8.3 Hz), 6.92 (1H, d, J 8.3 Hz), 4.08-4.03 (2H, m), 3.86-3.62 (2H, bm), 2.41 (3H, s), 1.93-1.87 (2H, m), 1.87-1.81 (2H, m), 1.78-1.70 (2H, m); m/z (MH$^+$) 354.16, (M2H$^{2+}$) 177.58 |
| 57 | 3 | 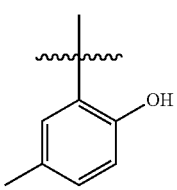 [SMILES: *c1cc(C)ccc1O] | $^1$H NMR (d$_6$-Acetone, 500 MHz) δ 12.3 (1H, vbs), 8.6 (1H, vbs), 7.21-7.15 (2H, m), 7.04 (1H, d, J 8.2 Hz), 6.97-6.92 (1H, m), 6.91 (1H, d, J 8.2 Hz), 4.08-4.00 (2H, m), 3.89-3.62 (2H, bm), 2.41 (3H, s), 2.30 (3H, s) 1.93-1.86 (2H, m), 1.86-1.80 (2H, m), 1.78-1.70 (2H, m); m/z (MH$^+$) 350.19, (M2H$^{2+}$) 175.60 |

2-(3-(3-Fluoro-2-hydroxyphenyl)-6,7-dihydro-5H-pyrrolo[1,2-c]imidazol-1-yl)-6-methylpyridin-3-ol (59)

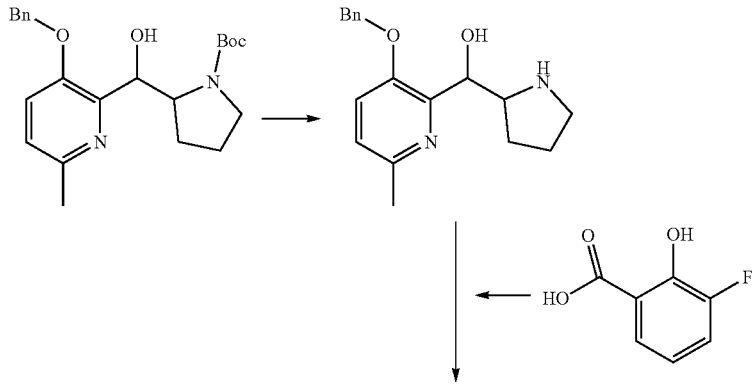

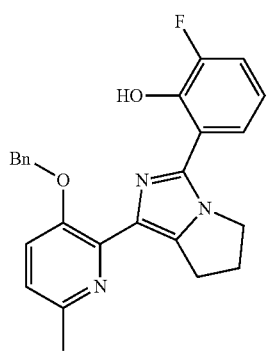 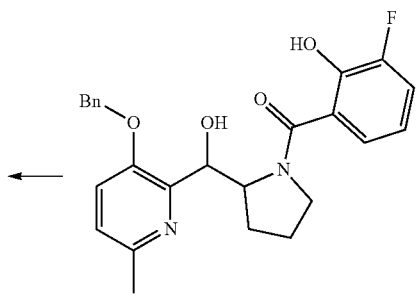

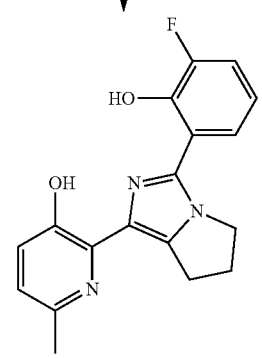

(3-(Benzyloxy)-6-methylpyridin-2-yl)(pyrrolidin-2-yl)methanol tert-Butyl 2-((3-(benzyloxy)-6-methylpyridin-2-yl)(hydroxy)methyl)pyrrolidine-1-carboxylate (245 mg) was dissolved in DCM (10 mL), cooled to 0° C. and then treated with TMSOTf (222 μL). The reaction was stirred for 1 h after which time the reaction was diluted with sat. NaHCO$_3$ (aq) and the DCM layer separated. The aqueous layer was further extracted with DCM (2×) before the combined extracts were dried and the solvent evaporated to yield the crude product (163 mg, m/z 299.175 (MH$^+$)) as a mixture of diastereomers which was used without further manipulation.

(2-((3-(Benzyloxy)-6-methylpyridin-2-yl) (hydroxy)methyl)pyrrolidin-1-yl) (3-fluoro-2-hydroxyphenyl)methanone Using the general Method I with CDI (90 mg) and 3-fluoro-2-hydroxybenzoic acid (117 mg). Once prepared the acylating agent was added to (3-(benzyloxy)-6-methylpyridin-2-yl)(pyrrolidin-2-yl)methanol (150 mg). The resultant solution was stirring for a total of 72 h after which time the title compound was the major product accompanied by a small amount of diacylated material. The reaction was processed as described in the general method to yield the crude title product (184 mg, m/z 437.187 (MH$^+$)) which was again used without further manipulation.

(2-(3-(Benzyloxy)-6-methylpicolinoyl)pyrrolidin-1-yl)(3-fluoro-2-hydroxyphenyl)methanone (2-((3-(Benzyloxy)-6-methylpyridin-2-yl)(hydroxy)methyl)pyrrolidin-1-yl)(2-hydroxyphenyl)methanone (93 mg) was dissolved in DMSO (1 mL) and treated with triethylamine (310 μL). Pyridine sulfur trioxide complex (354 mg) was dissolved in DMSO (1 mL) and allowed to sit for 5 min before it was added to the cooled (10° C.) solution of the alcohol. The reaction was allowed to warm to RT and stirred for 1 h after which time the reaction was diluted with CHCl$_3$ and ice-cold water. The organic layer was separated and the aqueous layer extracted with CHCl$_3$ (2×) before the combined aqueous layers was washed with water and sat. NaHCO$_{3(aq)}$, dried and the solvent evaporated to yield the crude product (256 mg). The sample was adsorbed onto SiO$_2$ and purified on 5 g (254/280 nm) using EtOAc/hexanes gradient 0-0% 3V, 0-75% 30CV. Fractions containing the title compound (m/z 435.172 (MH$^+$) were combined however this was not resolved from thiomethylether byproducts of both the target and SM (m/z 497.191 (MH$^+$). The sample was used without further manipulation.

2-(1-(3-(Benzyloxy)-6-methylpyridin-2-yl)-6,7-dihydro-5H-pyrrolo[1,2-c]imidazol-3-yl)-6-fluorophenol (58)

A mixture of (2-(3-(benzyloxy)-6-methylpicolinoyl)pyrrolidin-1-yl)(3-fluoro-2-hydroxyphenyl)methanone and (2-((3-(benzyloxy)-6-methylpyridin-2-yl)(hydroxy)methyl) pyrrolidin-1-yl)(3-fluoro-2-hydroxy-4-(methylthiomethyl)phenyl)methanone (~96 mg) and NH$_4$OAc (256 mg) were dissolved in AcOH (2 mL) and the mixture heated to 80° C. for 23 h. The sample was diluted with water before being extracted with EtOAc (3×) and the combined extracts washed with water and sat. NaCl(aq), dried and the solvent evaporated to yield the crude product (82 mg). The sample was adsorbed on SiO$_2$ and purified on 4 g SiO$_2$ (254/280 nm) using MeOH/DCM gradient 0-0% 3CV, 0-10% 30CV, 10-20% 20CV and the fractions containing the desired compound were combined to yield the title compound (28 mg). ¹H NMR (CDCl₃, 600 MHz) δ 7.41-7.39 (2H, m), 7.35-7.32 (2H, m), 7.30-7.26 (2H, m), 7.11 (1H, d, J 8.5 Hz), 7.02 (1H, ddd, J 1.4, 8.1, 8.4 Hz), 6.90 (1H, d, J 8.4 Hz), 6.73 (1H, dt, J 4.8, 8.0 Hz), 5.20 (2H, s), 4.28 (2H, t, J 7.2 Hz), 3.04 (2H, t, J 7.3 Hz), 2.64 (2H, p, J 7.3 Hz), 2.49 (3H, s), m/z 416.172 (MH⁺).

2-(3-(3-Fluoro-2-hydroxyphenyl)-6,7-dihydro-5H-pyrrolo[1,2-c]imidazol-1-yl)-6-methylpyridin-3-ol (59)

2-(1-(3-(Benzyloxy)-6-methylpyridin-2-yl)-6,7-dihydro-5H-pyrrolo[1,2-c]imidazol-3-yl)-6-fluorophenol (58) (28 mg) was dissolved in EtOH (4 mL) before being treated with 10% Pd/C (15 mg) and the mixture placed under an atm of $H_{2(g)}$. The reaction was stirred for 23 h after which time the reactions was filtered and the solvent evaporated to yield the crude product. The sample was adsorbed onto $SiO_2$ and purified on 4 g $SiO_2$ (254/280 nm) using MeOH/DCM gradient 0-0% 3CV, 0-10% 30CV. The desired fractions were combined and the solvent evaporated to yield the title compound (7.2 mg) as a pale-yellow solid. HPLC (HPLC1) $t_R$ 5.84 min, ¹H NMR (d₆-DMSO, 600 MHz) δ 12.0 (1H, vbs), 11.2 (1H, bs), 7.39 (1H, d, J 7.8 Hz), 7.26 (1H, dd, J 8.3, 11.1 Hz), 7.12 (1H, d, J 8.3 Hz), 6.94 (1H, d, J 8.2 Hz), 6.93-6.90 (1H, m), 4.24 (2H, t, J 7.2 Hz), 3.14 (2H, t, J 7.3 Hz), 2.64 (2H, p, J 7.3 Hz), 2.39 (3H, s); m/z (MH⁴) 326.13.

Biological Examples

Measurement of Fe Efflux from Cells

Compounds of the current invention were assessed for their ability to efflux iron (Fe) from a cell using the following protocol.

The human neuroblastoma line BE(2)-M17 (M17) cell cultures were acquired from Sigma Aldrich (Catalogue #: 95011816). M17 cells were maintained in Opti-MEM reduced serum media supplemented with 10% fetal bovine serum (Bovogen, SFBSF) and passaged twice weekly. Cells were cultured at 37° C. in the presence of 5% $CO_2$. Culture supplies were sourced from Thermo Fisher unless otherwise stated.

A solution of ⁵⁷Fe isotope was prepared by dissolving ⁵⁷Fe metal (>95% enrichment, Trace Sciences International) in concentrated HCl to give a final concentration of 573 mM. From this master solution, a 10 mM working solution was prepared in sterile water. The working solution was used within two months of preparation.

M17 cells were loaded with iron initially by seeding into 48-well plates at a density of 0.15×10⁶ cells per well in 0.5 mL media. After 48 h, old media was discarded. Fresh media was added supplemented from the 10 mM ⁵⁷Fe working solution to yield media containing 20 μM ⁵⁷Fe isotope. Cells received 0.2 mL of this ⁵⁷Fe enriched media and were returned to the incubator for 20 h.

The ability of experimental compounds to efflux iron was determined by the dissolution of compounds in DMSO and diluted in Hanks' Balanced Salt Solution (HBSS) for treatment of M17 cells. After ⁵⁷Fe incubation, cells were rinsed twice with HBSS and treated with 0.15 ml trial compound for 2 h. Experimental substances were routinely screened at a concentration of 20 μM, however dilutions ranging from 1-40 μM were occasionally applied to further elucidate the properties of key compounds. All assays included a relevant vehicle (0.4%-0.8% DMSO) as well as a positive control. Following the treatment period, 0.1 mL of media was collected from cells and the extracellular ⁵⁷Fe content was analysed via inductively coupled mass spectrometry (ICP-MS, Agilent 7700×series instrument).

The ability of the compounds of the invention to efflux Fe from a cell was determined using the above protocol hence cells, having been pre-treated with Fe in the media for 24 h, were subsequently washed and treated with fresh, Fe free media either with or without the compound (20 μM). After 2 h the Fe levels in the media were measured and the increase determined as a percentage increase relative to the cell media in the absence of the compound.

$$\% \ Fe \ \text{efflux} = \frac{([Fe \ \text{in media}]_{Compound} - [Fe \ \text{in media}]_{No \ Compound})}{[Fe \ \text{in media}]_{No \ Compound}} \times 100$$

Representative data is provided in Table 1 where the % Fe efflux for the specified compounds of the invention lie in the following ranges: A<30%, B 30-100%, C 100-150%; D>150%

TABLE 1

| No. | % Fe Efflux Range |
|---|---|
| 1 | D |
| 2 | D |
| 3 | C |
| 4 | B |
| 5 | D |
| 6 | C |
| 7 | A |
| 8 | A |
| 9 | A |
| 10 | B |
| 11 | A |
| 12 | A |
| 13 | C |
| 14 | C |
| 15 | C |
| 16 | D |
| 17 | D |
| 18 | D |
| 19 | D |
| 20 | D |
| 21 | D |
| 22 | C |
| 23 | D |
| 24 | D |
| 25 | C |
| 26 | D |
| 27 | D |
| 28 | D |
| 29 | C |
| 30 | D |
| 36 | A |
| 37 | A |
| 38 | A |
| 50 | D |
| 51 | D |
| 52 | D |
| 53 | D |
| 54 | D |
| 56 | D |
| 57 | D |
| 59 | D |

The invention claimed is:

1. A compound of formula (I):

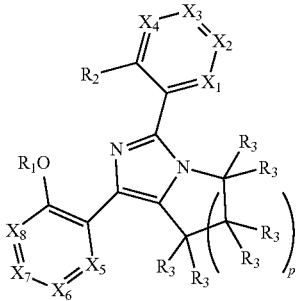

(I)

wherein
each of $X_1$ to $X_8$ are independently selected from the group consisting of N and $CR_3$, wherein 0, 1, 2, 3 or 4 of $X_1$ to $X_8$ are N;
$R_1$ is selected from the group consisting of hydrogen, alkyl, alkenyl, alkynyl, aryl, $(C(R_7)_2)_m$aryl, $C(O)R_4$ and $C(S)R_4$;
$R_2$ is selected from the group consisting of hydrogen, halo, $OR_5$, $SR_5$, $C(O)R_4$, $C(S)R_4$, $NO_2$, CN, $N(R_6)_2$, $OS(O)_nN(R_6)_2$ and $OS(O)_nR_4$;
each $R_3$ is independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$;
$R_4$ is selected from the group consisting of hydrogen, alkyl, alkenyl, alkynyl, haloalkyl, cycloalkyl, cycloalkenyl, aryl, heterocyclyl, heteroaryl, $OR_5$, $SR_5$ and $N(R_6)_2$;
$R_5$ is selected from the group consisting of hydrogen, alkyl, alkenyl, alkynyl, haloalkyl, cycloalkyl, cycloalkenyl, aryl, heterocyclyl, heteroaryl, C(O)alkyl, C(O) alkenyl, C(O)alkynyl, $S(O)_n R_4$ and $S(O)_n N(R_6)_2$;
$R_6$ is selected from the group consisting of hydrogen, alkyl, alkenyl, alkynyl, haloalkyl, cycloalkyl, cycloalkenyl, aryl, heterocyclyl and heteroaryl;
each $R_7$ is independently selected from the group consisting of hydrogen, alkyl, alkenyl, alkynyl and haloalkyl;
m is 0 or an integer from 1 to 6;
n is 1 or 2;
p is an integer from 1 to 4;
wherein each alkyl, alkenyl, alkynyl, cycloalkyl, cycloalkenyl, aryl, heterocyclyl and heteroaryl is optionally substituted;
or a pharmaceutically acceptable salt, stereoisomer or solvate thereof.

2. A compound according to claim 1 wherein $X_1$ to $X_8$ are independently selected from $CR_3$.

3. A compound according to claim 1 wherein one of $X_1$ to $X_8$ is N and the remainder are $CR_3$.

4. A compound according to claim 1 wherein two of $X_1$ to $X_8$ are N and the remainder are $CR_3$.

5. A compound according to claim 1 wherein one of the following applies:

i) one of $X_1$ to $X_4$ is N;
ii) one of $X_5$ to $X_8$ is N;
iii) $X_1$ is N;
iv) $X_5$ is N;
v) $X_6$ is N;
vi) $X_7$ is N or
vii) $X_8$ is N.

6. A compound according to claim 1 wherein $R_1$ is selected from the group consisting of hydrogen, $C_{1-6}$alkyl, $C_{2-6}$alkenyl, $C(O)C_{1-6}$alkyl, $CH_2$aryl and $C(O)OC_{1-6}$alkyl.

7. A compound according to claim 6 wherein $R_1$ is hydrogen or $CH_2$phenyl.

8. A compound according to claim 1 wherein $R_2$ is selected from hydrogen, OH, SH, fluoro, chloro, bromo, $OC_{1-6}$alkyl, $SC_{1-6}$alkyl, $C(O)OC_{1-6}$alkyl, $NO_2$, CN, $NH_2$, $OS(O)_2NH_2$, $OS(O)_2NH(C_{1-6}$alkyl), $OS(O)_2N(C_{1-6}$alkyl)$_2$ and $OS(O)_n C_{1-6}$alkyl.

9. A compound according to claim 8 wherein $R_2$ is OH.

10. A compound according to claim 1 wherein each $R_3$ is independently selected from the group consisting of hydrogen, halo, $C_{1-6}$alkyl, $C_{2-6}$alkenyl, $C_{1-6}$haloalkyl, cycloalkyl, cycloalkenyl, aryl, heterocyclyl, heteroaryl, $(CH_2)_q$cycloalkyl, $(CH_2)_q$cycloalkenyl, $(CH_2)_q$aryl, $(CH_2)_q$heterocyclyl, $(CH_2)_q$heteroaryl, OH, $(CH_2)_q$OH, SH, $(CH_2)_q$SH, $OC_{1-6}$alkyl, $SC_{1-6}$alkyl, $(CH_2)_q OC_{1-6}$alkyl, $(CH_2)_q SC_{1-6}$alkyl, $OC(O)C_{1-6}$alkyl, $(CH_2)_q OC(O)C_{1-6}$alkyl, $C(O)C_{1-6}$alkyl, $(CH_2)_q C(O)C_{1-6}$alkyl, $CO_2H$, $(CH_2)_q CO_2H$, $C(O)OC_{1-6}$alkyl, $(CH_2)_q C(O)OC_{1-6}$alkyl, $CONH_2$, $(CH_2)_q CONH_2$, CN, $(CH_2)_q CN$, $NO_2$, $(CH_2)_q NO_2$, $NH_2$, $NH(C_{1-6}$alkyl), $N(C_{1-6}$alkyl)$_2$, $(CH_2)_q NH_2$, $(CH_2)_q NH(C_{1-6}$alkyl), $(CH_2)_q N(C_{1-6}$alkyl)$_2$, $SO_3H$, $(CH_2)_q SO_3H$, $SO_3H$, $(CH_2)_q SO_3H$, $S(O)_2 C_{1-6}$alkyl, $(CH_2)_q S(O)_2 C_{1-6}$alkyl, $S(O)_2 OC_{1-6}$alkyl, $(CH_2)_q S(O)_2 OC_{1-6}$alkyl, $S(O)_2 NH_2$, $S(O)_2 NH(C_{1-6}$alkyl), $S(O)_2 N(C_{1-6}$alkyl)$_2$, $(CH_2)_q S(O)_2 NH_2$, $(CH_2)_q S(O)_2 NH(C_{1-6}$alkyl), $(CH_2)_q S(O)_2 N(C_{1-6}$alkyl)$_2$, $NHC(O)NH_2$, $NHC(O)NH(C_{1-6}$alkyl), $NHC(O)N(C_{1-6}$alkyl)$_2$, $(CH_2)_q NHC(O)NH_2$, $(CH_2)_q NHC(O)NH(C_{1-6}$alkyl) and $(CH_2)_q NHC(O)N(C_{1-6}$alkyl)$_2$ where q is an integer of from 1 to 3.

11. A compound according to claim 1 wherein p is 1, 2 or 3.

12. The compound according to claim 1 which is a compound of formula (II):

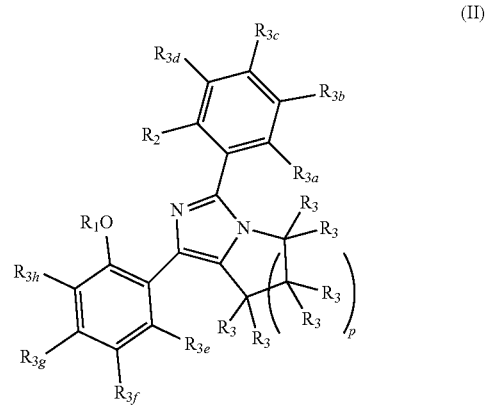

(II)

wherein $R_1$, $R_2$, $R_3$ and p are as defined for formula (I) and $R_{3a}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

13. The compound according to claim 1 which is a compound of formula (III):

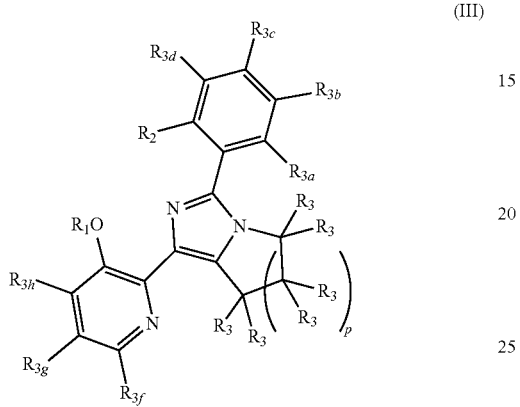

(III)

wherein $R_1$, $R_2$ and $R_3$ and p are as defined for formula (I) and $R_{3a}$ to $R_{3d}$ and $R_{3f}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

14. The compound according to claim 1 which is a compound of formula (IV):

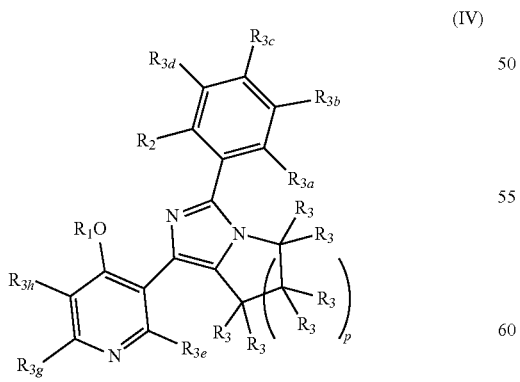

(IV)

wherein $R_1$, $R_2$ and $R_3$ and p are as defined for formula (I) and $R_{3a}$ to $R_{3e}$ and $R_{3g}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

15. The compound according to claim 1 which is a compound of formula (V):

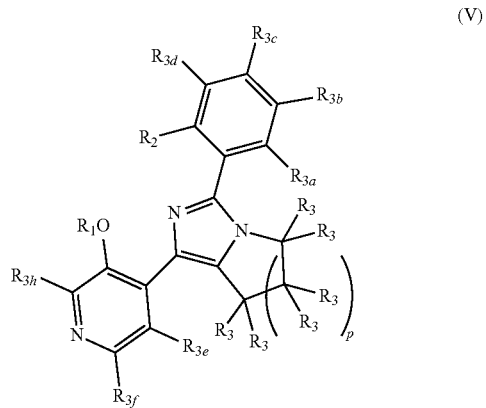

(V)

wherein $R_1$, $R_2$, $R_3$ and p are as defined for formula (I) and $R_{3a}$ to $R_{3f}$ and $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_mOR_5$, $(C(R_7)_2)_mSR_5$, $(C(R_7)_2)_mC(O)R_4$, $(C(R_7)_2)_mC(S)R_4$, $(C(R_7)_2)_mOC(O)R_4$, $(C(R_7)_2)_mSC(S)R_4$, $(C(R_7)_2)_mOC(S)R_4$, $(C(R_7)_2)_mSC(O)R_4$, $(C(R_7)_2)_mCN$, $(C(R_7)_2)_mNO_2$, $(C(R_7)_2)_mN(R_6)_2$, $(C(R_7)_2)_mS(O)_nR_4$, $(C(R_7)_2)_mN(R_6)C(O)N(R_6)_2$ and $(C(R_7)_2)_mN(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

16. The compound according to claim 1 which is a compound of formula (VI):

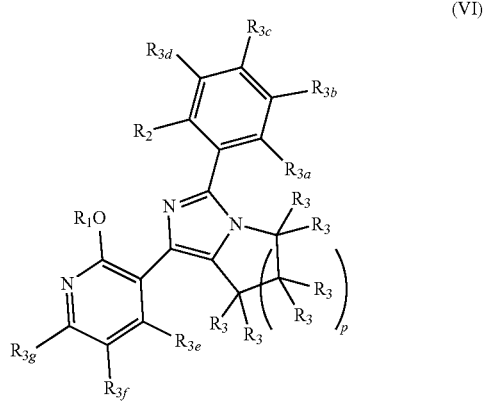

(VI)

wherein $R_1$, $R_2$, $R_3$ and p are as defined for formula (I) and $R_{3a}$ to $R_{3g}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

17. The compound according to claim 1 which is a compound of formula (VII):

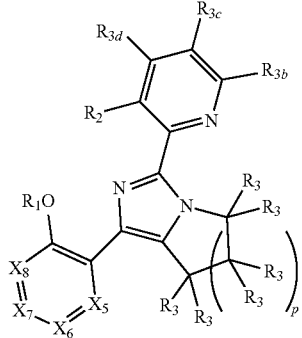

(VII)

wherein $R_1$, $R_2$, $R_3$ and p are as defined for formula (I), $X_5$ is N or $CR_{3e}$, $X_6$ is N or $CR_{3f}$, $X_7$ is N or $CR_{3g}$, $X_8$ is N or $CR_{3h}$ and $R_{3b}$ to $R_{3h}$ are each independently selected from the group consisting of hydrogen, halo, alkyl, alkenyl, alkynyl, haloalkyl, $(C(R_7)_2)_m$cycloalkyl, $(C(R_7)_2)_m$cycloalkenyl, $(C(R_7)_2)_m$aryl, $(C(R_7)_2)_m$heterocyclyl, $(C(R_7)_2)_m$heteroaryl, $(C(R_7)_2)_m OR_5$, $(C(R_7)_2)_m SR_5$, $(C(R_7)_2)_m C(O)R_4$, $(C(R_7)_2)_m C(S)R_4$, $(C(R_7)_2)_m OC(O)R_4$, $(C(R_7)_2)_m SC(S)R_4$, $(C(R_7)_2)_m OC(S)R_4$, $(C(R_7)_2)_m SC(O)R_4$, $(C(R_7)_2)_m CN$, $(C(R_7)_2)_m NO_2$, $(C(R_7)_2)_m N(R_6)_2$, $(C(R_7)_2)_m S(O)_n R_4$, $(C(R_7)_2)_m N(R_6)C(O)N(R_6)_2$ and $(C(R_7)_2)_m N(R_6)C(S)N(R_6)_2$; wherein $R_4$, $R_5$, $R_6$, $R_7$ and m are as defined for formula (I);

or a pharmaceutically acceptable salt, stereoisomer or solvate thereof.

18. A pharmaceutical composition comprising a compound of formula (I) according to claim 1 or a pharmaceutically acceptable salt or solvate thereof and a pharmaceutically acceptable carrier and/or excipient.

* * * * *